US009365901B2

(12) United States Patent
Pepin et al.

(10) Patent No.: US 9,365,901 B2
(45) Date of Patent: *Jun. 14, 2016

(54) MONITORING IMMUNOGLOBULIN HEAVY CHAIN EVOLUTION IN B-CELL ACUTE LYMPHOBLASTIC LEUKEMIA

(71) Applicant: Adaptive Biotechnologies Corp., Seattle, WA (US)

(72) Inventors: Francois Pepin, San Bruno, CA (US); Victoria Carlton, San Francisco, CA (US); Mark Klinger, San Francisco, CA (US); Malek Faham, Pacifica, CA (US)

(73) Assignee: Adaptive Biotechnologies Corp., Seattle, WA (US)

( * ) Notice: Subject to any disclaimer, the term of this patent is extended or adjusted under 35 U.S.C. 154(b) by 108 days.

This patent is subject to a terminal disclaimer.

(21) Appl. No.: 13/861,941

(22) Filed: Apr. 12, 2013

(65) Prior Publication Data

US 2013/0202718 A1 Aug. 8, 2013

Related U.S. Application Data

(63) Continuation-in-part of application No. 13/100,365, filed on May 4, 2011, now Pat. No. 8,748,103, and a continuation-in-part of application No. 12/615,263, filed on Nov. 9, 2009, now Pat. No. 8,236,503.

(60) Provisional application No. 61/332,175, filed on May 6, 2010, provisional application No. 61/445,743, filed on Feb. 23, 2011, provisional application No. 61/446,822, filed on Feb. 25, 2011, provisional application No. 61/112,693, filed on Nov. 7, 2008, provisional application No. 61/636,518, filed on Apr. 20, 2012, provisional application No. 61/655,390, filed on Jun. 4, 2012.

(51) Int. Cl.
C12Q 1/68 (2006.01)
C12P 19/34 (2006.01)

(52) U.S. Cl.
CPC ........ *C12Q 1/6886* (2013.01); *C12Q 2600/112* (2013.01); *C12Q 2600/156* (2013.01)

(58) Field of Classification Search
USPC .................................. 435/6.12, 91.2
See application file for complete search history.

(56) References Cited

U.S. PATENT DOCUMENTS

| | | |
|---|---|---|
| 3,270,960 A | 9/1966 | Phillips |
| 3,773,919 A | 11/1973 | Boswell et al. |
| 4,474,754 A | 10/1984 | Shimizu et al. |
| 4,683,195 A | 7/1987 | Mullis et al. |
| 4,683,202 A | 7/1987 | Mullis |
| 4,751,188 A | 6/1988 | Valet |
| 4,800,159 A | 1/1989 | Mullis et al. |
| 4,876,189 A | 10/1989 | Schetters |
| 4,942,124 A | 7/1990 | Church |
| 4,965,188 A | 10/1990 | Mullis et al. |
| 5,075,217 A | 12/1991 | Weber |
| 5,126,022 A | 6/1992 | Soane et al. |
| 5,149,625 A | 9/1992 | Church et al. |
| 5,168,038 A | 12/1992 | Tecott et al. |
| 5,189,147 A | 2/1993 | Saito et al. |
| 5,210,015 A | 5/1993 | Gelfand et al. |
| 5,213,960 A | 5/1993 | Chang |
| 5,231,012 A | 7/1993 | Mosmann et al. |
| 5,296,351 A | 3/1994 | Morley |
| 5,298,396 A | 3/1994 | Kotzin et al. |
| 5,326,696 A | 7/1994 | Chang |
| 5,336,598 A | 8/1994 | Kotzin et al. |
| 5,364,759 A | 11/1994 | Caskey et al. |
| 5,399,491 A | 3/1995 | Kacian et al. |
| 5,418,134 A | 5/1995 | Morley |
| 5,449,752 A | 9/1995 | Fujii et al. |
| 5,498,392 A | 3/1996 | Wilding et al. |
| 5,506,126 A | 4/1996 | Seed et al. |
| 5,587,128 A | 12/1996 | Wilding et al. |
| 5,627,037 A | 5/1997 | Ward |
| 5,627,052 A | 5/1997 | Schrader |
| 5,635,354 A | 6/1997 | Kourilsky et al. |
| 5,635,400 A | 6/1997 | Brenner |

(Continued)

FOREIGN PATENT DOCUMENTS

| | | |
|---|---|---|
| CN | 101225441 A | 7/2008 |
| CN | 102272327 A | 12/2011 |

(Continued)

OTHER PUBLICATIONS

Sandberg et al. Genome Research, 2001, vol. 11(8), p. 1404-1409.*
.S. Appl. No. 14/075,075, filed Nov. 8, 2013, Faham et al.
U.S. Appl. No. 14/404,435, filed Nov. 26, 2014, Faham et al.
Bertness, et al. T-cell receptor gene rearrangements as clinical markers of human T-cell lymphomas. N Engl J Med. Aug. 29, 1985;313(9):534-8.

(Continued)

*Primary Examiner* — Kenneth R. Horlick
*Assistant Examiner* — Joyce Tung
(74) *Attorney, Agent, or Firm* — Cooley LLP

(57) ABSTRACT

The invention is directed to methods of monitoring B-cell lymphoid proliferative disorders, such as B-cell acute lymphoblastic leukemias, by measuring the presence, absence and/or levels of correlating, or index, clonotypes and related clonotypes that have evolved therefrom, for example, as part of the disease condition. In one aspect, such methods are implemented by generating sequencing-based clonotype profiles and determining frequencies of correlating, or index, clonotypes present, including new clonotypes that have evolved therefrom, particularly, in the case of B-cell ALL, by VH substitution. The invention also includes use of such monitoring information to modify treatment status of a patient.

17 Claims, 9 Drawing Sheets

(56) References Cited

U.S. PATENT DOCUMENTS

| | | |
|---|---|---|
| 5,667,967 A | 9/1997 | Steinman et al. |
| 5,698,396 A | 12/1997 | Pfreundschuh |
| 5,699,798 A | 12/1997 | Hochman et al. |
| 5,741,676 A | 4/1998 | Fuller |
| 5,776,708 A | 7/1998 | Kotzin et al. |
| 5,776,737 A | 7/1998 | Dunn |
| 5,837,447 A | 11/1998 | Gorski |
| 5,846,719 A | 12/1998 | Brenner et al. |
| 5,854,033 A | 12/1998 | Lizardi |
| 5,858,195 A | 1/1999 | Ramsey |
| 5,925,517 A | 7/1999 | Tyagi et al. |
| 5,935,793 A | 8/1999 | Wong |
| 5,969,108 A | 10/1999 | McCafferty et al. |
| 5,981,176 A | 11/1999 | Wallace |
| 5,981,179 A | 11/1999 | Lorinez et al. |
| 6,001,229 A | 12/1999 | Ramsey |
| 6,010,607 A | 1/2000 | Ramsey |
| 6,033,546 A | 3/2000 | Ramsey |
| 6,054,034 A | 4/2000 | Soane et al. |
| 6,087,096 A | 7/2000 | Dau et al. |
| 6,090,592 A | 7/2000 | Adams et al. |
| 6,143,496 A | 11/2000 | Brown et al. |
| 6,172,214 B1 | 1/2001 | Brenner |
| 6,174,670 B1 | 1/2001 | Wittwer et al. |
| 6,258,540 B1 | 7/2001 | Lo et al. |
| 6,258,568 B1 | 7/2001 | Nyren |
| 6,300,070 B1 | 10/2001 | Boles et al. |
| 6,416,948 B1 | 7/2002 | Pilarski et al. |
| 6,440,706 B1 | 8/2002 | Vogelstein et al. |
| 6,458,530 B1 | 10/2002 | Morris et al. |
| 6,489,103 B1 | 12/2002 | Griffiths et al. |
| 6,524,829 B1 | 2/2003 | Seegar |
| 6,569,627 B2 | 5/2003 | Wittwer et al. |
| 6,596,492 B2 | 7/2003 | Avery et al. |
| 6,605,272 B2 | 8/2003 | Novak et al. |
| 6,613,525 B2 | 9/2003 | Nelson et al. |
| 6,667,159 B1 | 12/2003 | Walt |
| 6,753,147 B2 | 6/2004 | Vogelstein et al. |
| 6,787,308 B2 | 9/2004 | Balasubramanian et al. |
| 6,792,355 B2 | 9/2004 | Hansen et al. |
| 6,794,499 B2 | 9/2004 | Wengel et al. |
| 6,806,079 B1 | 10/2004 | McCafferty et al. |
| 6,858,412 B2 | 2/2005 | Willis et al. |
| 6,919,434 B1 | 7/2005 | Goto et al. |
| 6,964,850 B2 | 11/2005 | Bevilacqua |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,228 B2 | 1/2007 | Hashmi et al. |
| 7,157,274 B2 | 1/2007 | Bohm et al. |
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,665 B2 | 7/2008 | Brenner |
| 7,432,084 B2 | 10/2008 | Shoemaker |
| 7,537,897 B2 | 5/2009 | Brenner et al. |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer et al. |
| 7,700,323 B2 | 4/2010 | Willis et al. |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | Macevicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham et al. |
| 8,628,927 B2 | 1/2014 | Faham et al. |
| 8,685,678 B2 | 4/2014 | Casbon |
| 8,691,510 B2 | 4/2014 | Faham et al. |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham et al. |
| 8,759,036 B2 | 6/2014 | Wang |
| 8,795,970 B2 | 8/2014 | Faham et al. |
| 8,826,321 B2 | 9/2014 | Cronin et al. |
| 8,835,358 B2 | 9/2014 | Fodor |
| 9,012,148 B2 | 4/2015 | Han et al. |
| 9,043,160 B1 | 5/2015 | Moorhead et al. |
| 9,150,905 B2 | 10/2015 | Robins et al. |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0134326 A1 | 7/2003 | Hansen |
| 2003/0162197 A1 | 8/2003 | Morley et al. |
| 2003/0207300 A1 | 11/2003 | Matray et al. |
| 2004/0033490 A1 | 2/2004 | Laird et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0235061 A1 | 11/2004 | Wilkie et al. |
| 2004/0248172 A1 | 12/2004 | Samoszuk et al. |
| 2005/0037356 A1 | 2/2005 | Gullberg et al. |
| 2005/0064421 A1 | 3/2005 | Gehrmann et al. |
| 2005/0142577 A1 | 6/2005 | Jones et al. |
| 2005/0250147 A1 | 11/2005 | Macevicz |
| 2005/0255482 A1 | 11/2005 | Morley et al. |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2006/0263789 A1 | 11/2006 | Kincaid |
| 2007/0020640 A1 | 1/2007 | McCloskey et al. |
| 2007/0020670 A1 | 1/2007 | Loken et al. |
| 2007/0105105 A1 | 5/2007 | Clelland et al. |

(56) References Cited

U.S. PATENT DOCUMENTS

| | | |
|---|---|---|
| 2007/0117134 A1 | 5/2007 | Kou |
| 2007/0160994 A1 | 7/2007 | Lim et al. |
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |
| 2008/0166704 A1 | 7/2008 | Marche et al. |
| 2008/0166718 A1 | 7/2008 | Lim et al. |
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Bureznski |
| 2008/0286777 A1 | 11/2008 | Candeias et al. |
| 2009/0026082 A1 | 1/2009 | Rothberg et al. |
| 2009/0053184 A1 | 2/2009 | Morgan et al. |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |
| 2009/0233301 A1 | 9/2009 | Lee |
| 2009/0253581 A1 | 10/2009 | Van Eijk et al. |
| 2009/0264299 A1 | 10/2009 | Drmanac et al. |
| 2009/0280489 A1 | 11/2009 | Devinder et al. |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021894 A1 | 1/2010 | Mirkin et al. |
| 2010/0021896 A1 | 1/2010 | Han |
| 2010/0021984 A1 | 1/2010 | Edd |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0105886 A1 | 4/2010 | Woudenberg |
| 2010/0137143 A1 | 6/2010 | Rothberg et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0330571 A1 | 12/2010 | Robins et al. |
| 2011/0003291 A1 | 1/2011 | Pasqual |
| 2011/0014659 A1 | 1/2011 | Balazs et al. |
| 2011/0097712 A1 | 4/2011 | Cantor et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0195253 A1 | 8/2011 | Hinz et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0251099 A1 | 10/2011 | Visvanathan et al. |
| 2012/0035062 A1 | 2/2012 | Schultz et al. |
| 2012/0058902 A1 | 3/2012 | Livingston et al. |
| 2012/0071331 A1 | 3/2012 | Casbon et al. |
| 2012/0073667 A1 | 3/2012 | Schultz et al. |
| 2012/0122714 A1 | 5/2012 | Samuels |
| 2012/0135409 A1 | 5/2012 | Faham et al. |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0220466 A1 | 8/2012 | Fire et al. |
| 2013/0005584 A1 | 1/2013 | Faham et al. |
| 2013/0017957 A1 | 1/2013 | Faham et al. |
| 2013/0065768 A1 | 3/2013 | Zheng et al. |
| 2013/0116130 A1 | 5/2013 | Fu |
| 2013/0123120 A1 | 5/2013 | Zimmermann et al. |
| 2013/0136799 A1 | 5/2013 | Faham et al. |
| 2013/0150252 A1 | 6/2013 | Faham et al. |
| 2013/0196328 A1 | 8/2013 | Pepin et al. |
| 2013/0196861 A1 | 8/2013 | Quake |
| 2013/0236895 A1 | 9/2013 | Faham et al. |
| 2013/0253842 A1 | 9/2013 | Sherwood et al. |
| 2013/0267427 A1 | 10/2013 | Faham et al. |
| 2013/0288237 A1 | 10/2013 | Robins et al. |
| 2013/0302801 A1 | 11/2013 | Asbury et al. |
| 2013/0324422 A1 | 12/2013 | Faham et al. |
| 2013/0344066 A1 | 12/2013 | Faham et al. |
| 2014/0057799 A1 | 2/2014 | Johnson et al. |
| 2014/0094376 A1 | 4/2014 | Han |
| 2014/0127699 A1 | 5/2014 | Han |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0234835 A1 | 8/2014 | Pepin et al. |
| 2014/0235454 A1 | 8/2014 | Faham et al. |
| 2014/0255929 A1 | 9/2014 | Zheng |
| 2014/0255944 A1 | 9/2014 | Carlton et al. |
| 2014/0256567 A1 | 9/2014 | Robins et al. |
| 2014/0256592 A1 | 9/2014 | Faham et al. |
| 2014/0315725 A1 | 10/2014 | Faham et al. |
| 2014/0322716 A1 | 10/2014 | Robins |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham |
| 2014/0356339 A1 | 12/2014 | Faham et al. |
| 2015/0017652 A1 | 1/2015 | Robins et al. |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham |
| 2015/0051089 A1 | 2/2015 | Robins et al. |
| 2015/0065352 A1 | 3/2015 | Faham et al. |
| 2015/0133317 A1 | 5/2015 | Robinson et al. |
| 2015/0167080 A1 | 6/2015 | Moorhead et al. |
| 2015/0203897 A1 | 7/2015 | Robins et al. |
| 2015/0218656 A1 | 8/2015 | Kirsch et al. |
| 2015/0247182 A1 | 9/2015 | Faham et al. |
| 2015/0247198 A1 | 9/2015 | Klinger et al. |
| 2015/0247201 A1 | 9/2015 | Faham et al. |
| 2015/0252419 A1 | 9/2015 | Moorhead et al. |
| 2015/0252422 A1 | 9/2015 | Faham et al. |
| 2015/0259734 A1 | 9/2015 | Asbury et al. |
| 2015/0275296 A1 | 10/2015 | Klinger et al. |
| 2015/0275308 A1 | 10/2015 | Carlton et al. |
| 2015/0299785 A1 | 10/2015 | Livingston et al. |
| 2015/0299786 A1 | 10/2015 | Robins et al. |
| 2015/0299800 A1 | 10/2015 | Faham et al. |

FOREIGN PATENT DOCUMENTS

| | | |
|---|---|---|
| EP | 0303459 A2 | 2/1989 |
| EP | 0799897 A1 | 10/1997 |
| EP | 1544308 A1 | 6/2005 |
| EP | 1549764 B1 | 7/2005 |
| EP | 0972081 B1 | 6/2007 |
| EP | 1544308 B1 | 1/2009 |
| EP | 2062982 A1 | 5/2009 |
| EP | 2088432 A1 | 8/2009 |
| EP | 2364368 B1 | 1/2014 |
| JP | 4262799 A | 9/1992 |
| JP | 2002-503954 A | 2/2001 |
| JP | 2005-245381 A | 9/2005 |
| JP | 2006-501842 A | 1/2006 |

(56) References Cited

FOREIGN PATENT DOCUMENTS

| | | |
|---|---|---|
| JP | 2007-515955 A | 6/2007 |
| JP | 2007-536939 A | 12/2007 |
| JP | 2008099588 A | 5/2008 |
| WO | WO 93/01838 A1 | 2/1993 |
| WO | WO 2005/059176 A1 | 6/1995 |
| WO | WO 95/28481 A1 | 10/1995 |
| WO | WO 97/13877 A1 | 4/1997 |
| WO | WO 97/18330 A1 | 5/1997 |
| WO | WO 97/46706 A1 | 12/1997 |
| WO | WO 98/01738 A1 | 1/1998 |
| WO | WO 98/44151 A1 | 10/1998 |
| WO | WO 99/19717 A1 | 4/1999 |
| WO | WO 99/20798 A1 | 4/1999 |
| WO | WO 02/24322 A2 | 3/2002 |
| WO | WO 03/008624 A2 | 1/2003 |
| WO | WO 03/044225 A2 | 5/2003 |
| WO | WO 03/052101 A1 | 6/2003 |
| WO | WO 03/059155 A2 | 7/2003 |
| WO | WO 03/044225 A3 | 12/2003 |
| WO | WO 2004/003820 A2 | 1/2004 |
| WO | WO 03/059155 A3 | 3/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/046098 A3 | 8/2004 |
| WO | WO 2004/096985 A2 | 11/2004 |
| WO | WO 2005/005651 A2 | 1/2005 |
| WO | WO 2005/042774 A2 | 5/2005 |
| WO | WO 2005/053603 A2 | 6/2005 |
| WO | WO 2005/056828 A1 | 6/2005 |
| WO | WO 2005/084134 A2 | 9/2005 |
| WO | WO 2005/111242 A2 | 11/2005 |
| WO | WO 2005/113803 A1 | 12/2005 |
| WO | WO 2006/076205 A2 | 7/2006 |
| WO | WO 2006/110855 A2 | 10/2006 |
| WO | WO 2006/116155 A2 | 11/2006 |
| WO | WO 2006/138284 A2 | 12/2006 |
| WO | WO 2007/134220 A2 | 11/2007 |
| WO | WO 2008/026927 A2 | 3/2008 |
| WO | WO 2008/026927 A3 | 4/2008 |
| WO | WO 2008/039694 A2 | 4/2008 |
| WO | WO 2008/108803 A2 | 9/2008 |
| WO | WO 2008/108803 A3 | 12/2008 |
| WO | WO 2008/147879 A1 | 12/2008 |
| WO | WO 2009/015296 A1 | 1/2009 |
| WO | WO 2009/017678 A2 | 2/2009 |
| WO | WO 2009/019657 A2 | 2/2009 |
| WO | WO 2009/021215 A1 | 2/2009 |
| WO | WO 2006/076205 A3 | 4/2009 |
| WO | WO 2009/045898 A2 | 4/2009 |
| WO | WO 2009/070767 A2 | 6/2009 |
| WO | WO 2009/019657 A3 | 8/2009 |
| WO | WO 2009/095567 A2 | 8/2009 |
| WO | WO 2009/108860 A2 | 9/2009 |
| WO | WO 2009/108866 A2 | 9/2009 |
| WO | WO 2009/070767 A3 | 10/2009 |
| WO | WO 2009/108866 A3 | 10/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |
| WO | WO 2009/158521 A2 | 12/2009 |
| WO | WO 2009/108860 A3 | 1/2010 |
| WO | WO 2009/137255 A3 | 1/2010 |
| WO | WO 2010/011894 A1 | 1/2010 |
| WO | WO 2009/151628 A3 | 2/2010 |
| WO | WO 2010/036352 A1 | 4/2010 |
| WO | WO 2009/158521 A3 | 5/2010 |
| WO | WO 2010/053587 A2 | 5/2010 |
| WO | WO 2010/151416 A1 | 12/2010 |
| WO | WO 2011/083296 A1 | 7/2011 |
| WO | WO 2011/083996 A2 | 7/2011 |
| WO | WO 2011/106738 A2 | 9/2011 |
| WO | WO 2011/107595 A1 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2011/106738 A3 | 12/2011 |
| WO | WO 2012/027503 A2 | 3/2012 |
| WO | WO 2012/048340 A2 | 4/2012 |
| WO | WO 2012/048341 A1 | 4/2012 |
| WO | WO 2012/055929 A1 | 5/2012 |
| WO | WO 2012/061832 A1 | 5/2012 |
| WO | WO 2012/048340 A3 | 6/2012 |
| WO | WO 2012/083069 A2 | 6/2012 |
| WO | WO 2012/083225 A2 | 6/2012 |
| WO | WO 2012/142213 A2 | 10/2012 |
| WO | WO 2012/148497 A2 | 11/2012 |
| WO | WO 2012/159754 A2 | 11/2012 |
| WO | WO 2013/033721 A1 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/130512 A2 | 9/2013 |
| WO | WO 2013/131074 A1 | 9/2013 |
| WO | WO 2013/134162 A2 | 9/2013 |
| WO | WO 2013/134302 A1 | 9/2013 |
| WO | PCT/US2013/065493 | 10/2013 |
| WO | PCT/US2013/065509 | 10/2013 |
| WO | PCT/US2013/065757 | 10/2013 |
| WO | WO 2013/155119 A1 | 10/2013 |
| WO | WO 2013/158936 A1 | 10/2013 |
| WO | WO 2013/169957 A1 | 11/2013 |
| WO | WO 2013/181428 A2 | 12/2013 |
| WO | WO 2013/188471 A2 | 12/2013 |
| WO | WO 2013/188831 A1 | 12/2013 |
| WO | WO 2014/018460 A1 | 1/2014 |
| WO | PCT/US2014/017416 | 2/2014 |
| WO | WO 2014/026031 A1 | 2/2014 |
| WO | WO 2014/062945 A1 | 4/2014 |
| WO | WO 2014/062959 A1 | 4/2014 |
| WO | WO 2014/066184 A1 | 5/2014 |
| WO | PCT/US2014/044971 | 6/2014 |
| WO | PCT/US2014/047909 | 7/2014 |
| WO | WO 2014/130685 A1 | 8/2014 |
| WO | PCT/US2014/061260 | 10/2014 |
| WO | WO 2015/002908 A1 | 1/2015 |
| WO | WO 2015/013461 A2 | 1/2015 |
| WO | WO 2015/058159 A1 | 4/2015 |

OTHER PUBLICATIONS

Qu, et al. Efficient frequency-based de novo short-read clustering for error trimming in next-generation sequencing. Genome Res. Jul. 2009;19(7):1309-15. doi: 10.1101/gr.089151.108. Epub May 13, 2009.
Weiss, et al. Clonal rearrangements of T-cell receptor genes in mycosis fungoides and dermatopathic lymphadenopathy. N Engl J Med. Aug. 29, 1985;313(9):539-44.
U.S. Appl. No. 14/173,712, filed Feb. 5, 2014, Faham et al.
U.S. Appl. No. 14/176,551, filed Feb. 10, 2014, Faham et al.
Kita, et al. T cell receptor clonotypes in skin lesions from patients with systemic lupus erythematosus. J Invest Dermatol. Jan. 1998;110(1):41-6.
Office action dated Feb. 18, 2014 for U.S. Appl. No. 13/459,701.
Office action dated Aug. 11, 2014 for U.S. Appl. No. 13/196,885.
Drossman, et al. High-speed separations of DNA sequencing reactions by capillary electrophoresis. Anal Chem. May 1, 1990;62(9):900-3.
Office action dated Nov. 20, 2014 for U.S. Appl. No. 13/214,111.
Andreasson, et al. The human IgE-encoding transcriptome to assess antibody repertoires and repertoire evolution. J Mol Biol. Sep. 15, 2006;362(2):212-27. Epub Aug. 14, 2006.
Office action dated Oct. 7, 2013 for U.S. Appl. No. 13/459,701.

(56) References Cited

OTHER PUBLICATIONS

Office action dated Oct. 16, 2013 for U.S. Appl. No. 13/487,980.
Office action dated Nov. 6, 2013 for U.S. Appl. No. 13/468,323.
Office action dated Nov. 27, 2013 for U.S. Appl. No. 13/196,885.
Notice of allowance dated Dec. 15, 2014 for U.S. Appl. No. 13/196,885.
Office action dated Dec. 10, 2014 for U.S. Appl. No. 14/329,873.
U.S. Appl. No. 13/905,406, filed May 30, 2013, Faham et al.
U.S. Appl. No. 13/908,813, filed Jun. 3, 2013, Faham et al.
Chen, A novel approach for the analysis of T-cell reconstitution by using a T-cell receptor beta-based oligonucleotide microarray in hematopoietic stem cell transplantation. Exp Hematol. May 2007;35(5):831-41.
Office action dated Jun. 6, 2013 for U.S. Appl. No. 13/100,365.
Office action dated Jun. 6, 2013 for U.S. Appl. No. 13/100,389.
Office action dated Jun. 20, 2013 for U.S. Appl. No. 13/214,111.
U.S. Appl. No. 14/329,873, filed Jul. 11, 2014, Faham et al.
U.S. Appl. No. 14/350,516, filed Apr. 8, 2014, Faham et al.
U.S. Appl. No. 14/350,785, filed Apr. 9, 2014, Faham et al.
Kou, et al. T-Cell receptor Vbeta repertoire CDR3 length diversity differs within CD45RA and CD45RO T-cell subsets in healthy and human immunodeficiency virus-infected children. Clin Diagn Lab Immunol. Nov. 2000;7(6):953-9.
Miqueu, et al. Statistical analysis of CDR3 length distributions for the assessment of T and B cell repertoire biases. Mol Immunol. Feb. 2007;44(6):1057-64. Epub Aug. 22, 2006.
Office action dated May 16, 2014 for U.S. Appl. No. 13/196,885.
Office action dated Jul. 5, 2013 for U.S. Appl. No. 13/763,978.
Notice of allowance dated Sep. 12, 2014 for U.S. Appl. No. 13/214,111.
Office action dated Oct. 8, 2014 for U.S. Appl. No. 13/459,701.
U.S. Appl. No. 61/112,693, filed Nov. 7, 2008, Faham et al.
Abath, et al. Single-tube nested PCR using immobilized internal primers. Biotechniques. Dec. 2002;33(6):1210-2, 1214.
Altin, et al. The role of CD45 and CD45-associated molecules in T cell activation. Immunol Cell Biol. Oct. 1997;75(5):430-45.
Arnaout. Specificity and overlap in gene segment-defined antibody repertoires. C Genomics. Oct. 28, 2005;6:148.
Damle, et al. B-cell chronic lymphocytic leukemia cells express a surface membrane phenotype of activated, antigen-experienced B lymphocytes. Blood. Jun. 1, 2002;99(11):4087-93.
De Bona, et al. Optimal spliced alignments of short sequence reads. Bioinformatics. Aug. 15, 2008;24(16):i174-80. doi: 10.1093/bioinformatics/btn300.
Diluvio, et al. Identical TCR beta-chain rearrangements in streptococcal angina and skin lesions of patients with psoriasis vulgaris. J Immunol. Jun. 1, 2006;176(11):7104-11.
Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Droege, et al. The Genome Sequencer FLX System—longer reads, more applications, straight forward bioinformatics and more complete data sets. J Biotechnol. Aug. 31, 2008;136(1-2):3-10. doi: 10.1016/j.jbiotec.2008.03.021. Epub Jun. 21, 2008.
Eisenstein. Personalized, sequencing-based immune profiling spurs startups. Nat Biotechnol. Mar. 2013;31(3):184-6. doi: 10.1038/nbt0313-184b.
Erlich, et al. Alta-Cyclic: a self-optimizing base caller for next-generation sequencing. Nat Methods. Aug. 2008;5(8):679-82. doi: 10.1038/nmeth.1230. Epub Jul. 6, 2008.
European opposition dated Oct. 14, 2014 for EP Application No. 09764971.1.
European opposition dated Oct. 15, 2014 for EP Application No. 09764971.1. (in French only).
Furmanski, et al. Public T cell receptor beta-chains are not advantaged during positive selection. J Immunol. Jan. 15, 2008;180(2):1029-39.
GIGA—Roche 454 FLX technology how it works. Fiche technique du Centre Interdisciplinaire de Genoproteomique Appliquee (Universite de Liege, Belgique). Accessed Oct. 15, 2014.
Gomes, et al. Single-tube nested PCR using immobilized internal primers for the identification of dengue virus serotypes. J Virol Methods. Oct. 2007;145(1):76-9. Epub Jun. 15, 2007.
Gupta. Single-molecule DNA sequencing technologies for future genomics research. Trends Biotechnol. Nov. 2008;26(11):602-11. doi: 10.1016/j.tibtech.2008.07.003. Epub Aug. 21, 2008.
Heger. Roche's 454 Eyes Immune Repertoire Sequencing as Key Application for Long-Read Platform. Feb. 2, 2010. http://www.genomeweb.com/print/932624.
IlluminA Systems & Software, Technology Spotlight, DNA Sequencing with Solexa® Technology, Illumina, Inc., Pub. No. 770-2007-002, 2007.
Jurkat, Clone 6-1 (ATCC TIB-152) Webpage retrievable from the ATCC under http://www.lgcstandards-atcc.org/Products/A11MB-152.aspx#characteristics. Accessed Oct. 14, 2014.
Lin, et al. Multiplex genotype determination at a large number of gene loci. Proc Natl Acad Sci U S A. Mar. 19, 1996;93(6):2582-7.
Lowe, et al. A computer program for selection of oligonucleotide primers for polymerase chain reactions. Nucleic Acids Res. Apr. 11, 1990;18(7):1757-61.
Mardis. Next-generation DNA sequencing methods. Annu Rev Genomics Hum Genet. 2008;9:387-402. doi: 10.1146/annurev.genom.9.081307.164359.
Miceli, et al. The roles of CD4 and CD8 in T cell activation. Semin Immunol. May 1991;3(3):133-41. Abstract only.
Office action dated May 2, 2011 for U.S. Appl. No. 12/425,310.
Office action dated May 8, 2014 for U.S. Appl. No. 12/425,310.
Office action dated Aug. 6, 2010 for U.S. Appl. No. 12/425,310.
Quick. SOLiD System—a next-gen DNA sequencing platform announced, Gizmag online magazine, http://www.mizmag.com/go/8248, pp. 1-5, Oct. 2007.
Robins. Immunosequencing: applications of immune repertoire deep sequencing. Curr Opin Immunol. Oct. 2013;25(5):646-52. doi: 10.1016/j.coi.2013.09.017. Epub Oct. 16, 2013.
Sequenta and iRepertoire Join Forces on Blood Cancer Testing. BusinessWire. Aug. 8, 2013. http://www.businesswire.com/news/home/20130808005363/en/Sequenta-iRepertoire-Join-Forces-Blo . . . #.VGTT9Wd0yUk.
Shendure, et al. Advanced sequencing technologies: methods and goals. Nat Rev Genet. May 2004;5(5):335-44.
Shendure, et al. Next-generation DNA sequencing. Nat Biotechnol. Oct. 2008;26(10):1135-45. doi: 10.1038/nbt1486.
Stanley. Essentials of Immunology & Serology, Delmar, Thomson Learning, Chapter 7, T cells, p. 95, 2002.
Striebich, et al. Selective accumulation of related CD4+ T cell clones in the synovial fluid of patients with rheumatoid arthritis. J Immunol Oct. 15, 1998;161(8):4428-36.
Supplemental material of Weinstein, et al. High-throughput sequencing of the zebrafish antibody repertoire. Science. May 8, 2009;324(5928):807-10. doi: 10.1126/science.1170020. www.sciencemag.org/cgi/content/full/324/5928/807/DC1.
Vanderborght, et al. Dynamic T cell receptor clonotype changes in synovial tissue of patients with early rheumatoid arthritis: effects of treatment with cyclosporin A (Neoral). J Rheumatol. Mar. 2002;29(3):416-26.
Wang, et al. HIV integration site selection: analysis by massively parallel pyrosequencing reveals association with epigenetic modifications. Genome Res. Aug. 2007;17(8):1186-94. Epub Jun. 1, 2007.
U.S. Appl. No. 14/317,087, filed Jun. 27, 2014, Asbury et al.
U.S. Appl. No. 14/363,276, filed Jun. 5, 2014, Faham et al.
U.S. Appl. No. 14/363,956, filed Jun. 9, 2014, Faham et al.
U.S. Appl. No. 14/364,961, filed Jun. 12, 2014, Faham et al.
U.S. Appl. No. 14/366,840, filed Jun. 19, 2014, Faham.
U.S. Appl. No. 14/383,101, filed Sep. 4, 2014, Faham et al.
U.S. Appl. No. 14/383,102, filed Sep. 4, 2014, Faham.
Nie, et al. Optical detection of single molecules. Annu Rev Biophys Biomol Struct. 1997;26:567-96.
Office action dated Aug. 26, 2014 for U.S. Appl. No. 14/075,075.
U.S. Appl. No. 61/045,586, filed Apr. 16, 2008, Han et al.
U.S. Appl. No. 12/945,678, filed Nov. 12, 2010, Faham et al.

(56) References Cited

OTHER PUBLICATIONS

U.S. Appl. No. 13/174,086, filed Jun. 30, 2011, Faham et al.
U.S. Appl. No. 13/196,885, filed Aug. 2, 2011, Moorhead et al.
U.S. Appl. No. 13/369,031, filed Feb. 8, 2012, Faham et al.
U.S. Appl. No. 13/487,980, filed Jun. 4, 2012, Faham et al.
U.S. Appl. No. 13/627,497, filed Sep. 26, 2012, Faham et al.
U.S. Appl. No. 13/763,978, filed Feb. 11, 2013, Faham et al.
Alatrakchi, et al. T-cell clonal in patients with B-cell lymphoproliferative disorders. J Immunother. Sep. 1998;21(5):363-70.
Arstila et al., "A direct estimate of the human αβ T cell receptor diversity," Science 286:958-961 (1999).
Bagnara, et al. IgV gene intraclonal diversification and clonal evolution in B-cell chronic lymphocytic leukaemia. Br J Haematol. Apr. 2006;133(1):50-8.
Batzoglou. The many faces of sequence alignment. Briefings in Bioinformatics. 2005; 6:6-22.
Beishuizen, et al. Analysis of Ig and T-cell receptor genes in 40 childhood acute lymphoblastic leukemias at diagnosis and subsequent relapse: implications for the detection of minimal residual disease by polymerase chain reaction analysis. Blood. Apr. 15, 1994;83(8):2238-47.
Bene, et al. How and why minimal residual disease studies are necessary in leukemia: a review from WP10 and WP12 of the European LeukaemiaNet. Haematologica. Aug. 2009;94(8):1135-50. Epub Jul. 7, 2009.
Benichou, et al. Rep-Seq: uncovering the immunological repertoire through next-generation sequencing. Immunology. Mar. 2012;135(3):183-91. doi: 10.1111/j.1365-2567.2011.03527.x.
Bonarius, et al. Monitoring the T-Cell Receptor Repertoire at Single-Clone Resolution. PLoS One. Dec. 20, 2006;1:e55.
Boria, et al. Primer sets for cloning the human repertoire of T cell receptor variable regions. BMC Immunology. 2008; 9:50.
Boyd et al. Measurement and clinical monitoring of human lymphocyte clonality by massively parallel VDJ pyrosequencing. Sci Transl. Med. 1(12):12ra23 (2009).
Boyd, et al. Individual variation in the germline Ig gene repertoire inferred from variable region gene rearrangements. J Immunol Jun. 15, 2010;184(12):6986-92. Epub May 21, 2010.
Brehm-Stecher, et al. Single-cell microbiology: tools, technologies, and applications. Microbiology and molecular biology reviews. 2004; 68(3):538-559.
Brisco, et al. Determining the repertoire of IGH gene rearrangements to develop molecular markers for minimal residual disease in B-lineage acute lymphoblastic leukemia. J Mol Diagn. May 2009;11(3):194-200. Epub Mar. 26, 2009.
Bruggemann, et al. Clinical significance of minimal residual disease quantification in adult patients with standard-risk acute lymphoblastic leukemia. Blood. Feb. 1, 2006;107(3):1116-23. Epub Sep. 29, 2005.
Bruggemann, et al. Standardized MRD quantification in European ALL trials: proceedings of the Second International Symposium on MRD assessment in Kiel, Germany, Sep. 18-20, 2008. Leukemia. Mar. 2010;24(3):521-35. doi: 10.1038/leu.2009.268. Epub Dec. 24, 2009.
Campana. Minimal residual disease in acute lymphoblastic leukemia. Semin Hematol. Jan. 2009;46(1):100-6.
Campbell et al., "Subclonal phylogenetic structures in cancer revealed by ultra-deep sequencing," PNAS 105(35):13081-13086 (2008).
Choi, et al. Clonal evolution in B-lineage acute lymphoblastic leukemia by contemporaneous VH-VH gene replacements and VH-DJH gene rearrangements. Blood. Mar. 15, 1996;87(6):2506-12.
Choi, et al. Relapse in children with acute lymphoblastic leukemia involving selection of a preexisting drug-resistant subclone. Blood. Jul. 15, 2007;110(2):632-9. Epub Mar. 19, 2007.
International Search Report for PCT Application PCT/US2009/006053 dated Jun. 15, 2010.
Costabile, et al. Molecular approaches in the diagnosis of primary immunodeficiency diseases. Hum Mutat. Dec. 2006;27(12):1163-73.
Cronn, et al. Multiplex sequencing of plant chloroplast genomes using Solexa sequencing-by-synthesis technology. Nucleic Acids Res. Nov. 2008;36(19):e122.
Curran et al., "Nucleotide sequencing of psoriatic arthritis tissue before and during methotrexate administration reveals a complex inflammatory T cell infiltrate with very few clones exhibiting features that suggest they drive the inflammatory process by recognizing autoantigens," J Immunol 172:1935-1944 (2004).
Currier, et al. Spectratype/immunoscope analysis of the expressed TCR repertoire. Current Protocols in Immunology. 2000; Supplement 38:10.28.1-10.28.24.
Davi, et al. Lymphocytic progenitor cell origin and clonal evolution of human B-lineage acute lymphoblastic leukemia. Blood. Jul. 15, 1996;88(2):609-21.
Davis, et al. Staining of cell surface human CD4 with 2-F-pyrimidine-containing RNA amptamers for flow cytometry. Nucleic Acids Research. 1998; 26(17):3915-3924.
Deng et al., "Gene profiling involved in immature CD4+ T lymphocyte responsible for systemic lupus erythematosus," Molecular Immunology 43:1497-1507 (2006).
Dohm, et al. Substantial biases in ultra-short read data sets from high throughput DNA sequencing. Nucleic Acids Research. 2008; 36:e105.
Dou, et al. Analysis of T cell receptor Vbeta gene usage during the course of disease in patients with chronic hepatitis B. J Biomed Sci. Nov.-Dec. 1998;5(6):428-34.
Du et al., "TCR spectratyping revealed T lymphocytes associated with graft-versus-host disease after allogeneic hematopoietic stem cell transplantation," Leukemia & Lymphoma 48(8):1618-1627 (2007).
Edd, et al. Controlled encapsulation of single cells into monodisperse picoliter drops. Lap Chip. 2008; 8(8):1262-1264.
European office action dated Mar. 28, 2012 for EP Application No. 09764927.1.
Freeman et al., "Profiling the T-cell receptor beta-chain repertoire by massively parallel sequencing," Genome Res. 19(10):1817-1824 (2009).
Fritz et al., "Alterations in the spinal cord T cell repertoire during relapsing experimental autoimmune encephalomyelitis," J Immunol 164:6662-6668 (2000).
Garcia-Castello, et al. Detection of clonal immunoglobulin and T-cell receptor gene recombination in hematological malignancies: monitoring minimal residual disease. Cardiovascular & Haematological Disorders-Drug Targets. 2009; 9:124-135.
Gerlinger, et al. How Darwinian models inform therapeutic failure initiated by clonal heterogeneity in cancer medicine. Br J Cancer. Oct. 12, 2010;103(8):1139-43. doi: 10.1038/sj.bjc.6605912. Epub Sep. 28, 2010.
Germano, et al. Clonality profile in relapsed precursor-B-ALL children by GeneScan and sequencing analyses. Consequences on minimal residual disease monitoring. Leukemia. Aug. 2003;17(8):1573-82.
Giuggio, et al. Evolution of the intrahepatic T cell repertoire during chronic hepataitis C virus infection. Viral Immunol. 2005;18(1):179-89.
Golembowski, et al. Clonal evolution in a primary cutaneous follicle center B cell lymphoma revealed by single cell analysis in sequential biopsies. Immunobiology. Apr. 2000;201(5):631-44.
Gonzalez, et al. Incomplete DJH rearrangements as a novel tumar target for minimal residual disease quantitation in multiple myeloma using real-time PCR. Leukemia. 2003; 17:1051-1057.
Gonzalez, et al. Incomplete DJH rearrangements of the IgH gene are frequent in multiple myeloma patients: immunobioligcal characteristics and clinical applications. Leukemia. 2003; 17:1398-1403.
Gorski, et al. Circulating T cell repertoire complexity in normal individuals and bone marrow recipients analyzed by CDR3 size spectratyping. Correlation with immune status. J Immunol May 15, 1994;152(10):5109-19.

(56) References Cited

OTHER PUBLICATIONS

Green, et al. Clonal diversity of Ig and T-cell-receptor gene rearrangements identifies a subset of childhood B-precursor acute lymphoblastic leukemia with increased risk of relapse. Blood. Aug. 1, 1998;92(3):952-8.
Guo, et al. Sequence changes at the V-D junction of the VH1 heavy chain of anti-phosphocholine antibodies alter binding to and protection against Streptococcus pneumoniae. Int Immunol. May 1997;9(5):665-77.
Gurrieri, et al. Chronic lymphocytic leukemia B cells can undergo somatic hypermutation and intraclonal immunoglobulin V(H)DJ(H) gene diversification. J Exp Med. Sep. 2, 2002;196(5):629-39.
Han, et al. Immunorepertoire analysis by multiplex PCR amplification and high throughput sequencing. Abstract. The 96 Annual Meeting of The American Association of Immunologists, Seattle, Washington, May 8-12, 2009. Available at http://jimmunol.org//cgi/content/meeting_abstract/182/1_MeetingAbstracts/42.6?sid=257929f1-97a9-4330-8e96-1750aa240e69. Accessed Nov. 24, 2010.
Heger, M. Studies Highlight Challenges of Immune Repertoire Sequencing's Clinical Applicability. Available at http://www.genomeweb.com/sequencing/studies-highlight-challenges-immune-repertoire-sequencings-clinical-applicabilit?hq_e=el&hq_m=966798&hq_l=10&hq_v=2357e2f0b3. Accessed Apr. 6, 2011.
Holt, "Q &A: BC cancer agency's Robert Holt on sequencing the immune repertoire in immune reconstitution," Genome Web (www.genomeweb.com) Jun. 30, 2009.
Howe, et al. T cell receptor clonotype analysis of T cell responses: Diagnostic application of a clonotypic database. Blood. 2003; 102:Abstract 3918.
Illumina. Data Sheet: Sequencing. Genomic Sequencing. Pub. No. 770.2008-016 Copyright 2010. Reference states: "Current as of Jan. 30, 2009.".
International search report and written opinion dated Sep. 22, 2011 for PCT Application No. US11/000791.
International search report and written opinion dated Oct. 19, 2011 for PCT Application No. US11/000792.
Ishii et al., "Isolation and expression profiling of genes upregulated in the peripheral blood cells of systemic lupus erythematosus patients," DNA Research 12:429-439 (2005).
Jacobi et al., "Activated memory B cell subsets correlate with disease activity in systemic lupus erythematosus: delineation by expression of CD27, IgD, and CD95," Arthritis & Rheumatism 58(6):1762-1773 (2008).
Jacobi et al., "Correlation between circulating CD27high plasma cells and disease activity in patients with systemic lupus erythematosus," Arthritis & Rheumatism 48(5):1332-1342 (2003).
Jena, et al. Amplification of genes, single transcripts and cDNA libraries from one cell and direct sequence analysis of amplified products derived from one molecule. J. Immunol Methods. 1996; 190:199-213.
Kato et al., "Analysis of accumulated T cell clonotypes in patients with systemic lupus erythematosus," Arthritis & Rheumatism 43(12):2712-2721 (2000).
Kim, et al an efficient and reliable DNA extraction method for preimplantation genetic diagnosis: a comparison of allele drop out and amplification rates using different single cell iysis methods. Fertility and Sterility. 2009; 92: 814-818.
Kim, et al. Polony multiplex analysis of gene expression (PMAGE) in mouse hypertrophic cardiomyopathy. Science. Jun. 8, 2007;316(5830):1481-4.
Kneba, et al. Analysis of rearranged T-cell receptor beta-chain genes by polymerase chain reaction (PCR0 DNA sequencing and automated high resolution PCR fragment analysis. Blood. 1995; 86:3930-3937.
Kobari, et al. T cells accumulating in the inflamed joints of a spontaneous murine model of rheumatoid arthritis become restricted to common clonotypes during disease progression. Int Immunol. Jan. 2004;16(1):131-8.

Langerak, et al. Immunoglobulin/T-cell receptor clonality diagnostics. Exoert Opin. Med. Diagn. 2007; 1(3):451-461.
Langerak, et al. Polymerase chain reaction-based clonality testing in tissue samples with reactive lymphoproliferations: usefulness and pitfalls. A report of the BIOMED-2 Concerted Action BMH4-CT98-3936. Leukemia. Feb. 2007;21(2):222-9. Epub Dec. 14, 2006.
Laplaud et al., "Blood T-cell receptor β chain transcriptome in multiple sclerosis. Characterization of the T cells with altered CDR3 length distribution," Brain 127:981-995 (2004).
Laplaud et al., "Serial blood T cell repertoire alterations in multiple sclerosis patients; correlation with clinical and MRI parameters," J Neroimmunol 177:151-160 (2006).
Li, et al. An improved one-tube RT-PCR protocol for analyzing single-cell gene expression in individual mammalian cells. Anal. Bioanal. Chem. 2010; 397: 1853-1859.
Li, et al. Clonal rearrangements in childhood and adult precursor B acute lymphoblastic leukemia: a comparative polymerase chain reaction study using multiple sets of primers. Eur J Haematol. Oct. 1999;63(4):211-8.
Li, et al. Detailed clonality analysis of relapsing precursor B acute lymphoblastic leukemia: implications for minimal residual disease detection. Leukemia Research. 2001; 25:1033-1045.
Li, et al. Sequence analysisn of clonal immunoglobulin and T-cell receptor gene rearrangements in children with acute lymphoblastic leukemia at diagnosis and at relapse: implications for pathogenesis and for the clinical utility of PCR-based methods of minimal residual disease detection. Blood. 2003; 102:4520-4526.
Li, et al. Utilization of Ig heavy chain variable, diversity, and joining gene segments in children with B-lineage acute lymphoblastic leukemia: implications for the mechanisms of VDJ recombination and for pathogenesis. Blood. Jun. 15, 2004;103(12):4602-9. Epub Mar. 9, 2004.
Logan, et al. High-throughput VDJ sequencing for quantification of minimal residual disease in chronic lymphocytic leukemia and immune reconstitution assessment. Proc Natl Acad Sci U S A. Dec. 27, 2011;108(52):21194-9. Epub Dec. 12, 2011.
Lovisa, et al. IGH and IGK gene rearrangements as PCR targets for pediatric Burkitt's lymphoma and mature B-ALL MRD analysis. Lab Invest. Oct. 2009;89(10):1182-6. Epub Aug. 10, 2009.
Luo et al., "Analysis of the interindividual conservation of T cell receptor α- and β-chain variable regions gene in the peripheral blood of patients with systemic lupus erythematosus," Clin Exp Immunol 154:316-324 (2008).
Margulies, et al. Genome sequencing in microfabricated high-density picolitre reactors. Nature. Sep. 15, 2005;437(7057):376-80. Epub Jul. 31, 2005.
Mato et al., "Correlation of clonal T cell expansion with disease activity in systemic lupus erythematosus," Int Immunol 9(4):547-554 (1997).
Matolcsy, et al. Clonal evolution of B cells in transformation from low- to high-grade lymphoma. Eur J Immunol. Apr. 1999;29(4):1253-64.
Matsumoto et al., "CDR3 spectratyping analysis of the TCR repertoire in myasthenia gravis," J Immunol 176:5100-5107 (2006).
Matsumoto et al., "Complementarity-determining region 3 spectratyping analysis of the TCR repertoire in multiple sclerosis," J Immunol 170:4846-4853 (2003).
Meleshko, et al. Rearrangements of IgH, TCRD and TCRG genes as clonality marker of childhood acute lymphoblastic leukemia. Exp Oncol. Dec. 2005;27(4):319-24.
Menezes et al., "A public T cell clonotype within a heterogeneous autoreactive repertoire is dominant in driving EAE," J Clin Invest 117(8):2176-2185 (2007).
Michalek, et al. Detection and long-term in vivo monitoring of individual tumor-specific T cell clones in patients with metastatic melanoma. J Immunol Jun. 1, 2007;178(11):6789-95.
Moss, et al. The human T cell reeptor in health and disease. Annu. Rev. Immunol. 1992; 10:71-96.
Muraro et al., "Molecular tracking of antigen-specific T cell clones in neurological immune-mediated disorders," Brain 126:20-31 (2003).
Nardi, et al. Quantitative monitoring by polymerase colony assay of known mutations resistant to ABL kinase inhibitors. Oncogene. Jan. 31, 2008;27(6):775-82. Epub Aug. 6, 2007, 1-8.

(56) References Cited

OTHER PUBLICATIONS

Neale, et al. Comparative analysis of flow cytometry and polymerase chain reaction for the detection of minimal residual disease in childhood acute lymphoblastic leukemia. Leukemia. May 2004;18(5):934-8.
Nguyen, et al. Identification of errors introduced during high throughput sequencing of the T cell receptor repertoire. BMC Genomics. Feb. 11, 2011;12:106.
Notification of Grant dated Jul. 26, 2011 for patent serial No. GB 2467704.
Novak, et al. Single-cell multiplex gene detection and sequencing With microfluidically generated agarose emulsions. Angewandte Chernie. 2011; 50: 390-395, with supplemental material.
Office action dated Mar. 13, 2013 for U.S. Appl. No. 13/763,978.
Office action dated Mar. 20, 2013 for U.S. Appl. No. 13/487,980.
Office action dated Apr. 22, 2013 for U.S. Appl. No. 13/214,1110.
Office action dated May 9, 2012 for U.S. Appl. No. 13/100,395.
Office action dated Sep. 15, 2011 for U.S. Appl. No. 12/615,263.
Office action dated Dec. 6, 2012 for U.S. Appl. No. 13/100,395.
Ogle, et al. Direst measurement of lymphocyte receptor diversity. Nucleic Acids Research. 2003; 31(22):e139.
Okajima et al., "Analysis of T cell receptor Vβ diversity in peripheral CD4+ and CD8+ T lymphocytes in patients with autoimmune thyroid diseases," Clin Exp Immunol 155:166-172 (2008).
Packer et al., "Optimized clonotypic analysis of T-cell receptor repertoire in immune reconstitution," Exp. Hematol 35(3):516-521 (2007).
Panzer-Grumayer, et al. Immunogenotype changes prevail in relapses of young children with TEL-AML1-positive acute lymphoblastic leukemia and derive mainly from clonal selection. Clin Cancer Res. Nov. 1, 2005;11(21):7720-7.
Pels, et al. Clonal evolution as pathogenetic machanism in relapse of primary CNS lymphoma. Neurology. Jul. 13, 2004;63(1):167-9.
Pira, et al. Human naive CD4 T-cell clones specific for HIV envelope persist for years in vivo in the absence of antigenic challenge. J Acquir Immune Defic Syndr. Oct. 1, 2005;40(2):132-9.
Pop, et al. Bioinformatics challenges of new sequencing technology. Trends Genet. Mar. 2008;24(3):142-9.
Ray, et at. Single cell multiplex PCR amplification of five dystrophin gene exons combined with gender determination. Molecular Human Reproduction. 2001; 7(5): 489-494.
Reddy, et al. Systems analysis of adaptive immunity by utilization of high-throughput technologies. Curr Opin Biotechnol. Aug. 2011;22(4):584-9. Epub May 12, 2011.
Reinartz, et al. Massively parallel signature sequencing (MPSS) as a tool for in-depth quantitative gene expression profiling in all organisms. Brief Funct Genomic Proteomic. Feb. 2002;1(1):95-104.
Ria, et al. Collagen-specific T-cell repertoire in blood and synovial fluid varies with disease activity in early rheumatoid arthritis. Arthritis Res Ther. 2008;10(6):R135. Epub Nov. 17, 2008.
Rickison, et al. Human cytotoxic T lymphocyte responses to Epstein-Barr virus infection. Annu Rev Immunol 1997;15:405-31.
Risitano et al., "In-vivo dominant immune responses in aplastic anaemia: molecular tracking of putatively pathogenetic T-cell clones by TCR β-CDR3 sequencing," Lancet 364:355-364 (2004).
Robins et al., "Comprehensive assessment of T-cell receptor beta-chain diversity in alphabeta T cells," Blood 114(19):4099-4107 (2009).
Robins, et al. Ultra-sensitive detection of rare T cell clones. Immunol Methods. Jan. 31, 2012;375(1-2):14-9. Epub Sep. 10, 2011.
Rosenquist, et al. Clonal evolution as judged by immunoglobulin heavy chain gene rearrangements in relapsing precursor-B acute lymphoblastic leukemia. Eur J Haematol. Sep. 1999;63(3):171-9.
Rougemont, et al. Probabilistic base calling of Solexa sequencing data. BMC Bioinformatics. 2008; 9:431.
Ryan, et al. Clonal evolution of lymphoblastoid cell lines. Lab Invest. Nov. 2006;86(11):1193-200. Epub Oct. 2, 2006.
Schaufelberger, et al. An uneven expression of T cell receptor V genes in the arterial wall and peripheral blood in giant cell arteritis. Inflammation. Dec. 2008;31(6):372-83.

Scholler, et al. Analysis of T cell receptor alpha beta variability in lymphocytes infiltrating melanoma primary tumours and metastatic lesions. Cancer Immunol Immunother. Oct. 1994;39(4):239-48.
Schwab et al., "CD8+ T-cell clones dominate brain infiltrates in Rasmussen encephalitis and persist in the periphery," Brain 132:1236-1246 (2009).
Sfanos, et al. Phenotypic analysis of prostate-infiltrating lymphocytes reveals TH17 and Treg skewing. Clin Cancer Res. Jun. 1, 2008;14(11):3254-61. doi: 10.1158/1078-0432.CCR-07-5164.
Shen, et al. Comparing platforms for C. elegans mutant identification using high-throughput whole-genome sequencing. PLoS One. 2008;3(12):e4012.
Sing, et al. A molecular comparison of T lymphocyte populations infiltrating the liver and circulating in the blood of patients with chronic hepatitis B: evidence for antigen-driven selection of a public complementarity-determining region 3 (CDR3) motif. Hepatology. May 2001;33(5):1288-98.
Skulina et al., "Multiple sclerosis: brain-infiltrating CD8+ T cells persist as clonal expansions in the cerebrospinal fluid and blood," PNAS 101(8):2428-2433 (2004).
Sramkova, et al. Detectable minimal residual disease before allogeneic hematopoietic stem cell transplantation predicts extremely poor prognosis in children with acute lymphoblastic leukemia. Pediatr Blood Cancer. Jan. 2007;48(1):93-100.
Steenbergen, et al. Distinct ongoing Ig heavy chain rearrangement processes in childhood B-precursor acute lymphoblastic leukemia. Blood. Jul. 15, 1993;82(2):581-9.
Steward, et al. A polymerase chain reaction study of the stability of Ig heavy-chain and T-cell receptor delta gene rearrangements between presentation and relapse of childhood B-lineage acute lymphoblastic leukemia. Blood. Mar. 1, 1994;83(5):1355-62.
Struyk, et al. T cell receptors in rheumatoid arthritis. Arthritis Rheum. May 1995;38(5):577-89.
Sumida et al., "T cell receptor repertoire of infiltrating T cells in lips of Sjögren's syndrome patients," J Clin Invest 89:681-685 (1992).
Sumida et al., "T cell receptor Vα repertoire of infiltrating T cells in labial salivary glands from patients with Sjögren's syndrome," J Rheumatol 21: 1655-1661 (1994).
Szczepanski, et al. Comparative analysis of Ig and TCR gene rearrangements at diagnosis and at relapse of childhood precursor-B-ALL provides improved strategies for selection of stable PCR targets for monitoring of minimal residual disease. Blood. Apr. 1, 2002;99(7):2315-23.
Szczepanski, et al. Why and how to quantify minimal residual disease in acute lymphoblastic leukemia? Leukemia. Apr. 2007;21(4):622-6. Epub Feb. 15, 2007.
Tackenberg et al., "Clonal expansions of CD4+ β helper T cells in autoimmune myasthenia gravis," Eur J Immunol 37:849-863 (2007).
Tajiri, et al. Cell-microarray analysis of antigen-specific B-cells: single cell analysis of antigen receptor expression and specificity. Cytometry Part A. 2007; 71A: 961-967.
Thornhill, et al. A comparison of different lysis buffers to assess allele dropout from single cells for preimplantation genetic diagnosis. Prenatal Diagnosis. 2001; 21: 490-497.
Tokimitsu, et al. Single lymphocyte analysis with a microwell array chip. Cytometry. 2007; Part A, 71A: 1003-1010.
UK combined search and examination report dated Mar. 20, 2013 for GB 1300533.5.
UK Combined Search Report and Office action dated Jun. 29, 2012 for UK application No. GB1209668.1.
UK Combined Search Report and Office action dated May 26, 2011 for UK application No. GB1105068.9.
UK office action dated May 25, 2011 for UK application No. GB1009641.0.
UK office action dated Oct. 20, 2010 for UK application No. GB1009641.0.
UK Search Report and office action dated Jan. 12, 2012 for UK application No. GB1120209.0.
UK Search Report and office action dated Jul. 7, 2010 for UK application No. GB1009641.0.
Umibe et al., "Clonal expansion of T cells infiltrating in the airways of non-atopic asthmatics," Clin Exp Immunol 119:390-397 (2000).

(56) References Cited

OTHER PUBLICATIONS

Van Der Velden, et al. Analysis of minimal residual disease by Ig/TCR gene rearrangements: guidelines for interpretation of real-time quantitative PCR data. Leukemia. Apr. 2007;21(4):604-11. Epub Feb. 8, 2007.
Van Der Velden, et al. Detection of minimal residual disease in hematologic malignancies by real-time quantitative PCR: principles, approaches, and laboratory aspects. Leukemia. Jun. 2003;17(6):1013-34.
Van Dongen, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. Dec. 2003;17(12):2257-317.
Wang, et al. High throughput sequencing reveals a complex pattern of dynamic interrelationships among human T cell subsets. Proc Natl Acad Sci U S A. Jan. 26, 2010; 107(4): 1518-1523.
Wang, et al. Quantitative measurement of pathogen-specific human memory T cell repertoire diversity using a CDR3 beta-specific microarray. BMC Genomics. Sep. 19, 2007;8:329.
Warren et al., "Profiling model T-cell metagenomes with short reads," Bioinformatics 25(4):458-464 (2009).
Warren, et al. Exhaustive T-cell repertoire sequencing of human peripheral blood samples reveals signatures of antigen selection and a directly measured repertoire size of at least 1 million clonotypes. Genome Res. Feb. 24, 2011. [Epub ahead of print].
Weinstein et al., "High-throughput sequencing of the zebrafish antibody repertoire," Science 324:807-810 (2009).
Wells, et al. Strategies for preimplantation genetic diagnosis of single gene disorders by DNA amplification. Prenatal Diagnosis. 1998; 18: 1389-1401.
Wetmur, et al. An emulsion polymerase chain reaction-based method for molecular haplotyping. Methods in Molecular Biology. 1996; 410: 351-361.
Wetmur, et al. Linking emulsion PCR haplotype analysis. chapter 11, in Park (editor), PCR Protocols, Methods En Molecular Biology. 2011; 687: 165-175.
Wetmur, et al. Molecular haplotyping by linking emulsion PCR: analysis of paraoxonase 1 haplotypes and phenotypes. Nucleic Acids Research. 2005; 33(8):2615-2619.
Wlodarski, et al. Molecular strategies for detection and quantitation of the clonal cytotoxic T-cell responses in aplastic anemia and myelodysplastic syndrome. Blood. 2006; 108:2632-2641.
Wlodarski, et al. Pathologic clonal cytotoxic T-cell responses: nonrandom nature of the T-cell-receptor restriction in large granular lymphocyte leukemia. Blood. 2005; 106:2769-2779.
Wu, et al. High-throughput sequencing detects minimal residual disease in acute T lymphoblastic leukemia. Sci Transl Med. May 16, 2012;4(134):134ra63. doi:10.1126/scitranslmed.3003656.
Yin et al., "Antiretroviral therapy restores diversity in the T-cell receptor Vβ repertoire of CD4 T-cell subpopulations among human immunodeficiency virus type 1-infected children and adolescents," Clin Vac Immunol 16(9):1293-1301 (2009).
Yon, et al. Precise gene fusion by PCR. Nucleic Acids Research. 1989; 17(12):4895.
Zaliova, et al. Quantification of fusion transcript reveals a subgroup with distinct biological properties and predicts relapse in BCR/ABL-positive ALL: implications for residual disease monitoring. Leukemia. May 2009;23(5):944-51. Epub Jan. 22, 2009.
Zeng, et al. High-performance single cell genetic analysis using microfluidic emulsion generator arrays. Anal. Chem. 2010; 82:3183-3190.
Zhou, et al. High throughput analysis of TCR-beta rearrangement and gene expression in single cells. 2006; 86:314-321.
Han, et al, Immunorepertoire analysis by multiplex PCR amplification and high throughput sequencing, J. of Immunol., vol. 182, Apr. 15, 2009, Abstract.

Wang, et al. Immunorepertoire analysis by multiplex PCR amplification and high throughput sequencing. Poster-Program 42.6, The 96th Annual Meeting of the America Association of Immunologists, Seattle, USA. May 8-12, 2009.
U.S. Appl. No. 14/436,851, filed Apr. 17, 2015, Klinger et al.
U.S. Appl. No. 14/436,855, filed Apr. 17, 2015, Carlton et al.
U.S. Appl. No. 14/437,470, filed Apr. 21, 2015, Faham.
U.S. Appl. No. 14/611,878, filed Feb. 2, 2015, Moorhead et al.
U.S. Appl. No. 14/640,145, filed Mar. 6, 2015, Robins et al.
US 8,642,750, 02/2014, Robins et al. (withdrawn).
Akatsuka, et al. Rapid screening of T-cell receptor (TCR) variable gene usage by multiplex PCR: application for assessment of clonal composition. Tissue Antigens. Feb. 1999;53(2):122-34.
Alexandre, D., et al. "*H. sapiens* rearranged T-cell receptor gamma chain gene, V3RS-J1 (hybrid joint)," GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.
Alexandre, D., et al. "*H. sapiens* rearranged T-cell receptor gamma chain gene, V2-JP1," GenBank accession No. X57737, NCBI, Nov. 14, 2006, 8 pages [online] [retrieved on Jun. 26, 2013] Retrieved from the internet <URL:http://www.ncbi.nlm.nih.gov/nuccore/x57737>.
Al-Lazikani, et al. Standard conformations for the canonical structures of immunoglobulins. J Mol Biol. Nov. 7, 1997;273(4):927-48.
Bahloul, et al. Clinical impact of molecular diagnostics in low-grade lymphoma. Best Pract Res Clin Haematol. Mar. 2005;18(1):97-111.
Bernardin, et al. Estimate of the total number of CD8+ clonal expansions in healthy adults using a new DNA heteroduplex-tracking assay for CDR3 repertoire analysis. J Immunol Methods. Mar. 1, 2003;274(1-2):159-75.
Berquam-Vrieze, et al. Cell of origin strongly influences genetic selection in a mouse model of T-ALL. Blood. Oct. 27, 2011;118(17);4646-56. doi: 10.1182/blood-2011-03-343947. Epub Aug. 9, 2011.
Blow. PCR's next frontier. Nature Methods. Oct. 2007; 4(10):869-875.
Bolotin, et al. Next generation sequencing for TCR repertoire profiling: platform-specific features and correction algorithms. Eur J Immunol. Nov. 2012;42(11):3073-83. doi: 10.1002/eji.201242517. Epub Sep. 24, 2012.
Bradfield, et al. Graft-versus-leukemia effect in acute lymphoblastic leukemia: the importance of tumor burden and early detection. Leukemia. Jun. 2004;18(6):1156-8.
Brenan, et al. High throughput, nanoliter quantitative PCR. Drug Discov Today Technol. 2005 Autumn;2(3):247-53. doi: 10.1016/j.ddtec.2005.08.017.
Brentjens, et al. CD19-targeted T cells rapidly induce molecular remissions in adults with chemotherapy-refractory acute lymphoblastic leukemia. Sci Transl Med. Mar. 20, 2013;5(177):177ra38. doi: 10.1126/scitranslmed.3005930.
Buck, et al. Design strategies and performance of custom DNA sequencing primers. Biotechniques. Sep. 1999;27(3):528-36.
Campana. Progress of minimal residual disease studies in childhood acute leukemia. Curr Hematol Malig Rep. Jul. 2010;5(3):169-76. doi: 10.1007/s11899-010-0056-8.
Caporaso, et al. Global paterns of 16S rRNA diversity at a depth of millions of sequence per sample. Proc Natl Acad Sci U S A. Mar. 15, 2011;108 Suppl 1:4516-22. doi: 10.1073/pnas.1000080107. Epub Jun. 3, 2010.
Carlson, et al. Apr. 2011. Profiling the repertoire of TCRB usage in induced and natural Treg cells. J Immunol. 186: 62.5 (Abstr).
Carlson, et al. Immune Profiling Suggests an IGH Signaling-Dependent Subtype of Aggressive B-ALL. Blood. Presented Dec. 8, 2012. 120:1428 (Abstr). https://ash.confex.com/ash/2012/webprogram/Paper54654.html.
Carlson, et al. Deep sequencing of the human TCRγ and TCRβ repertoires provides evidence that TCRβ rearranges after αβ, γδ T cell commitment. Presented at the ASHG 2011 Conference. Oct. 2011. Poster.
Cave, et al. Clinical significance of minimal residual disease in childhood acute lymphoblastic leukemia. European Organization for Research and Treatment of Cancer—Childhood Leukemia Cooperative Group. N Engl J Med. Aug. 27, 1998;339(9):591-8.

(56) References Cited

OTHER PUBLICATIONS

Chothia, et al. Canonical structures for the hypervariable regions of immunoglobulins. J Mol Biol. Aug. 20, 1987;196(4):901-17.
Chothia, et al. Conformations of immunoglobulin hypervariable regions. Nature Dec. 21-28, 1989;342(6252):877-83.
Ciudad, et al. Detection of abnormalities in B-cell differentiation pattern is a useful tool to predict relapse in precursor-B-ALL. Br J Haematol. Mar. 1999;104(4):695-705.
Coustan-Smith, et al. Clinical importance of minimal residual disease in childhood acute lymphoblastic leukemia. Blood. Oct. 15, 2000;96(8):2691-6.
Coustan-Smith, et al. Early T-cell precursor leukaemia: a subtype of very high-risk acute lymphoblastic leukaemia. Lancet Oncol. Feb. 2009;10(2):147-56. doi: 10.1016/S1470-2045(08)70314-0. Epub Jan. 13, 2009.
Coustan-Smith, et al. Prognostic importance of measuring early clearance of leukemic cells by flow cytometry in childhood acute lymphoblastic leukemia. Blood. Jul. 1, 2002;100(1):52-8.
Curran-Everett. Multiple comparisons: philosophies and illustrations. Am J Physiol Regul Integr Comp Physiol. Jul. 2000;279(1):R1-8.
Dash, et al. Paired analysis of TCRα and TCRβ chains at the single-cell level in mice. J Clin Invest. Jan. 2011;121(1):288-95. doi: 10.1172/JCI44752. Epub Dec. 6, 2010.
De Jonge, et al. Evidence based selection of housekeeping genes. PLoS One. Sep. 19, 2007;2(9):e898.
Delaney, et al. Evolution and Clinical Implications of the T cell Repertoire Following Cord Blood Transplant. Biology of Blood and Marrow Transplant, vol. 19, Issue 2, S201-S202. Published Feb. 2013.
Denucci, et al. Integrin function in T-cell homing to lymphoid and nonlymphoid sites: getting there and staying there. Crit Rev Immunol. Sep. 2009;29(2):87-109.
Desmarais, et al. 2012. High-throughput sequencing of memory and naïve T cell receptor repertoires at the RNA and DNA levels reveals differences in relative expression of expanded TCR clones. The Journal of Immunology, May 2012, 188, 178.12.
Desmarais, et al. Deep profiling of the mouse TCRβ CDR3 region in thymus and spleen. Oct. 2010. Poster.
Desmarais, et al. High-throughput sequencing of memory and naïve T cell receptor repertoires at the RNA and DNA levels reveals differences in relative expression of expanded TCR clones. Apadtive Technologies. Seattle WA. Poster, 1 page. Presented May 5, 2012.
Dheda, et al. Validation of housekeeping genes for normalizing RNA expression in real-time PCR. Biotechniques. Jul. 2004;37(1):112-4, 116, 118-9.
Dik, et al. New insights on human T cell development by quantitative T cell receptor gene rearrangement studies and gene expression profiling. J Exp Med. Jun. 6, 2005;201(11):1715-23. Epub May 31, 2005.
Dobosy, et al. RNase H-dependent PCR (rhPCR): improved specificity and single nucleotide polymorphism detection using blocked cleavable primers. BMC Biotechnology. Aug. 10, 2011; 11(80):1-18.
Droese, et al. Validation of BIOMED-2 multiplex PCR tubes for detection of TCRB gene rearrangements in T-cell malignancies. Leukemia. Sep. 2004;18(9):1531-8.
Duby, et al. Human T-cell receptor aberrantly rearranged beta-chain J1.5-Dx-J2.1 gene. Proc. Natl. Acad. Sci. USA (1986) GenBank accession No. M13574.1, bases 1 to 100.
Edwards, et al. Multiplex PCR: advantages, development, and applications. PCR Methods Appl. Feb. 1994;3(4):S65-75.
Elnifro, et al. Multiplex PCR: optimization and application in diagnostic virology. Clin Microbiol Rev. Oct. 2000;13(4):559-70.
Emerson, et al. CD4+ and CD8+ T cell β antigen receptors have different and predictable V and J gene usage and CDR3 lengths. Presented at the Annual Meeting of The American Association of Immunologists 2012 in Boston, MA May 2012. Poster.
Emerson, et al. Correlation of TCR diversity with immune reconstitution after cord blood transplant. Presented at the American Society of Clinical Oncology's annual meeting. May 2012. Poster.
Emerson, et al. Estimating the ratio of CD4+ to CD8+ T cells using high-throughput sequence data. J Immunol Methods. May 31, 2013;391(1-2):14-21. doi: 10.1016/j.jim.2013.02.002. Epub Feb. 18, 2013.
European search report and opinion dated May 29, 2012 for EP Application No. 10732172.1.
Flohr, et al. Minimal residual disease-directed risk stratification using real-time quantitative PCR analysis of immunoglobulin and T-cell receptor gene rearrangements in the international multicenter trial AIEOP-BFM ALL 2000 for childhood acute lymphoblastic leukemia. Leukemia. Apr. 2008;22(4):771-82. doi: 10.1038/leu.2008.5. Epub Jan. 31, 2008.
Giannoni, et al. Allelic exclusion and peripheral reconstitution by TCR transgenic T cells arising from transduced human hematopoietic stem/progenitor cells. Mol Ther. May 2013;21(5):1044-54. doi: 10.1038/mt.2013.8. Epub Feb. 5, 2013.
Gonzalez, et al. Trafficking of B cell antigen in lymph nodes. Annu Rev Immunol. 2011;29:215-33. doi: 10.1146/annurev-immunol-031210-101255. Epub Dec. 21, 2010.
Grupp, et al. Adoptive transfer of autologous T cells improves T-cell repertoire diversity and long-term B-cell function in pediatric patients with neuroblastoma. Clin Cancer Res. Dec. 15, 2012;18(24):6732-41. doi: 10.1158/1078-0432.CCR-12-1432. Epub Oct. 23, 2012.
Grupp, et al. Chimeric antigen receptor-modified T cells for acute lymphoid leukemia. N Engl J Med. Apr. 18, 2013;368(16):1509-18. doi: 10.1056/NEJMoa1215134. Epub Mar. 25, 2013.
Henegariu, et al. Multiplex PCR: critical parameters and step-by-step protocol. Biotechniques. Sep. 1997;23(3):504-11.
Hwang, et al. Identification of a commonly used CDR3 region of infiltrating T cells expressing Vbeta13 and Vbeta15 derived from psoriasis patients. J Invest Dermatol. Mar. 2003;120(3):359-64.
International Preliminary Report on Patentability dated Apr. 24, 2014 for PCT/US2013/040221.
Kalinina, et al. Nanoliter scale PCR with TaqMan detection. Nucleic Acids Res. May 15, 1997;25(10):1999-2004.
Kalos, et al. T cells with chimeric antigen receptors have potent antitumor effects and can establish memory in patients with advanced leukemia. Sci. Transl Med. Aug. 10, 2011;3(95):95ra73. doi: 10.1126/scitranslmed.3002842.
Kanda, et al. Immune recovery in adult patients after myeloablative dual umbilical cord blood, matched sibling, and matched unrelated donor hematopoietic cell transplantation. Biol Blood Marrow Transplant. Nov. 2012;18(11):1664-1676.e1. doi: 10.1016/j.bbmt.2012.06.005. Epub Jun. 12, 2012.
Kaplinski, et al. MultiPLX Automatic Grouping and Evaluation of PCR Primers. in Methods in Molecular Biology, vol. 402: PCR Primer Design, Nov. 25, 2004, pp. 287-303.
Katz, et al. T cell infiltrate predicts long-term survival following resection of colorectal cancer liver metastases. Ann Surg Oncol. Sep. 2009;16(9):2524-30. doi: 10.1245/s10434-009-0585-3. Epub Jul. 1, 2009.
Kehrl, et al. Chemoattract receptor signaling and its role in lymphocyte motility and trafficking. Curr Top Microbiol Immunol. May 2009;334:107-27. doi: 10.1007/978-3-540-93864-4_5.
Kiianitsa, et al., "Development of Tools for T-Cell Repertoire Analysis (TCRB Spectratyping) for the Canine Model of Hematopoietic Cell Transplantation", Blood, ASH—Annual Meeting Abstracts, Nov. 2007, 110(11), Abstract 4873.
Ladanyi, et al. Prognostic impact of B-cell density in cutaneous melanoma. Cancer Immunol Immunother. Dec. 2011;60(12):1729-38. doi: 10.1007/s00262-011-1071-x. Epub Jul. 21, 2011.
Ladetto, et al. Real-time polymerase chain reaction in multiple myeloma: quantitative analysis of tumor contamination of stem cell harvests. Exp Hematol. Jun. 2002;30(6):529-36.
Ladetto, et al. Real-Time polymerase chain reaction of immunoglobulin rearrangements for quantitative evaluation of minimal residual disease in multiple myeloma. Biol Blood Marrow Transplant. 2000;6(3):241-53.
Larimore, et al. Shaping of human germline IgH repertoires revealed by deep sequencing. J Immunol. Sep. 15, 2012;189(6):3221-30. doi: 10.4049/jimmunol.1201303. Epub Aug. 3, 2012.

(56) References Cited

OTHER PUBLICATIONS

Lucio, et al. Flow cytometric analysis of normal B cell differentiation: a frame of reference for the detection of minimal residual disease in precursor-B-ALL. Leukemia. Mar. 1999;13(3):419-27.
Marelli-Berg, et al. Memory T-cell trafficking: new directions for busy commuters. Immunology. Jun. 2010;130(2):158-65. doi: 10.1111/j.1365-2567.2010.03278.x. Epub Apr. 12, 2010.
Mariani, et al. Comprehensive assessment of the TCRBV repertoire in small T-cell samples by means of an improved and convenient multiplex PCR method. Exp Hematol. Jun. 2009;37(6):728-38. doi: 10.1016/j.exphem.2009.03.003.
Markoulatos, et al. Multiplex polymerase chain reaction: a practical approach. J Clin Lab Anal. 2002;16(1):47-51.
Maryanski, et al. A quantitative, single-cell PCR analysis of an antigen-specific TCR repertoire selected during an in vivo CD8 response: direct evidence for a wide range of clone sizes with uniform tissue distribution. Mol Immunol. Aug. 1999;36(11-12):745-53.
Maslanka, et al. Molecular analysis of T cell repertoires. Spectratypes generates by multiplex polymerase chain reaction and evaluated by radioactivity or fluorescence. Hum Immunol. Sep. 1995;44(1):28-34.
McGoldrick, et al. Cytomegalovirus-specific T cells are primed early after cord blood transplant but fail to control virus in vivo. Blood. Apr. 4, 2013;121(14):2796-803. doi: 10.1182/blood-2012-09-453720. Epub Feb. 14, 2013.
Meier, et al. Fractal organization of the human T cell repertoire in health and after stem cell transplantation. Biol Blood Marrow Transplant. Mar. 2013;19(3):366-77. doi: 10.1016/j.bbmt.2012.12.004. Epub Jan. 11, 2013.
Merriam-Webster (attached; definition of "e.g.," accessed Apr. 25, 2014) http://www.merriam-webster.com/dictionary/e.g.
Merriam-Webster (attached; definition of "substantial," accessed Apr. 25, 2014) http://www.merriam-webster.com/dictionary/substantial.
Mittelstadl, et al. Thymocyte responsiveness to endogenous glucocorticoids is required for immunological fitness. J Clin Invest. Jul. 2012;122(7):2384-94. doi: 10.1172/JCI63067. Epub Jun. 1, 2012.
Monod, et al. IMGT/JunctionAnalysis: the first tool for the analysis of the immunoglobulin and T cell receptor complex V-J and V-D-J Junctions. Bioinformatics. Aug. 4, 2004;20 Suppl 1:i379-85.
Murugan, et al. Statistical inference of the generation probability of T-cell receptors from sequence repertoires. Proc. Natl Acad Sci U S A. Oct. 2, 2012;109(40):16161-6. doi: 10.1073/pnas.1212755109. Epub Sep. 17, 2012.
NCBI Accession No. L36092 "*Homo sapiens* germline beta T-cell receptor locus," NCBI, Jun. 26, 2009, 254 Pages, can be retrieved at <URL:http://www.ncbi.nlm.nih.gov/nuccore/L36092>.
Neller, et al. High frequency of herpesvirus-specific clonotypes in the human T cell repertoire can remain stable over decades with minimal turnover. J Virol. Jan. 2013;87(1):697-700. doi: 10.1128/JVI.02180-12. Epub Oct. 17, 2012.
Nicot, et al. Housekeeping gene selection for real-time RT-PCR normalization in potato during biotic and abiotic stress. J Exp Bot. Nov. 2005;56(421):2907-14. Epub Sep. 27, 2005.
Nolan, et al. Quantification of mRNA using real-time RT-PCR. Nat Protoc. 2006;1(3):1559-82.
Notice of allowance dated Feb. 17, 2015 for U.S. Appl. No. 12/425,310.
Notice of allowance dated Oct. 10, 2013 for U.S. Appl. No. 12/794,507.
Office action dated Jan. 16, 2014 for U.S. Appl. No. 13/656,265.
Office action dated Feb. 27, 2015 for U.S. Appl. No. 14/075,075.
Office action dated Apr. 4, 2014 for U.S. Appl. No. 12/794,507.
Office action dated Apr. 10, 2015 for U.S. Appl. No. 13/214,111.
Office action dated Apr. 17, 2015 for U.S. Appl. No. 13/459,701.
Office action dated Apr. 26, 2013 for U.S. Appl. No. 12/794,507.
Office action dated May 16, 2014 for U.S. Appl. No. 14/183,163.
Office action dated Jun. 6, 2014 for U.S. Appl. No. 14/183,177.
Office action dated Jun. 16, 2014 for U.S. Appl. No. 14/252,189.
Office action dated Jul. 10, 2013 for U.S. Appl. No. 13/217,126.
Office action dated Jul. 10, 2014 for U.S. Appl. No. 12/794,507.
Office action dated Jul. 11, 2014 for U.S. Appl. No. 13/217,126.
Office action dated Jul. 18, 2014 for U.S. Appl. No. 13/656,265.
Office action dated Oct. 1, 2014 for U.S. Appl. No. 14/183,177.
Office action dated Oct. 2, 2014 for U.S. Appl. No. 14/183,163.
Office action dated Oct. 9, 2014 for U.S. Appl. No. 14/252,189.
Office action dated Nov. 7, 2012 for U.S. Appl. No. 12/794,507.
Office action dated Dec. 2, 2014 for U.S. Appl. No. 14/095,629.
Office action for Australian Patent Application No. 2010263172, Jul. 9, 2014, 4 Pages.
Office Action for Canadian Patent Application No. 2,765,949, Mailed Apr. 3, 2014, 4 Pages.
Office Action for Chinese Patent Application No. 201080028875.2, Mailed Feb. 13, 2014, 5 pages (With English Summary).
Office Action for European Patent Application No. EP 10722512.0, Dec. 17, 2012, 5 Pages.
Office Action for Israel Patent Application No. IL 217200, Jan. 21, 2013, 4 Pages.
Office action for Israel Patent Application No. IL 217200, Mar. 18, 2014, 8 Pages.
Office action for Korean Patent Application No. 10-2011-7030953, May 30, 2014, 5 Pages.
Office action for Russian Patent Application No. 2012101828/10(002474), Mar. 28, 2014, 5 Pages.
PCT International Search Report and Written Opinion for PCT/US2013/040221, Sep. 23, 2013, 16 Pages.
PCT International Search Report and Written Opinion, PCT Application No. PCT/US2010/021264, Apr. 14, 2010, 7 pages.
PCT International Search Report and Written Opinion, PCT/2013/045994, Oct. 25, 2013, 16 Pages.
PCT International Search Report and Written Opinion, PCT/US2010/037477, Sep. 24, 2010, 10 pages.
PCT International Search Report and Written Opinion, PCT/US2011/049012, Apr. 10, 2012, 9 Pages.
PCT International Search Report and Written Opinion, PCT/US2011/026373, Oct. 20, 2011, 14 Pages.
PCT International Search Report and Written Opinion, PCT/US2012/061193, Mar. 28, 2013, 12 Pages.
PCT International Search Report and Written Opinion, PCT/US2012/068617, Jun. 13, 2013, 8 Pages.
PCT International Search Report and Written Opinion, PCT/US2013/062925, Nov. 25, 2013, 12 Pages.
Pekin, et al. Quantitative and sensitive detection of rare mutations using droplet-based microfluidics. Lab Chip. Jul. 7, 2011;11(13):2156-66. doi: 10.1039/c11c20128j. Epub May 19, 2011.
Perkel. Overcoming the Challenges of Multiplex PCR. Biocompare Editorial Article, Oct. 23, 2012, 6 Pages, can be retrieved at URL:http://www.biocompare.com/Editorial-Articles/117895-Multiplex-PCR/>.
Pohl, et al. Principle and applications of digital PCR. Expert Rev Mol Diagn. Jan. 2004;4(1):41-7.
Porter, et al. Chimeric antigen receptor-modified T cells in chronic lymphoid leukemia. N Engl J Med. Aug. 25, 2011;365(8):725-33. doi: 10.1056/NEJMoa1103849. Epub Aug. 10, 2011.
Puisieux, et al. Oligoclonality of tumor-infiltrating lymphocytes from human melanomas. J Immunol. Sep. 15, 1994;153(6):2807-18.
Rasmussen, et al. Quantitation of minimal residual disease in multiple myeloma using an allele-specific real-time PCR assay. Exp Hematol. Sep. 2000;28(9):1039-45.
Reischl, et al. Quantitative PCR. A survey of the present technology. Mol Biotechnol. Feb. 1995;3(1):55-71.
Rieder, et al. A normalization procedure for removal of residual multiplex PCR amplification bias from ultra-deep sequencing of the TCR repertoire; (Program #530W). Presented at the 62nd Annual Meeting of the American Society of Human Genetics, Nov. 7, 2012 in San Francisco, California.
Rieder, et al. A normalization procedure for removal of residual multiplex PCR amplification bias from ultra-deep sequencing of the TCR repertoire. Presented at the Annual Meeting of the American Society of Hematology 2012 in Atlanta, Georgia Dec. 2012. Poster.

(56) References Cited

OTHER PUBLICATIONS

Robins, et al. May 2012. CD4+ and CD8+ T cell β antigen receptors have different and predictable V and J gene usage and CDR3 lengths. J Immunol. 188: 115.10 (Abstr).
Robins, et al. May 2012. Effects of aging on the human adaptive immune system revealed by high-throughput DNA sequencing of T cell receptors. J Immunol. 188:47.16 (Abstr).
Robins, et al. High-throughput sequencing of T-cell receptors. Sep. 2010. Poster.
Robins, et al. Immune profiling with high-throughput sequencing. Presented for the ASHI 2011 conference. Oct. 2011. Poster.
Robins, et al. Overlap and effective size of the human CD8+ T cell receptor repertoire. Sci Transl Med. Sep. 1, 2010;2(47):47ra64. doi: 10.1126/scitranslmed.3001442.
Robins, et al. Overlap of the human CD8+ T cell receptor repertoire. Oct. 2010. Poster.
Robins. Overlap and effective size of the human CD8+ T cell repertoire. Keystone Symposia held Oct. 27, 2010 to Nov. 1, 2010. Immunological Mechanisms of Vaccination (Abstract). Available online Sep. 27, 2010, 1 page.
Robins. Detecting and monitoring lymphoma with high-throughput sequencing. Oncotarget. Apr. 2011;2(4):287-8.
Rock, et al. CDR3 length in antigen-specific immune receptors. J Exp Med. Jan. 1, 1994;179(1):323-8.
Roshal, et al. Immaturity associated antigens are lost during induction for T cell lymphoblastic leukemia: implications for minimal residual disease detection. Cytometry B Clin Cytom. May 2010;78(3):139-46. doi: 10.1002/cyto.b.20511.
Rozen, et al. Primer3 on the WWW for general users and for biologist programmers. Methods Mol Biol. 2000;132:365-86.
Saada, et al. Models for antigen receptor gene rearrangement: CDR3 length. Immunol Cell Biol. Jun. 2007;85(4):323-32. Epub Apr. 3, 2007.
Santalucia. Physical principles and visual-OMP software for optimal PCR design Methods Mol Biol. Feb. 2007;402:3-34.
Santamaria, et al. Beta-cell-cytotoxic CD8+ T cells from nonobese diabetic mice use highly homologous T cell receptor alpha-chain CDR3 sequences. J Immunol. Mar. 1, 1995;154(5):2494-503.
Schrappe, et al. Late MRD response determines relapse risk overall and in subsets of childhood T-cell ALL: results of the AIEOP-BFM-ALL 2000 study. Blood. Aug. 25, 2011;118(8):2077-84. doi: 10.1182/blood-2011-03-338707. Epub Jun. 30, 2011.
Sherwood, et al. Deep sequencing of the human TCRγ and TCRβ repertoires suggests that TCRβ rearranges after αβ and γδ T cell commitment. Sci Transl Med. Jul. 6, 2011;3(90):90ra61. doi: 10.1126/scitranslmed.3002536.
Sherwood, et al. New Technologies for Measurements of Tumor Infiltrating Lymphocytes. Presented Nov. 7, 2012 Moscone Center, Exhibit Halls ABC.
Silver, et al. Selection of housekeeping genes for gene expression studies in human reticulocytes using real-time PCR. BMC Mol Biol. Oct. 6, 2006;7:33.
Sint, et al. Advances in multiplex PCR: balancing primer efficiencies and improving detection success. Methods Ecol Evol. Oct. 2012;3(5):898-905.
Srivastava, et al. Palindromic nucleotide analysis in human T cell receptor rearrangements. PLoS One. 2012;7(12):e52250. doi: 10.1371/journal.pone.0052250. Epub Dec. 21, 2012.
Standard Sequencing Primers, Max Planck Genome Center Cologne, Jan. 15, 2011, downloaded from https://genomecentre.mpipz.mpg.de/SeqOrderDB/export/sequencing-primers.html.
Stein, et al. Chemokine control of lymphocyte trafficking: a general overview. Immunology. Sep. 2005;116(1):1-12.
Steinmetz, et al. Chemokines and B cells in renal inflammation and allograft rejection. Frontiers in Bioscience (Schol. Ed.), Jun. 1, 2009, vol. 1, pp. 13-22.
Szczepanski, et al. Minimal residual disease in leukaemia patients. Lancet Oncol. Jul. 2001;2(7):409-17.
Tewhey, et al. Corrigendum: Microdroplet-based PCR enrichment for large-scale targeted sequencing. Nat Biotechnol. Feb. 2010;28(2):178.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Triebel, et al. A unique V-J-C-rearranged gene encodes a gamma protein expressed on the majority of CD3+ T cell receptor-alpha/beta- circulating lymphocytes. J Exp Med. Feb. 1, 1988;167(2):694-9.
Van Der Velden, et al. Optimization of PCT-based minimal residual disease diagnostics for childhood acute lymphoblastic leukemia in a multi-center setting. Leukemia. Apr. 2007;21(4):706-13. Epub Feb. 8, 2007.
Van Der Velden, et al. Real-Time quantitative PCR for detection of minimal residual disese before allogeneic stem cell transplantation predicts outcome in children with acute lymphoblastic leukemia. Leukemia. Sep. 2001;15(9):1485-7.
Van Dongen, et al. Prognostic value of minial residual disease in acute lymphoblastic leukaemia in childhood. Lancet. Nov. 28, 1998;352(9142):1731-8.
Venturi, et al. TCR beta-chain sharing in human CD8+ T cell responses to cytomegalovirus and EBV. J Immunol. Dec. 1, 2008;181(11):7853-62.
Venturi, et al. The molecular basis for public T-cell responses? Nat Rev Immunol. Mar. 2008;8(3):231-8. doi: 10.1038/nri2260.
Verhagen, et al. Application of germline IGH probes in real-time quantitative PCR for the detection of minimal residual disease in acute lymphoblastic leukemia. Leukemia. Aug. 2000;14(8):1426-35.
Vogelstein, et al. Digital PCR. Proc Natl Acad Sci U S A. Aug. 3, 1999;96(16):9236-41.
Ward, et al. Mechanisms of chemokine and antigen-dependent T-lymphocyte navigation. Biochem J. Feb. 15, 2009;418(1):13-27. doi: 10.1042/BJ20081969.
Wood. 9-color and 10-color flow cytometry in the clinical laboratory. Arch Pathol Lab Med. May 2006;130(5):680-90.
Wu, et al. Dec. 2011. High-throughput sequencing of T-cell receptor gene loci for minimal residual disease monitoring in T Lymphooblastic Leukemia. Blood. 118:2545 (Abstr).
Wu, et al. High-throughput sequencing detects minimal residual disease in acute T lymphoblastic leukemia. Sci Transl Med. May 16, 2012;4(134):134ra63. doi: 10.1126/scitranslmed.3003656.
Xu, et al. A novel universal primer-multiplex-PCR method with sequencing gel electrophoresis analysis. PLoS One. 2012;7(1):e22900. doi: 10.1371/journal.pone.0022900. Epub Jan. 17, 2012.
Zhong, et al. Multiplex digital PCR: breaking the one target per color barrier of quantitative PCR. Lab Chip. Jul. 7, 2011;11(13):2167-74. doi: 10.1039/c11c20126c. Epub May 17, 2011.
Office action dated Jul. 17, 2015 for U.S. Appl. No. 14/075,075.
Xu, et al. Simultaneous isolation of DNA and RNA from the same cell population obtained by laser capture microdissection for genome and transcriptome profiling. J Mol Diagn. Mar. 2008;10(2):129-34. doi: 10.2353/jmoldx.2008.070131. Epub Feb. 7, 2008.
Office action dated May 8, 2015 for U.S. Appl. No. 14/242,299.
Office action dated May 22, 2015 for U.S. Appl. No. 14/243,875.
Office action dated May 22, 2015 for U.S. Appl. No. 14/329,873.
Office action dated Jun. 4, 2015 for U.S. Appl. No. 13/908,813.
Office action dated Jun. 19, 2015 for U.S. Appl. No. 13/905,406.
Office Action dated Jul. 8, 2015 for U.S. Appl. No. 14/176,551.
Ladetto, et al., "Next-generation sequencing and real-time quantitative PCR for minimal residual disease (MRD) detection using the immunoglobulin heavy chain variable region: A methodical comparison in acute lymphoblastic leukemia (ALL), mantle cell lymphoma (MCL) and mulitple myeloma (MM)", *Blood*, vol. 120 , No. 21, Abstract 788 (Conference Abstract), Entire Abstract (2012).
PCT/US2013/043420, International Search Report and Written Opinion dated Oct. 25, 2013, 8 pages.
PCT/US2013/043420, International Preliminary Report on Patentability dated May 19, 2015, 7 pages.
U.S. Appl. No. 12/615,263, filed Nov. 9, 2011, Faham et al.
U.S. Appl. No. 13/100,365, filed May 4, 2011, Faham et al.
U.S. Appl. No. 13/100,389, filed May 4, 2011, Faham et al.

(56) References Cited

OTHER PUBLICATIONS

U.S. Appl. No. 13/100,395, filed May 4, 2011, Faham et al.
U.S. Appl. No. 13/214,111, filed Aug. 19, 2011, Faham et al.
U.S. Appl. No. 13/459,701, filed Apr. 30, 2012, Faham et al.
U.S. Appl. No. 13/468,323, filed May 10, 2012, Faham et al.
U.S. Appl. No. 13/596,581, filed Aug. 28, 2012, Zheng et al.
U.S. Appl. No. 13/688,414, filed Nov. 29, 2012, Faham et al.
U.S. Appl. No. 13/834,794, filed Mar. 15, 2013, Pepin et al.
U.S. Appl. No. 13/835,093, filed Mar. 15, 2013, Faham et al.
U.S. Appl. No. 13/859,210, filed Apr. 9, 2013, Asbury et al.
U.S. Appl. No. 14/089,517, filed Nov. 25, 2013, Han.
U.S. Appl. No. 14/185,846, filed Feb. 20, 2014, Pepin et al.
U.S. Appl. No. 14/197,615, filed Mar. 5, 2014, Carlton et al.
U.S. Appl. No. 14/202,990, filed Mar. 10, 2014, Zheng.
U.S. Appl. No. 14/242,520, filed Apr. 1, 2014, Klinger et al.
U.S. Appl. No. 14/343,286, filed Mar. 6, 2014, Faham et al.
European Search report and opinion dated Mar. 13, 2014 for EP Application No. 13195379.6.
European search report and opinion dated Jul. 26, 2013 for EP Application No. 11777704.5.
Greenberg, et al. Profile of immunoglobulin heavy chain variable gene repertoires and highly selective detection of malignant clonotypes in acute lymphoblastic leukemia. J Leukoc Biol. Jun. 1995;57(6):856-64.
International preliminary report on patentability dated May 19, 2011 for PCT/US2009/006053.
International search report and written opinion dated Aug. 19, 2013 for PCT/US2013/07258.
Li, et al. beta cell-specific CD4+ T cell clonotypes in peripheral blood and the pancreatic islets are distinct. J Immunol. Dec. 1, 2009;183(11):7585-91. doi: 10.4049/jimmunol.0901587. Epub Nov. 16, 2009.
Notice of allowance dated Jan. 27, 2014 for U.S. Appl. No. 13/100,365.
Notice of allowance dated Feb. 21, 2014 for U.S. Appl. No. 13/468,323.
Notice of allowance dated Mar. 14, 2012 for U.S. Appl. No. 12/615,263.
Notice of allowance dated Aug. 30, 2013 for U.S. Appl. No. 13/763,978.
Notice of allowance dated Nov. 6, 2013 for U.S. Appl. No. 13/100,389.
Notice of allowance dated Dec. 5, 2013 for U.S. Appl. No. 13/214,111.
Office action dated Apr. 4, 2014 for U.S. Appl. No. 13/459,701.
Thor Straten, et al. T-cell clonotypes in cancer. J Transl Med. Apr. 8, 2004;2(1):11.
Abbott, et al. "Design and use of signature primers to detect carry-over of amplified material", *J Virol Methods*, 46(1):51-59, Abstract only (1994).
Ahmadzadeh et al. "FOXP3 expression accurately defines the population of intratumoral regulatory T cells that selectively accumulate in metastatic melanoma lesions", *Blood*, 112(13): 4953-4960 (2008).
Altman, et al. "Phenotypic analysis of antigen-specific T lymphocytes", The *Journal of Immunology*, 187(1):7-9 (2011).
Altschul, et al. "Basic local alignment search tool", *J Mol Biol.*, 215(3):403-410 (1990).
Arden, et al. "Human T-cell receptor variable gene segment families", *Immunogenetics*, 42(6):455-500, Abstract Only (1995).
Armand, P. et al. "Detection of circulating tumour DNA in patients with aggressive B-cell non-Hodgkin lymphoma", *Brit. J. Haematol.*, vol. 163, pp. 123-126 (2013).
Aarts et al., "Variable heavy-chain gene analysis of follicular lymphomas: subclone selection rather than clonal evolution over time", Blood, 98(1): 238-240 (2001).
Aslandzadeh. "Preventing PCR amplification carryover contamination in a clinical laboratory", *Ann Clin Lab Sci.*, 34(4):389-396 (2004).
Assaf, et al. "High Detection Rate of T-Cell Receptor Beta Chain Rearrangements in T-Cell Lymphoproliferations by Family Specific Polymerase Chain Reaction in Combination with the Genescan Technique and DNA Sequencing", *Blood*, 96(2): 640-646 (2000).
Ateya, et al. "The good, the bad, and the tiny: a review of microflow cytometry", *Anal Bioanal Chem.*, 391(5): 1485-1498 (2008). doi: 10.1007/s00216-007-1827-5. Epub Jan. 29, 2008.
Babrzadeh et al. "Development on High-throughput Sequencing Technology: emPCR Titration and Barcode Design", *Stanford School of Medicine*, 2 pages (2011).
Bajor et al., "Immune activation and a 9-year ongoing complete remission following CD40 antibody therapy and metastasectomy in a patient with metastatic melanoma", Cancer Immunol Res., 2(11): 1051-1058 (2014).
Baldauf, "Phylogeny for the faint of heart: a tutorial," Trends in Genetics, 19(6): 345-351 (2003).
Barbas, et al. "Assembly of combinatorial antibody libraries on phage surfaces: the gene III site", *PNAS*, 88(18): 7978-7982, Abstract Only (1991).
Barker, et al. "A second type II restriction endonuclease from Thermus aquaticus with an unusual sequence specificity", *Nucleic Acids Res.*, 12(14): 5567-5581 (1984).
Baum and McCune et al. "Direct measurement of T-cell receptor repertoire diversity with AmpliCot", *Nat Methods*, 3(11): 895-901 (2006).
Becattini et al., "T cell immunity. Functional heterogeneity of human memory CD4+ cell clones primed by pathogens or vaccines", Science, 347(6220): 400-406 (2015).
Becker-Andréand Hahlbrock. "Absolute mRNA quantification using the polymerase chain reaction (PCR). A novel approach by a PCR aided transcript titration assay (PATTY)", *Nucleic Acids Res.*, 17(22): 9437-9446 (1989).
Becton-Dickinson, CD marker handbook. bdbiosciences.com/go/mousecdmarkers, p. 1-47 (2010).
Becton-Dickinson T-Cell Research Tools, "Novel multicolor flow cytometry tools for the study of CD4+ T-cell differentiation and plasticity", 16 pages (2009).
Ben-Erza, et al. Effect of fixation on the amplification of nucleic acids from paraffin-embedded material by the polymerase chain reaction, *The Journal of Histochemistry and Cytochemistry*, 39(3): 351-354 (1991).
Benecke. "DNA typing in forensic medicine and in criminal investigations: a current survey", *Naturwissenschaften*, 84(5): 181-188 (1997).
Benichou, J. et al., "The restricted DH gene reading frame usage in the expressed human antibody repertoire is selected based upon its amino acid content", J Immunol., 190(11): 5567-77, 29 pages (2013).
Bentley, et al. "Accurate whole human genome sequencing using reversible terminator chemistry", *Nature*, 456(7218) :53-59 (2008). doi: 10.1038/nature07517.
Bereczki, et al. "Optimization of PCR amplification for B- and T-cell clonality analysis on formalin-fixed and paraffin-embedded samples", *Pathology Oncology Research*, 13(3): 209-214 (2007). Epub Oct. 7, 2007.
Berger, et al. "The clonotypic T cell receptor is a source of tumor-associated antigens in cutaneous T cell lymphoma", *Annals of the New York Academy of Sciences*, 941:106-122, Abstract Only (2001).
Berget, et al. "Detection of clonality in follicular lymphoma using formalin-fixed, paraffin-embedded tissue samples and BIOMED-2 immunoglobulin primers", J Clin Pathol., 64(1):37-41 (2011). doi: 10.1136/jcp.2010.081109. Epub Oct. 28, 2010.
Berglund et al., "Genomic imbalances during transformation from follicular lymphoma to diffuse large B-cell lymphoma", Modern Pathology, 20(1): 63-75 (2007).
Bernard et al. "Color multiplexing hybridization probes using the apolipoprotein E locus as a model system for genotyping", Anal Biochem., 273(2):221-228 (1999).
Bettini et al., "Membrane association of the CD3ε signaling domain is required for optimal T cell development and function", J Immunol., 193(1): 258-267 (2014).
Berzofsky, et al. "Progress on new vaccine strategies for the immunotherapy and prevention of cancer", *J Clin Invest.*, 113(11): 1515-1525 (2004).

(56) References Cited

OTHER PUBLICATIONS

Biagi, et al. "Responses to human CD40 ligand/human interleukin-2 autologous cell vaccine in patients with B-cell chronic lymphocytic leukemia", *Clin Cancer Res.*, 11(19 Pt 1): 6916-6923 (2005).
Biggerstaff, et al. "Enumeration of leukocyte infiltration in solid tumors by confocal laser scanning microscopy", *BMC Immunol.*, 7:16, 13 pages (2006).
Brochet et al. "IMGT/V-QUEST: the highly customized and integrated system for IG and TR standardized V-J and V-D-J sequence analysis", *Nucleic Acids Research*, vol. 36, Web Server issue W503-W508 (2008).
Bonner et al. "Fluorescence activated cell sorting", Rev Sci Instrum., 43(3):404-409, Abstract Only (1972).
Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.
Boudinot et al. "New perspectives for large-scale repertoire analysis of immune receptors", *Molecular Immunology*, 45: 2437-2445 (2008).
Bousso. "Generation of MHC-peptide tetramers: a new opportunity for dissecting T-cell immune responses", Microbes Infect., 2(4):425-429, Abstract Only (2000).
Boyce, et al. "Human regulatory T-cell isolation and measurement of function", *BD Biosciences*, pp. 1-20 (2010).
Bravo and Irizarry. "Model-Based Quality Assessment and Base-Calling for Second-Generation Sequencing Data", Biometrics, 66(3): 665-674 (2010).
Brenner, et al. "In vitro cloning of complex mixtures of DNA on microbeads: physical separation of differentially expressed cDNAs", *PNAS*, 97(4): 1665-1670 (2000).
Brisco, et al. "Outcome prediction in childhood acute lymphoblastic leukaemia by molecular quantification of residual disease at the end of induction", *Lancet*, 343:196-200 (1994).
Brockman et al, "Quality scores and SNP detection in sequencing-by-synthesis systems," Genome Research, 18: 763-770 (2008).
Brody, et al. "Active and passive immunotherapy for lymphoma: proving principles and improving results", Clin Oncol., 29(14):1864-1875, Abstract Only (2011). doi: 10.1200/JCO.2010.33.4623. Epub Apr. 11, 2011.
Brody, et al., "Immunotransplant for mantle cell lymphoma: Phase I/II study preliminary results", *Journal of Clinical Oncology*, ASCO Annual Meeting Abstracts Part 1, vol. 29, No. 15, 1 page (2011).
Brody, et al. "Lymphoma immunotherapy: vaccines, adoptive cell transfer and immunotransplant", *Immunotherapy*, 1(5): 809-824 (2009). doi: 10.2217/imt.09.50.
Brown, et al. "Current techniques for single-cell lysis", *J. R. Soc. Interface*, 5:S131-S138 (2008).
Brownie et al. "The elimination of primer-dimer accumulation in PCR", Nucleic Acids Research, 25(16): 3235-3241 (1997).
Brüggemann, et al. "Rearranged T-cell receptor beta genes represent powerful targets for quantification of minimal residual disease in childhood and adult T-cell acute lymphoblastic leukemia", *Leukemia*, 18(4): 709-719 (2004).
Buccisano, et al. "Prognostic and therapeutic implications of minimal residual disease detection in acute myeloid leukemia", Blood, 119(2):332-341 (2012). doi: 10.1182/blood-2011-08-363291. Epub Oct. 28, 2011.
Buccisano, et al. "Monitoring of minimal residual disease in acute myeloid leukemia", Curr Opin Oncol., 21(6):582-588, Abstract Only (2009). doi: 10.1097/CCO.0b013e3283311856.
Butkus, B. "Hutch Team Uses ddPCR to Quantify T-Cell Response in Tumors; Adaptive Biotech Eyes Market", *PCR Insider*, Dec. 12, 2013, 3 pages http://www.genomeweb.com/print/1323296.
Bystrykh. "Generalized DNA Barcode Design Based on Hamming Codes", *PLoS ONE*, 7(5): e36852, 1-8 (2012).
Campana, et al. "Role of minimal residual disease monitoring in adult and pediatric acute lymphoblastic leukemia", *Hematol Oncol Clin North Am.*, 23(5): 1083-1098 (2009. doi: 10.1016/j.hoc.2009.07.010.

Carlotti, et al. "Transformation of follicular lymphoma to diffuse large B-cell lymphoma may occur by divergent evolution from a common progenitor cell or by direct evolution from the follicular lymphoma clone", *Blood*, 113(15): 3553-3557 (2009). doi: 10.1182/blood-2008-08-174839. Epub Feb. 6, 2009.
Carlson, et al. "Detection of tumor tagging clones in multiple myeloma via high throughput sequencing is robust to significant levels of SHM", Presented for the 2014 ASH Annual Meeting. Poster. 1 page. Dec. 5-9, 2014.
Carlson, C.S. et al. "Using synthetic templates to design an unbiased multiplex PCR assay", *Nature Communications*, 4:2680, pp. 1-9 (2013).
Casali, et al. "Human monoclonals from antigen-specific selection of B lymphocytes and transformation by EBV", *Science*, 234(4775): 476-479, Abstract Only (1986).
Casbon et al. "A method for counting PCR template molecules with application to next generation sequencing", *Nucleic Acids Research*, 39(12): e81, 8 pages (2011).
Catherwood, M.A. et al., "Improved clonality assessment in germinal centre/post germinal centre non-Hodgkin's lymphomas with high rates of somatic hypermutation", *J. Clin. Pathol.*, 60:524-528, Abstract (2007).
Chan et al. "Evaluation of Nonfluidics Technology for High-Throughput SNP Genotyping in a Clinical Setting", *The Journal of Molecular Diagnostics*, 13(3): 305-312 (2011).
Chattopadhyay, et al. "A live-cell assay to detect antigen-specific CD4+ T cells with diverse cytokine profiles", *Nat Med.*, 11(10): 1113-1117 (2005). Epub Sep. 25, 2005.
Chen et al. "Identification of racehorse and sample contamination by novel 24-plex STR system", Forensic Science International: Genetics, 4:158-167 (2010).
Chen, et al. "Microfluidic cell sorter with integrated piezoelectric actuator", *Biomed Microdevices*, 11(6): 1223-1231 (2009). doi: 10.1007/s10544-009-9341-5.
Chen, Y. et al., "T-cell receptor gene expression in tumour-infiltrating lymphocytes and peripheral blood lymphocytes of patients with nasopharyngeal carcinoma", *British Journal of Cancer*, 72(1): 117-22 (1995).
Chen, et al. "Total Gene Synthesis: Novel Single-Step and Convergent Strategies Applied to the Construction of a 779 Base Pair Bacteriorhodopsis", *Gene. J. Am. Chem Soc.*, 116: 8799-8800, Abstract Only (1994).
Chiu, et al. "Non-Invasive prenatal assessment of trisomy 21 by mutiplexed maternal plasma DNA sequencing: large scale validity study", *BMJ*, 342:c7401, 9 pages (2011). doi: 10.1136/bmj.c7401.
Churchill and Waterman. "The Accuracy of DNA Squences: Estimating Sequence Quality", *Genomics*, 14:89-98 (1992).
Chute, et al. "Detection of immunoglobulin heavy chain gene rearrangements in classic Hodgkin lymphoma using commercially available BIOMED-2 primers", *Diagn Mol Pathol.*, 17(2): 65-72 (2008). doi: 10.1097/PDM.0b013e318150d695.
Citri et al. "Comprehensive qPCR profiling of gene expression in single neuronal cells", *Nature Protocols*, 7(1): 118-127 (2012).
Cleary, et al. "Production of complex nucleic acid libraries using highly parallel in situ oligonucleotide synthesis", *Nat Methods*, 1(3): 241-248 (2004). Epub Nov. 18, 2004.
Clemente, et al. "Deep sequencing of the T-cell receptor repertoire in CD8+ T -large granular lymphocyte leukemia identifies signature landscapes", Blood, 122(25): 4077-85 (2013). doi: 10.1182/blood-2013-05-506386. Epub Oct. 22, 2013.
Conti et al. "Oral-resident natural Th17 cells and γδ T cells control opportunistic Candia albicans infections", J Exp Med., 2011(10): 2075-84 (2014). doi: 10.1084/jem.20130877. Epub Sep. 8, 2014.
Cooper, et al. "BRAF inhibition is associated with increased clonality in tumor infiltrating lymphocytes", Oncoimmunology, 2(10):e26615 (2013). Epub Oct. 15, 2013.
Craig et al. "Identification of genetic variants using bar-coded multiplex sequencing", *Nature Methods*, 5(10): 887-893 (2008) and Supplemental Materials.
Cronin, et al. "Comprehensive next-generation cancer genome sequencing in the era of targeted therapy and personalized oncology", *Biomark Med.*, 5(3):293-305 (2011). (Abstract only). doi: 10.2217/bmm.11.37.

(56) References Cited

OTHER PUBLICATIONS

Dahl et al. "Multiplex amplification enabled by selective circularization of large sets of genomic DNA fragments", Nucleic Acids Res., 33(8): e71 (2005).
Davi, et al. "Lymphocytic progenitor cell origin and clonal evolution of human B-lineage acute lymphoblastic leukemia", *Blood*, 88(2):609-621 (1996).
Davila, et al. Efficacy and toxicity management of 19-28z CART cell therapy in B cell acute lymphoblastic leukemia, Sci Transl Med., 6(224):224ra25 (2014). doi: 10.1126/scitranslmed.3008226.
Davis, et al. "Interrogating the repertoire: broadening the scope of peptide-MHC multimer analysis", *Nat Rev Immunol.*, 11(8):551-558 (2011). doi: 10.1038/nri3020.
de Haas et al., "Quantification of minimal residual disease in children with oligoclonal B-precursor acute lymphoblastic leukemia indicated that the clones that grow out during relapse already have the slowest rate of reduction during induction therapy", Leukemia, 15: 134-140 (2001).
Dean, et al. "Rapid amplification of plasmid and phage DNA using Phi 29 DNA polymerase and multiply-primed rolling circle amplification", *Genome Res.*, 11(16): 1095-1099 (2001).
Decoste et al. "Relative and Absolute Quantitative Real-Time PCR-Based Quantifications of hcnC and phlD Gene Transcripts in Natural Soil Spiked with Pseudomonas sp. Strain LBUM300", *Applied and Environmental Microbiology*, 77(1): 41-47 (2011).
Dedhia, et al. "Evaluation of DNA extraction methods and real time PCR optimization on formalin-fixed paraffin-embedded tissues" *Asian Pac J Cancer Prev.*, 8(1): 55-59 (2007).
Deiman, et al. "Characteristics and applications of nucleic acid sequence-based amplification (NASBA)", *Mol Biotechnol.*, 20(2): 163-179, Abstract Only (2002).
DeKosky et al. "High-throughput sequencing of the paired human immunoglobulin heavy and light chain repertoire", *Nature Biotechnology*, 31(2): 166-169 (2013).
Deschoolmeester, et al. "Tumor infiltrating lymphocytes: an intriguing player in the survival of colorectal cancer patients", *BMC Immunology*, 11:19, 12 pages (2010). doi: 10.1186/1471-2172-11-19.
Dictor et al. "Resolving T-cell receptor clonality in two and genotype in four multiplex polymerase chain reactions", *Haematologica*, 90(11): 1524-1532 (2005).
Diederichsen, et al. "Prognostic value of the CD4+/CD8+ ratio of tumour infiltrating lymphocytes in colorectal cancer and HLA-DR expression on tumour cells", *Cancer Immunol Immunother.*, 52(7):423-428 (2003). Epub Apr. 15, 2003.
Diehl, et al. "BeaMing: single-molecule PCR on microparticles in water-in-oil emulsions", *Nat Methods*, 3(7):551-559, Abstract Only (2006).
Ding, et al. "Clonal evolution in relapsed acute myeloid leukaemia revealed by whole-genome sequencing", *Nature*, 481(7382):506-510 (2012). doi: 10.1038/nature10738.
Diviacco, et al. "A novel procedure for quantitative polymerase chain reaction by coamplification of completitive templates", *Gene*, 122(2):313-320 (1992).
Do and Batzoglou. "What is the expectation maximization algorithm?", *Nature Biotechnology*, 26(8)L 897-899 (2008).
Drmanac, et al. "Human genome sequencing using unchained base reads on self-assembling DNA nanoarrays", *Science*, 327(5961):78-81 (2010). doi: 10.1126/science.1181498. Epub Nov. 5, 2009.
Dudgeon, et al. "The evolution of thymic lymphomas in p53 knockout mice", Genes Dev., 28(23): 2613-20 (2014). doi: 10.1101/gad. 252148.114.
Dunn, et al. "Focus on TILs: Prognostic significance of tumor infiltrating lymphocytes in human glimoa" *Cancer Immun.*, 7:12, 16 pages (2007).
Eason et al. "Characterization of synthetic DNA bar codes in *Saccharomyces cerevisiae* gene-deletion strains," PNAS, 101(30): 11046-11051 (2004).

Eichler, et al. "Haplotype and interspersion analysis of the FMR1 CGG repeat identifies two different mutational pathways for the origin of the fragile X syndrome", *Hum Mol Genet.*, 5(3):319-330 (1996).
Eichler, et al. "Length of uninterrupted CGG repeats determines instability in the FMR1 gene", *Nat Genet.*, 8(1):88-94, Abstract Only (1994).
Eid et al. "Real-time DNA sequencing from single polymerase molecules", *Science*, 323(5910):133-138 (2009). doi: 10.1126/science. 1162986. Epub Nov. 20, 2008.
Eis, et al. "An invasive cleavage assay for direct quantitation of specific RNAs", *Nat Biotechnol.*, 19(7):673-676, Abstract Only (2001).
Elhanati et al. "Quantifying selection in immune receptor repertoires", PNAS USA, 111(27): 9875-9880 (2014) doi: 10.1073/pnas. 149572111.
Elkord et al. "T regulatory cells in cancer: recent advances and therapeutic potential", *Expert Opinion On biological Therapy*, 10(11): 1573-1586 (2010).
Emerson et al. "Defining the Alloreactive T Cell Repertoire Using High-Through Sequencing of Mixed Lymphocyte Reaction Culture", *PLoS One*, 9(11): e111943 (2014).
Emerson, R.O. et al. "High-throughput sequencing of T-cell receptors reveals a homogeneous repertoire of tumour-infiltrating lymphocytes in overian cancer", *Journal of Pathology*, 231: 433-440 (2013).
Emerson, et al. TCR repertoire diversity assessed with immunosequencing is associated with patient mortality following cord blood transplant. Presented for the 2014 ASH Annual Meeting. Poster. 1 page. Dec. 5-9, 2014.
Estorninho, et al. "A novel approach to tracking antigen-experienced CD4 T cells into functional compartments via tandem deep and shallow TCR clonotyping", J Immunol., 191(11): 5430-40 (2013). doi: 10.4049/jimmunol.I300622. Epub Oct. 25, 2013.
EP Application No. 09764927.1, Notice of Opposition dated Oct. 14, 2014, Reference#547-7.
EP Application No. 09764927.1, Notice of Opposition dated Oct. 14, 2014, Reference#BR0-0001EP.
EP Application No. 09764927.1, European Opposition dated Oct. 15, 2014 (in French only).
Esendagli et al. "Malignant and non-malignant lung tissue areas are differentially populated by natural killer cells and regulatory T cells in non-small cell lung cancer", Lung Cancer, 59(1): 32-40 (2008).
European Patent Application No. 12856834.2, Extended European Search Report dated Jul. 7, 2015, 8 pages.
European Patent Application No. 12841014.9, Extended European Search Report dated May 4, 2015, 11 pages.
European Patent Application No. 12844825.5, Extended European Search Report dated Jun. 22, 2015, 6 pages.
European Patent Application No. 12859772.1, Extended European Search Report dated Sep. 2, 2015, 7 pages.
European Patent Application No. 12856615.8, Extended European Search Report dated Sep. 28, 2015, 7 pages.
European Patent Application No. 13804085.2, Extended European Search Report dated Nov. 16, 2015, 10 pages.
European Patent Application No. 13775514.6, Extended European Search Report dated Dec. 1, 2015, 12 pages.
European Patent Application No. 09764927.1, EPO's Communication of Notices of Opposition, dated Nov. 21, 2014.
European Patent Application No. 09764927.1, Patentee's Observations/Response dated May 27, 2015.
European Patent Application No. 09764927.1, Opponent's Response to Submission of the Patentee dated Nov. 23, 2015.
Ewing and Green, "Base-calling of automated sequencer traces using Phred. I. Accuracy Assessement," Genome Research, 8: 175-185 (1998).
Faham, M. et al. "Deep-sequencing approach for minimal residual disease detection in acute lymphoblastic leukemia", *Blood*, 120(26): 5173-5180 (2012).
Felsenstein, et al. "Evolutionary Trees from DNA Sequences: A Maximum Likelihood Approach", J Mol Evol, 17:368-376 (1981).
Ferradini et al. "Analysis of T Cell Receptor Variability in Tumor-infiltrating Lymphocytes from a Human Regressive Melanoma", *J. Clin. Invest.*, pp. 1183-190 (1993).

(56) References Cited

OTHER PUBLICATIONS

Ferrero, et al. "Multiple myeloma shows no intra-disease clustering of immunoglobulin heavy chain genes", *Haematologica*, 97(6): 849-853 (2012). doi: 10.3324/haematol.2011.052852. Epub Dec. 29, 2011.
Fisher et al. "The Relation Between the Number of Species and the Number of Individuals in a Random Sample of an Animal Population", *Journal of Animal Ecology*, 12(1): 42-58 (1943).
Flaherty et al. "Ultrasensitive detection of rare mutations using next-generation targeted resequencing", *Nucleic Acids Research*, 40(1): e2, 12 pages (2012).
Flicek and Birney, "Sense from sequence reads: methods for alignment and assembly," Nature Methods Supplement, 6(11s): S6-S12 (2009).
Frampton, et al. "Development and validation of a clinical cancer genomic profiling test based on massively parallel DNA sequencing", *Nat Biotechnol.*, 31(11): 1023-1031 (2013). doi: 10.1038/nbt.2696. Epub Oct. 20, 2013.
Frank. "BARCRAWL and BARTAB: software tools for the design and implementation of barcoded primers for highly multiplexed DNA sequencing," *BMC Bioinformatics*, 10: 362 (2009).
Frederiksson et al., "Multiplex amplification of all coding sequences with 10 cancer genes by Gene-Collector", Nucleic Acids Research, 35(7): e47 (2007).
Freeman, et al. "Quantitative RT-PCR: Pitfalls and Potential", *Biotechniques*, 6(1): 112-125 (1999).
Fridman, et al. "Prognostic and predictive impact of intra- and peritumoral immune infiltrates", *Cancer Research*, 71(17): 5601-5605 (2011). doi: 10.1158/0008-5472.CAN-11-1316. Epub Aug. 16, 2011.
Fu et al. "Counting individual DNA molecules by the stochastic attachment of diverse labels", *PNAS*, 108(22): 9026-9031 and Supporting Materials, 8 pages (2011).
Fuller, et al. "The challenges of sequencing by synthesis", *Nat Biotechnol.*, 7(11): 1013-23 (2009) (Abstract only). doi: 10.1038/nbt.1585. Epub Nov. 6, 2009.
Gauss, et al. "Mechanistic constraints on diversity in human V(D)J recombination", *Mol Cell Biol.*, 16(1):258-269 (1996).
Gawad, et al. "Massive evolution of the immunoglobulin heavy chain locus in children with B precursor acute lymphoblastic leukemia", *Blood*, 120(22):4407-4417 (2012). doi: 10.1182/blood-2012-05-429811. Epub Aug. 28, 2012.
Gerlinger, M. et al. "Ultra deep T cell receptor sequencing reveals the complexity and intratumour heterogeneity of T cell clones in renal cell carcinomas", *Journal of Pathology*, 231:424-432 (2013).
Gilbert, et al. "The isolation of nucleic acids from fixed, paraffin-embedded tissues-which methods are useful when?", *PLoS One*, 2(6):e537, 12 pages (2007).
Gloor et al. "Microbiome profiling by Illumina sequencing of combinatorial sequence-tagged PCR products," *PLoS ONE*, 5(10): e15406, 15 pages (2010).
Godelaine, et al. "Polyclonal CTL responses observed in melanoma patients vaccinated with dendritic cells pulsed with a MAGE-3.A1 peptide", *J Immunol.*, 171(9):4893-4897 (2003).
Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.
Gottenberg, et al. "Markers of B-lymphocyte activation are elevated in patients with early rheumatoid arthritis and correlated with disease activity in the ESPOIR cohort", *Arthritis Res Ther.*, 11(4): R114 (2009). doi: 10.1186/ar2773. Epub Jul. 23, 2009.
Gratama and Kern. "Flow cytometric enumeration of antigen-specific T lymphocytes", *Cytometry A*, 58(1): 79-86 (2004).
Gratama, et al. "Measuring antigen-specific immune responses", 2008 update. *Cytometry A.*, 73(11): 971-974 (2008). doi: 10.1002/cyto.a.20655.
Greenman, et al. "Patterns of somatic mutation in human cancer genomes", *Nature*, 446(7132): 153-158 (2007).
Gribben, JG. "Stem cell transplatation in chronic lymphocytic leukemia", *Biol. Blood Marrow Transplant.*, 15(1 Suppl): 53-58 (2009). doi: 10.1016/j.bbmt.2008.10.022.
Gulliksen, et al. "Real-time nucleic acid sequence-based amplification in nanoliter volumes", *Anal Chem.*, 76(1): 9-14, Abstract Only (2004).
Gunderson et al. "Decoding Randomly Ordered DNA Arrays", *Genome Research*, 14: 870-877 (2004).
Hadrup, et al. "Parallel detection of antigen-specific T-cell responses by multidimensional encoding of MHC multimers", *Nat. Methods*, 6(7): 520-526 (2009) (Abstract Only). doi: 10.1038/nmeth.1345. Epub Jun. 21, 2009.
Halldórsdóttir, et al. "Application of BIOMED-2 clonality assays to formalin-fixed paraffin embedded follicular lymphoma specimens: superior performance of the IGK assays compared to IGH for sub-optimal specimens", *Leukemia & Lymphoma*, 48(7): 1338-1343 (2007).
Hamady, et al. "Error-correcting barcoded primers for pyrosequencing hundreds of samples in multiplex", *Nature Methods*, 5(3):235-237 (2008). doi: 10.1038/nmeth.1184. Epub Feb. 10, 2008.
Han et al. "Immunorepertoire analysis by multiplex PCR amplification and high throughput sequencing", *The Journal of Immunology*, 182:42.6, 1 page (2009).
Hanahan, et al. "Hallmarks of cancer: the next generation", *Cell*, 144(5): 646-674 (2011). doi: 10.1016/j.cell.2011.02.013.
Harismendy et al. "Evaluation of next generation sequencing platforms for population targeted sequencing studies", *Genome Biology*, 10:R32, 13 pages (2009).
Harris et al. "Single-Molecule DNA Sequencing of a Viral Genome", *Science*, 320: 106-109 (2008).
Hathcock, et al. "ATM influences the efficiency of TCRβ rearrangement, subsequent TCRβ-dependent T cell development, and generation of the pre-selection TCRβ CDR3 repertoire", PLos One, 8(4):e62188 (2013). doi: 10.1371/journal.pone.0062188. Print 2013.
Hawkins, et al. "Whole genome amplification—applications and advances", *Curr Opin Biotechnol.*, 13(1): 65-67 (2002).
He, et al. "IgH gene rearrangements as plasma biomarkers in Non-Hodgekin's lymphoma patients", *Oncotarget*, 2(3): 178-185 (2011).
Heger, M. "Studies Highlight Challenges of Immune Repertoire Sequencing's Clinical Applicability", available at http://www.genomeweb.com/sequencing/studies-highlight-challenges-immune-repertoire-sequencings-clinical-applicabilit?hq_e=el&hq_m=966798&hq_l=10&hq_v=2357e2f0b3. Accessed Apr. 6, 2011.
Hensel et al. "Simultaneous identification of bacterial virulence genes by negative selection", *Science*, 269(5222): 400-403 (1995).
Hill, et al. "Using ecological diversity measures with bacterial communities", *FEMS Microbiol Ecol.*, 43(1):1-11 (2003). doi: 10.1111/j.1574-6941.2003.tb01040.x.
Hirohata, et al. "Regulation of human B cell function by sulfasalazine and its metabolites", *Int Immunopharmacol.*, 2(5): 631-640, Abstract Only (2002).
Hodges, E. et al. "Diagnostic role of tests for T cell receptor (TCR) genes", *J Clin Pathol.*, 56(1): 1-11 (2003).
Holder and Lewis. "Phylogeny estimation: traditional and bayesian approaches", Nat Rev Genet., 4(4): 275-84 (2009).
Holt and Jones. "The new paradigm of flow cell sequencing", *Genome Research*, 18:839-846 (2008).
Hoogenboom, et al. "Multi-subunit proteins on the surface of filamentous phage: methodologies for displaying antibody (Fab) heavy and light chains", *Nucleic Acids Res.*, 19(15): 4133-4137 (1991).
Hoogendoorn, et al. "Primary allogeneic T-cell responses against mantle cell lymphoma antigen-presenting cells for adoptive immunotherapy after stem cell transplantation", *Clin Cancer Res.*, 11(14):5310-5318 (2005).
Hoos, et al. "Improved endpoints for cancer immunotherapy trails", *J Natl Cancer Inst.*, 102(18): 1388-1397 (2010). doi: 10.1093/jnci/djq310. Epub Sep. 8, 2010.
Hoover and Lubkowski. "DNAWorks: an automated method for designing oligonucleotides for PCR-based gene synthesis", *Nucleic Acids Res.*, 30(10): e43, 7 pages (2002).
Hosono, et al. "Unbiased whole-genome amplification directly from clinical samples", *Genome Res.*, 13(5): 954-964 (2003). Epub Apr. 14, 2003.

(56) References Cited

OTHER PUBLICATIONS

Hoven, et al. "Detection and isolation of antigen-specific B cells by the fluorescence activated cell sorter (FACS)", *J Immunol Methods*, 117(2): 275-284, Abstract Only, 2 pages (1989).
Huang, et al. "Isolation of cell-free DNA from maternal plasma using manual and automated systems", *Methods Mol Biol.*, 444: 203-208, Abstract Only (2008). doi: 10.1007/978-1-59745-066-9_15.
Huh, et al. "Microfluidics for flow cytometric analysis of cells and particles", *Physiol Meas.*, 26(3): R73-98, Abstract Only (2005). Epub Feb. 1, 2005.
Huijsmans, et al. "Comparative analysis of four methods to extract DNA from paraffin-embedded tissues: effect on downstream molecular applications", *BMC Res Notes*, 3:239, 9 pages (2010). doi: 10.1186/1756-0500-3-239.
Huse, et al. "Generation of a large combinatorial library of the immunoglobulin repertoire in phage lambda", *Science*, 246(4935): 1275-1281, Abstract Only (1989).
Huse et al. "Accuracy and quality of massively parallel DNA pyrosequencing", *Genome Biology*, 8: R143 (2007).
Iancu, et al. "Profile of a serial killer: cellular and molecular approaches to study individual cytotoxic T-cells following therapeutic vaccination", *J Biomed Biotechnol.*, 2011:452606 (2011). doi: 10.1155/2011/452606. Epub Nov. 14, 2010.
Iijima et al. "A local macrophage chemokine network sustains protective tissue-resident memory CD4 T cells", Science, 346(6205): 93-8 (2014). doi: 10.1126/science.1257530. Epub Aug. 28, 2014.
Illumina. Genome analyzer pipeline software version 1.0 user guide. Part #1004759, 176 pages (2008).
Illumina. Data Sheet, "TruSeq™ exome enrichment kit", 5 pages (2011).
Illumina. "Technical Note: Systems and Software. Calling sequencing SNPs", 3 pages (2010).
Illumina. TruSeq Sample Preparation Kit and Data Sheet. Illumina, Inc., San Diego, CA 4 pages (2011).
Jabara et al. "Accurate sampling and deep sequencing of the HIV-1 protease gene using a Primer ID", *PNAS*, 108(50): 20166-20171 (2011).
Jaffe, et al. "Classification of lymphoid neoplasms: the microscope as a tool for disease discovery", *Blood*, 112(12): 4384-4399 (2008). doi: 10.1182/blood-2008-07-077982.
Jalla, et al. "Enumeration of lymphocyte subsets using flow cytometry: Effect of storage before and after staining in a developing country setting", *Indian J Clin Biochem.*, 19(2): 95-99 (2004). doi: 10.1007/BF02894264.
Jochems and Schlom. "Tumor-infiltrating immune cells and prognosis: the potential link between conventional cancer therapy and immunity", *Exp Biol Med* (Maywood), 236(5): 567-579 (2011). doi: 10.1258/ebm.2011.011007. Epub Apr. 12, 2011.
Johnson et al. "Polysaccharide A from the capsule of Bacteroides fragilis induces clonal CD4+ T cell expansion", J Biol Chem., 290(8): 5007-14 (2015). doi: 10.1074/jbc.M114.621771. Epub Dec. 24, 2014.
Jones, et al. "Human autoimmunity after lymphocyte depletion is caused by homeostatic T -cell proliferation", Proc Natl Acad Sci USA, 110(50):20200-5 (2013). doi: 10.1073/pnas.1313654110. Epub Nov. 26, 2013.
Jung, et al. "Unraveling V(D)J recombination; insights into gene regulation", *Cell*, 116(2): 299-311 (2004).
Kedzierska, et al. "Tracking phenotypically and functionally distinct T cell subsets via T cell repertoire diversity", *Mol Immunol.*, 45(3): 607-618 (2008). Epub Aug. 24, 2007.
Kinde et al. "Detection and quantification of rare mutations with massively parallel sequencing", *PNAS*, 108(23): 9530-9535 and Supporting Information, 16 pages (2011).
Kircher, et al. "Improved based calling for the Illumina Genome Analyzer using machine learning strategies", *Genome Biol.*, 10(8): R83, 9 pages (2009). doi: 10.1186/gb-2009-10-8-r83. Epub Aug. 14, 2009.
Kirsch, et al. "Defining immunoglobulin somatic hypermutation in de novo diffuse large b-cell lymphoma patients: potential application prognosis and risk stratification", Presented for the 2014 ASH Annual Meeting. Poster. 1 page. Dec. 5-9, 2014.
Kirsch et al. "High-throughput TCR sequencing provides added value in the diagnosis of cutaneous T-cell lymphoma", Presented for the 2014 ASH Annual meeting. Poster. 1 page. Dec. 5-9, 2014.
Kivioja et al. "Counting absolute numbers of molecules using unique molecular identifiers," *Nature Methods*, 9(1): 72-76 (2012).
Klarenbeek, P.L. et al. "Human T-cell memory consists mainly of unexpanded clones", *Immunology Letters*, 133: 42-48 (2010).
Klebanoff, et al. "Therapeutic cancer vaccines: are we there yet?", *Immunol Rev.*, 239(1): 27-44 (2011). doi: 10.1111/j.1600-065X. 2010.00979.x.
Klenerman, et al. "Tracking T cells with tetramers: new tales from new tools", *Nat Rev Immunol.*, 2(4):263-272 (2002).
Kneba, et al. "Characterization of clone-specific rearrangement T-cell receptor gamma-chain genes in lymphomas and leukemias by the polymerase chain reaction and DNA sequencing", *Blood*, 84(2):574-581 (1994).
Koboldt et al., "VarScan: variant detection in massively parallel sequencing of individual and pooled samples", Bioinformatics, 25(17): 2283-2285 (2009).
Koch, et al. "Tumor infiltrating T lymphocytes in colorectal cancer: Tumor-selective activation and cytotoxic activity in situ," *Ann Surg.*, 244(6): 986-992; discussion 992-993 (2006).
Kojima et al. "PCR amplification from single DNA molecules on magnetic beads in emulsion: application for high-throughput screening of transcription factor targets", *Nucleic Acids Research*, 33: 17, e150, 9 pages (2005).
Kohlmann, et al. "Integration of next-generation sequencing into clinical practice: are we there yet?", *Semin Oncol.*, 39(1): 26-36, Abstract Only (2012). doi: 10.1053/j.seminoncol.2011.11.008.
Krause et al. "Epitope-Specific Human Influenza Antibody Repertoires Diversify by B Cell Intraclonal Sequence Divergence and Interclonal Convergence", *The Journal of Immunology*, 187: 3704-3711 (2011).
Krueger, et al. "Large scale loss of data in low-diversity illumina sequencing libraries can be recovered by deferred cluster calling", *PLoS One*, 6(1): e16607, 7 pages (2011). doi: 10.1371/journal.pone. 0016607.
Ku, et al. "Exome sequencing: dual role as a discovery and diagnostic tool", *Ann Neurol.*, 71(1):5-14, Abstract Only (2012). doi: 10.1002/ana.22647.
Kumar, et al. "PEG-labeled nucleotides and nanopore detection for single molecule DNA sequencing by synthesis", *Sci Rep.*, 2:684, 8 pages (2012). Epub Sep. 21, 2012.
Kwak, et al. "Induction of immune responses in patients with B-cell lymphoma against the surface-immunogloblin idiotype expressed by their tumors", *N Engl J Med.*, 327(17):1209-1215 (1992).
Kyu et al. "Frequencies of human influenza-specific antibody secreting cells or plasmablasts post vaccination from fresh and frozen peripheral blood mononuclear cells", *Journal of Immunological Methods*, 340: 42-47 (2009).
Ladányi, A., et al. "Prognostic impact of B-cell density in cutaneous melanoma", *Cancer Immunol. Immunother*, 60(12): 1729-1738 (2011).
Landwehr-Kenzel, et al. "Novel GMP—compatible protocol employing an allogeneic B cell bank for clonal expansion of allospecific natural regulatory T cells", Am J Transplant., 14(3):594-606 (2014). doi: 10.1111/ajit.12629. Epub Jan. 27, 2014.
Lassmann, et al. "Application of BIOMED-2 primers in fixed and decalcified bone marrow biopsies: analysis of immunoglobulin H receptor rearrangements in B-cell non-Hodgkin's lymphomas", *J Mol Diagn.*, 7(5): 582-591 (2005).
Lazareva-Ulitsky et al, "On the quality of tree-based protein classification," Bioinformatics, 21(9): 1876-1890 (2005).
Lee, et al. "Characterization of circulating T cells specific for tumor-associated antigens in melanoma patients", *Nat Med.*, 5(6): 677-685, Abstract Only (1999).
Lee, et al. "Prognostic implications of type and density of tumour-infiltrating lymphocytes in gastric cancer", *Br J Cancer*, 99(10): 1704-1711 (2008). doi: 10.1038/sj.bjc.6604738. Epub Oct. 21, 2008.
Lefranc. "IMGT, the international ImMunoGeneTics database", *Nucleic Acids Res.*, 31(1):307-310 (2003).

(56) References Cited

OTHER PUBLICATIONS

Leiden, J.M. et al. "The Complete Primary Structure of the T-Cell Receptor Genes From an Alloreactive Cytotoxic Human T-Lymphocyte Clone", Immunogenetics, 24(1): 17-23 (1986).

Leisner, et al. "One-pot, mix-and-read peptide-MHC tetramers", *PLoS One*, 3(2):e1678, 11 pages (2008). doi: 10.1371/journal.pone.0001678.

Lennon, et al. "A scalable, fully automated process for construction of sequence-ready barcoded libraries for 454", *Genome Biol.*, 11(2):R15, 9 pages (2010). doi: 10.1186/gb-2010-11-2-r15. Epub Feb. 5, 2010.

Leary, et al. "Development of personalized tumor biomarkers using massively parelle sequencing", Sci Transl Med., 2(20): 20ra14 (2010). doi: 10.1126/scitranslmed.3000702.

Leone, et al. "Molecular beacon probes combined with amplification by NASBA enable homogeneous, real-time detection of RNA", *Nucleic Acids Research*, 26(9): 2150-2155 (1998).

Lepore, et al. "Parallel T-cell cloning and deep sequencing of human MAIT cells reveal stable oligoclonal TCRβ repertoire", Nat Commun., 5:3866 (and Corrigendum) (2014). doi: 10.1038/ncomms4866.

Leproust, et al. "Synthesis of high-quality libraries of long (150mer) oligonucleotides by a novel depurination controlled process", *Nucleic Acids Res.*, 38(8): 2522-2540 (2010). doi: 10.1093/nar/gkq163. Epub Mar. 22, 2010.

Lessin, et al. "Molecular diagnosis of cutaneous T-cell lymphoma: polymerase chain reaction amplification of T-cell antigen receptor beta-chain gene rearrangements", *J Invest Dermatol.*, 96(3): 299-302 (1991).

Leventhal et al. "Immune reconstitution/immunocompetence in recipients of kidney plus hematopoietic stem/facilitating cell transplants", Transplantation, 99(2): 288-98 (2015). doi: 10.1097/TP.0000000000000605.

Li, et al. "β cell-specific CD4+ T cell clonotypes in peripheral blood and the pancreatic islets are distinct", *J Immunol.*, 183(11): 7585-7591 (2009). doi: 10.4049/jimmunol.0901587. Epub Nov. 16, 2009.

Li et al, "Mapping short DNA sequencing reads and calling variants using mapping quality scores," Genome Research, 18: 1851-1858 (2008).

Liedtke, et al. "A comparison of methods for RNA extraction from lymphocytes for RT-PCR", *PCR Methods and Applications*, 4(3): 185-187 (1994).

Liu, et al. "CD127 expression inversely correlates with FoxP3 and suppressive function of human CD4+ T reg cells", *J Exp Med.*, 203(7): 1701-1711 (2006). Epub Jul. 3, 2006.

Lo, et al. "T cell immunodominance is dictated by the positively selecting self-peptide", Elife, 3:e01457 (2014). doi: 10.7754/eLife.01457. Epub Jan. 14, 2014.

Logan, et al., "High-throughput immunoglobulin gene sequencing quantifies minimal residual disease in CLL with 10e-6 sensitivity and strongly predicts relapse after allogeneic hematopoietic cell transplantation", Blood, vol. 118 (21), Abstract 2542 (2011).

Logan, et al., "Massively parallel immunoglobulin gene sequencing provided ultra-sensitive minimal residual disease detection and predicts post-transplant relapse in acute lymphoblastic leukemia by three to six months", Blood, vol. 118 (21), Abstract 4104 (2011).

Lord et al. "T-cell receptor sequencing reveals the clonal diversity and overlap of colonic effector and FOXP3+ T cells in ulcerative colitis", Inflamm Bowel Dis., 21(1):19-30 (2015). doi: 10.197/MIB.0000000000000242.

Lossius et al. "High-throughput sequencing of TCR repertoires in multiple sclerosis reveals intrathecal enrichment of EBV-reactive CD8+ T cells", Eur J Immunol., 44(11): 3439-52 (2014). doi: 10.1002/eji.201444662. Epub Sep. 16, 2014.

Lossos, et al. "Transformation of follicular lymphoma to diffuse large-cell lymphoma: alternative patterns with increased or decreased expression of c-myc and its regulated genes", *PNAS*, 99(13): 8886-8891 (2002). Epub Jun. 19, 2002.

Lowman, et al. "Monovalent phage display: a method for selecting variant proteins from random libraries", *Methods: A Companion to Methods in Enzymology*, 3: 205-216, Abstract Only (1991).

Lyamichev, et al. "Polymorphism identification and quantitative detection of genomic DNA by invasive cleavage of oligonucleotide probes", *Nat Biotechnol.*, 17(3): 292-396 (1999).

Mackay, et al. "Real-time PCR in virology", *Nucleic Acids Res.*, 30(6): 1292-305 (2002).

Mahmoud, S.M.A. et al. "Tumor-Infiltrating CD8+ Lymphocytes Predict Clinical Outcome in Breast Cancer", Journal of Clinical Oncology, 29(15): 1949-1955 (2011).

Maldonado, et al. "Intramuscular therapeutic vaccination targeting HPV16 induces T cell responses that localized in mucosal lesions", Sci Transl Med., 6(221): 221ra13 (2014). doi: 10.1126/scitranslmed.3007323.

Malyguine, et al. "ELISPOT Assay for Monitoring Cytotoxic T Lymphocytes (CTL) Activity in Cancer Vaccine Clinical Trials", *Cells*, 1(2): 111-126 (2012). doi: 10.3390/cells1020111.

Manion et al., "Reducing Error in Next Generation Sequencing Data with NextGENe Software's Condensation Tool™", Mar. 2009, pp. 1-3, XP05526038.

Manrao, et al. "Reading DNA at single-nucleotide resolution with a mutant MspA nanopore and phi29 DNA polymerase", *Nat Biotechnol.*, 30(4): 349-353 (2012). doi: 10.1038/nbt.2171.

Mar et al. "Inferring steady state single-cell gene expression distributions from analysis of mesoscopic samples", *Genome Biology*, 7(12): R119, 12 pages (2006).

Marrero, et al. "High-throughput sequencing of islet-infiltrating memory CD4+ T cells reveals a similar pattern of TCR Vβ usage in prediabetic and diabetic NOD mice", PLoS One, 8(10):e76546 (2013). doi: 10.1371/journal.pone.0076546. eCollection 2013.

Martin-Jimenez, et al. "Molecular characterization of heavy chain immunoglobulin gene rearrangements in Waldenström's macroglobulinemia and IgM monoclonal gammopathy of undetermined significance", *Haematologica*, 92(5): 635-642 (2007).

Mary et al. "Analysis of gene expression at the single-cell level using microdroplet-based microfluidic technology", *Biomicrofluidics*, 5: 024109-1-024109-10 (2011).

Matsubara, et al. "Microchamber array based DNA quantification and specific sequence detection from a single copy via PCR in nanoliter volumes", *Biosens Bioelectron*, 20(8): 1482-1490, Abstract Only (2005).

Mattoo et al. "De novo oligoclonal expansions of circulating plasmablasts in active and relapsing IgG4-related disease", J Allergy Clin Immunol., 134(3):679-87 (2014). doi: 10.1016/j.jaci.2014.03.034. Epub May 6, 2014.

Mazor et al. "Antibody internalization studied using a novel IgG binding toxin fusion", *Journal of Immunological Methods*, 321: 41-59 (2007).

Mazumder, et al., "Detection of multiple myeloma cells in peripheral blood using high-throughput sequencing assay" Blood, vol. 120, No. 21, Abstract 321 (Conference Abstract), Entire Abstract (2012).

McCloskey et al. "Encoding PCR products with batch-stamps and barcodes," *Biochem. Genet.*, 45: 761-767 (2007).

Mei et al. "Blood-borne human plasma cells in steady state are derived from mucosal immune responses", Blood, 113(11): 2461-2469 (2009).

Meijer et al. "Isolation of Human Antibody Repertoires with Preservation of the Natural Heavy and Light Chain Pairing", *J. Mol. Biol.*, 358: 764-772 (2006).

Meier et al. "Simultaneous evaluation of T-cell and B-cell clonality, t(11;14) and t(14;18), in a single reaction by a four-color multiplex polymerase chain reaction assay and automated High-Resolution fragment analysis", *American Journal of Pathology*, 159(6): 2031-2043 (2001).

Meier, et al. "The influence of different stimulation conditions on the assessment of antigen-induced CD154 expression on CD4+ T cells", *Cytometry* A., (11):1035-1042 (2008). doi: 10.1002/cyto.a.20640.

Metzker, "Sequencing Technologies—The Next Generation", *Nature Reviews, Genetics*, 11:31-46 (2010).

Meyer et al. "Targeted high-throughput sequencing of tagged nucleic acid samples", *Nucleic Acids Research*, 35(15): e97, 5 pages (2007).

(56) References Cited

OTHER PUBLICATIONS

Michálek, et al. "Identification and monitoring of graft-versus-host specific T-cell clone in stem cell transplantation", *The Lancet*, 361(9364): 1183-1185 (2003).
Miller, et al., "Assembly algorithms for next-generation sequencing data", *Genomics*, 95(6): 315-327 (2010).
Miltenyi, et al. "High gradient magnetic cell separation with MACS", *Cytometry*, 11(2): 231-238 (1990).
Miner et al. "Molecular barcodes detect redundancy and contamination in hairpin-bisulfite PCR", *Nucleic Acids Research*, 32(17): e135, 4 pages (2004).
Mitra, et al. "Fluorescent in situ sequencing on polymerase colonies", *Anal Biochem.*, 320(1): 55-65, Abstract Only (2003).
Miyashita, et al. "N-Methyl substituted 2',4'—BNANC: a highly nuclease-resistant nucleic acid analogue with high-affinity RNA selective hybridization", *Chem Commun* (Camb), (36): 3765-3767, Abstract Only (2007). Epub Jul. 9, 2007.
Moen, et al. "Immunoglobulin G and A antibody responses to Bacteroides forsyth and Prevotella intermedia in sera and synovial fluids of arthritis patients", *Clin Diagn Lab Immunol.*, 10(6): 1043-1050 (2003).
Molloy, et al. "Soluble T cell receptors: novel immunotherapies", *Curr Opin Pharmacol.*, 5(4): 438-443 (2005) (Abstract Only).
Moody, et al. "Antigen-specific B cell detection reagents: use and quality control", *Cytometry A.*, 73(11): 1086-1092 (2008). doi: 10.1002/cyto.a.20599.
Morgan, et al. "Cancer regression in patients after transfer of genetically engineered lymphocytes", *Science*, 314(5796): 126-129 (2006). Epub Aug. 31, 2006.
Morozova et al. "Applicitions of New Sequencing Technologies for Transcriptome Analysis", *Annu. Rev. Genomics Hum. Genet.*, 10: 135-151 (2009).
Morrissy et al. "Next-generation tag sequencing for cancer gene expression profiling", *Genome Research*, 19: 1825-1835 (2009).
Moura, et al. "Alterations on peripheral blood B-cell subpopulations in very early arthritis patients", *Rheumatology* (Oxford), 49(6): 1082-1092 (2010). doi: 10.1093/rheumatology/keq029. Epub Mar. 7, 2010.
Mueller, et al. "Human Treg responses allow sustained recombinant adeno-associated virus-mediated transgene expression", *J Clin Invest.*, 123(12): 5310-8 (2013). doi: 10.1172/JCI70314. Epub Nov. 15, 2013.
Muraro, et al. "T cell repertoire following autologous stem cell transplantation for multiple sclerosis", *J Clin Invest.*, 124(3): 1168-72 (2014). doi: 10.1172/JCI71691. Epub Feb. 17, 2014.
Naito, et al. "CD8+T cells infiltrated within cancer cell nests as a prognostic factor in human colorectal cancer", *Cancer Research*, 58(16): 3491-3494 (1998).
Nakano, et al. "Single-molecule PCR using water-in-oil emulsion", *J Biotechnol.*, 102(2): 117-124, Abstract Only (2003).
Navarrete, et al. "Upfront immunization with autologous recombinant idiotype Fab fragment without prior cytoreduction in indolent B-cell lymphoma", *Blood*, 117(5): 1483-1491 (2011). doi: 10.1182/blood-2010-06-292342, Epub Nov. 2, 2010.
Needleman and Wunsch. "A general method applicable to the search for similarities in the amino acid sequence of two proteins", J Mol Biol., 48(3): 443-453 (1970).
Nelson. "CD20+ B cells: the other tumor-infiltrating lymphocytes", *The Journal of Immunology*, 185(9): 4977-4982 (2010). doi: 10.4049/jimmunol.1001323.
Newman, et al. "Identification of an antigen-specific B cell population", *J Immunol Methods*, 272(1-2): 177-187, Abstract Only (2003).
Nielsen, et al. "Peptide nucleic, acid (PNA). A DNA mimic with a pseudopeptide backbone". *Chem, Soc. Rev.*, 26:73-78, Abstract Only (1997).
Nolan, T. et al. "Quantification of mRNA using real-time RT-PCR", *Nature Protocols*, 1(3):1559-1582 (2006).
Nosho, et al. "Tumour-infiltrating T-cell subsets, molecular changes in colorectal cancer, and prognosis: cohort study and literature review", *J Pathol.*, 222(4): 350-366 (2010). doi: 10.1002/path.2774.

Nucleis product webpage, "Exonuclease I-Shrimp alkaline phosphatase clean up of PCR products," (Published on webpage 2013) Downloaded Dec. 15, 2015.
Oble, et al. "Focus on TILs: prognostic significance of tumor infiltrating lymphocytes in human melanoma", *Cancer Immunity*, 9: 3, 20 pages (2009).
O'Brian et al., "Sorting out mix-ups. The provenance of tissue sections may be confirmed by PCR using microsatellite markers", Am. J. Clin. Pathol., 106(6)L 758-764 (1996). (Abstract Only).
Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.
Ohtani. "Focus on TILs: prognostic significance of tumor infiltrating lymphocytes in human colorectal cancer", *Cancer Immunity*, 7: 4, 9 pages (2007).
Okello et al. "Comparison of methods in the recovery of nucleic acids from archival formalin-fixed paraffin-embedded autopsy tissues", *Anal Biochem.*, 400(1): 100-117 (2010). doi: 10.1016/j.ab.2010.014. Epub Jan. 15, 2010.
Ottensmeier, et al. "Analysis of VH genes in follicular and diffuse lymphoma shows ongoing somatic mutation and multiple isotype transcripts in early disease with changes during disease progression", *Blood*, 91(11): 4292-4299 (1998).
Pagès, Franck. Tumor-associated immune parameters for personalized patient care. Sci Transl Med., 5(214):214fs42 (2013). doi: 10.1126/scitranslmed.3007942.
Palmowski, et al. "The use of HLA class I tetramers to design a vaccination stratgy for melanoma patients", *Immunol Rev.*, 188: 155-163 (2002) (Abstract Only).
Palomaki, et al. "DNA sequencing of maternal plasma reliably identifies trisomy 18 and trisomy 13 as well as Down syndrome: an international collaborative study", *Genet Med.*, 14(3): 296-305 (2012). doi: 10.1038/gim.2011.73. Epub Feb. 2, 2012.
Pan, et al. "A new FACS approach isolates hESC derived endoderm using transcription factors", *PLoS One*, 6(3): e17536, 9 pages (2011). doi: 10.1371/journal.pone.0017536.
Parameswaran et al. "A pyrosequencing-tailored nucleotide barcode design unveils opportunities for large-scale sample multiplexing", *Nucleic Acids Research*, 35(19): e130, 9 pages (2007).
Parmigiani, et al. "Design and analysis issues in genome-wide somatic mutation studies of cancer", *Genomics*, 93(1): 17-21 (2009). doi: 10.1016/j.ygeno.2008.07.005. Epub Aug. 23, 2008.
Pasqual et al. "Quantitative and qualitative changes in V-J alpha rearrangements during mouse thymocytes differentiation: implication for a limited T cell receptor alpha chain repertoire", *Journal of Experimental Medicine*, 196(9): 1163-1171 (2002). XP002322207 ISSN: 0022-1007.
Paszkiewicz et al, "De novo assembly of short sequence reads," Briefings in Bioinformatics, 11(5): 457-472 (2010).
Payne, et al. "Peripheral blood mononuclear cells of patients with breast cancer can be reprogrammed to enhance anti-HER-2/neu reactivity and overcome myeloid-derived suppressor cells", Breast Cancer Res Treat. 142(1):45-51 (2013). doi: 10.1007/s10549-013.2733. 5. Eoub Oct. 25, 2013.
Peet. "The Measurement of Species Diversity", *Annual Review of Ecology and Systematics*, 5: 285-307 Abstract Only (1974).
Petrosino et al. "Metagenomic pyrosequencing and microbial identification", *Clin Chem.*, 55(5): 856-866 (2009). doi: 10.1373/clinchem.2008.107565. Epub Mar. 5, 2009.
PCT/US2009/006053, Written Opinion dated Jun. 15, 2010, 4 pages.
PCT/US2010/021264, International Preliminary Report on Patentability mailed Jul. 19, 2011, 5 pages.
PCT/US2010/037477, International Preliminary Report on Patentability dated Jan. 4, 2012, 7 pages.
PCT/US2011/000791, International Preliminary Report on Patentability dated Nov. 6, 2012, 10 pages.
PCT/US2011/049012, International Preliminary Report on Patentability dated Feb. 26, 2013, 5 pages.
PCT/US2012/058989, International Search Report and Written Opinion dated Mar. 29, 2013, 12 pages.
PCT/US2012/058989, International Preliminary Report on Patentability dated Apr. 15, 2014, 8 pages.

(56) References Cited

OTHER PUBLICATIONS

PCT/US2012/061977, International Search Report and Written Opinion dated Feb. 25, 2013, 11 pages.
PCT/US2012/061977, International Preliminary Report on Patentability dated May 6, 2014, 7 pages.
PCT/US2012/068617, International Preliminary Report on Patentability mailed Jun. 10, 2014, 6 pages.
PCT/US2012/070674, International Search Report and Written Opinion dated Feb. 22, 2013, 8 pages.
PCT/US2012/070674, International Preliminary Report on Patentability dated Aug. 5, 2014, 6 pages.
PCT/US2013/065493, International Search Report and Written Opinion dated Jan. 20, 2014, 14 pages.
PCT/US2013/065493, International Preliminary Report on Patentability dated Apr. 21, 2015, 10 pages.
PCT/US2013/065509, International Search Report and Written Opinion dated Jan. 20, 2014, 9 pages.
PCT/US2013/065757, International Preliminary Report on Patentability dated Apr. 21, 2015, 6 pages.
PCT/US2013/065757, International Preliminary Report on Patentability dated Apr. 28, 2015, 6 pages.
PCT/US2013/037258, International Search Report and Written Opinion dated Aug. 19, 2013, 8 pages.
PCT/US2013/037258, International Preliminary Report on Patentability dated Oct. 21, 2014, 6 pages.
PCT/US2014/017416, International Search Report dated May 12, 2014, 9 pages.
PCT/US2014/017416, Written Opinion dated May 12, 2014, 9 pages.
PCT/US2014/017416, International Preliminary Report on Patentability dated Aug. 25, 2015, 10 pages.
Plasilova et al. "Application of the Molecular Analysis of the T-Cell Receptor Repertoire in the Study of Immune-Mediated Hematologic Diseases", *Hematology*, 8(3): 173-181 (2003).
Polstra, et al. "Development of real-time NASBA assays with molecular beacon detection to quantify mRNA coding for HHV-8 lytic and latent genes", *BMC Infect Dis.*, 2: 18 (2002). Epub Sep. 4, 2002.
Pourmand, et al. "Direct electrical detection of DNA synthesis", *PNAS*, 103(17): 6466-6470 (2006). Epub Apr. 13, 2006.
Polz and Cavanaugh. "Bias in Template-to-Product Ratios in Multitemplate PCR", *Applied and Environmental Microbiology*, 64(10): 3724-3730 (1998).
Poschke et al. "A phase I clinical trial combining dendritic cell vaccination with adoptive T cell transfer in patients with stage IV melanoma", Cancer Immunol Immunother., 63(10): 1061-71 (2014). doi: 10.1007/s00262-014-1575-2. Epub Jul. 4, 2014.
Prabakaran et al. "454 antibody sequencing—error characterization and correction", *BMC Research Notes*, 4: 404 (2011).
Putnam, et al. "Clinical grade manufacturing of human alloantigen-reactive regulatory T cells for use in transplantation", Am J Transplant., 13(11): 3010-20 (2013). doi: 10.1111/ajt.12433. EpubSep. 18, 2013.
Qiu et al. "DNA sequence-based "bar codes" for tracking the origins of expressed sequence tags from a maize cDNA library constructed using multiple mRNA sources", *Plant Physiology*, 133(2): 475-481 (2003).
Quince et al. "Removing Noise From Pyrosequenced Amplicons", *BMC Informatics*, 12: 38 (2011).
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].
Ramsden, et al. "V(D)J recombination: Born to be wild", *Semin Cancer Biol.*, 20(4): 254-260 (2010). doi: 10.1016/j.semcancer.2010.06.002. Epub Jul. 1, 2010.
Reddy, et al. "Monoclonal antibodies isolated without screening by analyzing the variable-gene repertoire of plasma cells", *Nature Biotechnology*, 28(9): 965-969 (2010). doi: 10.1038/nbt.1673. Epub Aug. 29, 2010.

Robert, et al. "CTLA4 blockade broadens the peripheral T-cell receptor repertoire", Clin Cancer Res., 20(9):2424-32 (2014). doi: 10.1158/1078-0432.CCR-13-2648. Epub Feb. 28, 2014.
Robins, H. et al. "Digital Genomic Quantification of Tumor Infiltrating Lymphocytes", *Science Translational Medicine*, 5:214ra169, 19 pages, Supplementary Materials (2013).
Robins, H. et al. "Overlap and Effective Size of the Human CD8+ T Cell Receptor Repertoire", *Science Transitional Medicine*, 2(47, 47ra64):17 pages, Supplemental Materials (2010).
Robins, H. et al. "The Computational Dectection of Functional Nucleotide Sequence Motifs in the Coding Regions of Organisms", *Exp Biol Med*, 233(6): 665-673 (2008).
Ronaghi, et al. "A sequencing method based on real-time pyrophosphate", *Science*, 281(5375): 363, 365, 5 pages (1998).
Rosenberg, S.A. et al. "New Approach to the Adoptive Immunotherapy of Cancer with Tumor-Infiltrating Lymphocytes", *Science*, 233(4770): 1318-1321 (1986).
Rothberg, et al. "An integrated semiconductor device enabling non-optical genome sequencing", *Nature*, 475(7356): 348-352 (2011). doi: 10.1038/nature10242.
Rothberg et al. "The development and impact of 454 sequencing", *Nature Biotechnology*, 26(10): 1117-1124 (2008).
Salzberg. "Mind the gaps", *Nature Methods*, 7(2): 105-106 (2010).
Sanchez-Freire et al. "Microfluidic single-cell real-time PCR for comparative analysis of gene expression patterns", *Nature Protocols*, 7(5): 829-838 (2012).
Sandberg, et al. "Capturing whole-genome characteristics in short sequences using a naïve Bayesian classifier", *Genome Res.*, 11(8): 1404-9 (2001).
Sartorius Stedim Biotech product brochure, "Primer removal after a PCR reaction with Vivacon® 2", (2010).
Sato et al. "Intraepithelial CD8+ tumor-infiltrating lymphocytes and a high CD8+/regulatory T cell ratio are associated with favorable prognosis in ovarian cancer", *PNAS*, 102(51): 18538-18543 (2005), Epub Dec. 12, 2005.
Satoh et al. "Pretreatment with restriction enzyme or bovine serum albumin for effective PCR amplification of Epstein-Barr virus DNA in DNA extracted from paraffin-embedded gastric carcinoma tissue", *J Clin Microbiol.*, 36(11): 3423-3425 (1998).
Schlissel, M.S. et al. "Leukemia and lymphoma: a cost of doing business for adaptive immunity", *Genes Dev.*, 20(12): 1539-1544 (2006).
Schloss. PD et al. Reducing the Effects of PCR Amplification and Sequencing Artifacts on 16S Rrna—Based Studies. PLoS One. Dec. 14, 2011, vol. 6, No. 12; e27310; Doi: 1 0.1371/journal.pone0027310.
Schmitt et al. "Detection of ultra-rare mutations by next-generation sequencing," *PNAS*, 109(36): 14508-14513 and Supporting Information, 9 pages (2012).
Schreiber et al. "Cancer immunoediting: integrating immunity's roles in cancer suppression and promotion", *Science*, 331(6024): 1565-1570 (2011). doi: 10.1126/science.1203486.
Schweiger et al. "Genome-wide massively parallel sequencing of formaldehyde fixed-paraffin embedded (FFPE) tumor tissues for copy-number- and mutation-analysis", *PLoS One*, 4(5): e5548, 7 pages (2009). doi: 10.1371/journal.pone.0005548. Epub May 14, 2009.
Sebastian, E. et al., "Molecular Characterization of immunoglobulin gene rearragements in diffuse large B-cell lymphoma", *Am. J. Pathol.*, 181: 1879-1888, Abstract (2012). (Epub: Sep. 28, 2012).
Sehouli et al. "Epigenetic quantification of tumor-infiltrating T-lymphocytes" *Epigentics*, 6(2): 236-246 (2011). Epub Feb. 1, 2011.
Seitz, et al. "Reconstitution of paired T cell receptor α- and β-chains from microdissected single cells of human inflammatory tissues", *PNAS*, 103: 12057-12062 (2006).
Seo, et al. "Four-color DNA sequencing by synthesis on a chip using photocleavable fluroescent nucleotides", *PNAS*, 102(17): 5926-5931 (2005). Epub Apr. 13, 2005.
Sfanos et al. "Human Prostate-Infiltrating CD8+ T Lymphocytes are Oligoclonal and PD-1+", *The Prostate*, 69(15): 1694-1703 (2009).
Shendure, et al. "Accurate multiplex polony sequencing of an evolved bacterial genome", *Science*, 309(5741): 1728-1732, Abstract Only (2005). Epub Aug. 4, 2005.

(56) References Cited

OTHER PUBLICATIONS

Sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.
Shino, et al. "Usefulness of immune monitoring in lung transplantation using adenosine triphosphate production in activated lymphocytes", *The Journal of Heart and Lung Transplant*, 31: 996-1002 (2012).
Shiroguchi et al. "Digital RNA sequencing minimizes sequence-dependent bias and amplification noise with optimized single-molecule barcodes", *PNAS*, 109(4): 1347-1352 (2012).
Shoemaker et al. "Quantitative phenotypic analysis of yeast deletion mutants using a highly parallel molecular bar-coding strategy," *Nature Genetics*, 14(4): 450-456 (1996).
Shumaker, et al. "Mutation detection by solid phase primer extension", *Hum Mutat.*, 7(4): 346-354, Abstract Only (1996).
Sia, et al. "Microfluidic devices fabricated in poly(dimethylsiloxane) for biological studies", *Electrophoresis*, 24(21): 3563-3576, Abstract Only (2003).
Sims, et al. "Fluorogenic DNA sequencing in PDMS microreactors", *Nat Methods*, 8(7): 575-580 (2011). doi: 10.1038/nmeth.1629.
Sims, et al. "MHC-peptide tetramers for the analysis of anitgen-specific T cells", *Expert Rev Vaccines*, 9(7): 765-774 (2010). doi: 10.1586/erv.10.66.
Smith, et al. "Comparison of biosequences", *Advances in Applied Mathematics*, 2: 482-489 (1981).
Smith et al. "Rapid generation of fully human monocolonal antibodies specific to a vaccinating antigen", *Nature Protocols*, 4(3): 372-384 and Corrigenda (2009).
Smith et al. "Rapid whole-genome mutational profiling using next-generation sequecing technologies", *Genome Research*, 18: 1638-1642 (2008).
Smith et al. "Quantitative phenotyping via deep barcode sequencing", *Genome Research*, 19: 1836-1842 (2009).
Smith et al, "Using quality scores and longer reads improves accuracy of Solexa read mapping," BMC Bioinformatics, 9: 128 (2008).
Sobrino, et al. "SNPs in forensic genetics: a review on SNP typing methodologies", *Forensic Sci Int.*, 154(2-3): 181-194, Abstract Only (2005). Epub Jan. 11, 2005.
Spreafico, et al. "A circulating reservoir of pathogenic-like CD4+T cells Shares a genetic and phenotypic signature with the inflamed synovial micro-environment", *Ann Rheum Dis.*, 0: 1-7 (2014). doi: 10.1136/annrheumdis-2014-206226. [Epub ahead of print].
Srinivasan et al. "Effect of fixatives and tissue processing on the content and integrity of nucleic acids", *Am J Pathol.*, 161(6): 1961-1971 (2002).
Steenbergen, et al. "Frequent onging T-cell receptor rearrangements in childhood B-precursor acute lymphoblastic leukemia: implications for monitoring minimal residual disease", *Blood*, 86(2): 692-702, Abstract Only (1995).
Stemmer, et al. "Single-step assembly of a gene and entire plasmid from large numbers of oligodeoxyribonucleotides", *Gene*, 164(1): 49-53 (1995).
Stewart and Schwartz. "Immunoglobulin V regins and the B cell", *Blood*, 83(7): 1717-1730 (1994).
Stickler, et al. "An in vitro human cell-based assay to rank the relative immunogenicity of proteins", *Toxicol Sci.*, 77(2): 280-289 (2004). Epub Dec. 22, 2003.
Stiller et al. "Direct multiplex squencing (DMPS)—a novel method for targeting high-throughput sequencing of ancient and highly degraded DNA", *Genome Research*, 19: 1843-849 (2009).
Stratton. "Exploring the genomes of cancer cells: progress and promise", *Science*, 331(6024): 1553-1558 (2011). doi: 10.1126/science.1204040.
Sumida et al. "T cell receptor Vα repertoire of infiltrating T cells in labial salivary glands from patients with Sjögren's syndrome", *J Rheumatol.*, 21:1655-1661 (1994).

Swarup and Rajeswari. "Circulating (cell-free) nucleic acids—a promising, non-invasive tool for early detection of several human diseases", *FEBS Letters*, 581(5): 795-799 (2007). Epub Feb. 2, 2007.
Szereday et al., "Somatic Mutation of the 5' Noncoding Region of the BCL-6 Gene is Associated with Intraclonal Diversity and Clonal Selection in Histological Transformation of Follicular Lymphoma", The American Journal of Pathology, 156(3): 1017-1024 (2000).
Takamatsu, et al., "A comparison between next-generation sequencing and ASO-qPCR for minimal residual disease detection in multiple myeloma", *J. Clin. Oncol.*, 31(Supplement 1): Abstract 8601 (Conference Abstract), Entire Abstract (2013).
Tanaka et al. "Single-Cell Analysis of T-Cell Receptor Repertoire of HTLV-1 Tax-Specific Cytotoxic T Cellls in Allogeneic Transplant Recipients with Adult T-Cell Leukemia/Lymphoma", *Cancer Research*, 70: 6181-6192 (2010).
Taubenheim et al. "High Rate of Antibody Secretion is not Integral to Plasma Cell Differentiation as Revealed by XBP-1 Deficiency", *The Journal of Immunology*, 189: 3323-3338 (2012).
Tautz, et al. "Cryptic simplicity in DNA is a major source of genetic variation", *Nature* 322(6060): 652-656 (1986).
Tawfik, et al. "Man-made cell-like compartments for molecular evolution", *Nat Biotechnol.*, 16(7): 652-656, Abstract Only (1998).
ten Bosch et al. "Keeping Up With the Next Generation Massively Parallel Sequencing in Clinical Diagnostics", *Journal of Molecular Diagnostics*, 10(6): 484-492 (2008).
Thiel, et al. "Antigen-specific cytometry—new tools arrived!", *Clin Immunol.*, 111(2): 155-161, Abstract Only (2004).
Toinoven et al. "Islet-associated T-cell receptor-β CDR sequence repertoire in prediabetic NOD mice reveals antigen-driven T-cell expansion and shared usage of VβJβ TCR chains", Mol Immunol., 64(1):127-35 (2015). doi: 10.1016/j.molimm.2014.11.009. Epub Dec. 3, 2014.
Toriello et al. "Integrated microfluidic bioprocessor for single-cell expression analysis", *PNAS*, 105(51): 20173-20178 (2008).
Tsai et al. "Discovery of rare mutations in populations: TILLING by sequencing", Plant Physiology, 156(3): 1257-1268 (and Supplemental Data) (2011).
Tsankova, et al, "Peripheral T-cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.
Tschumper, et al. "Comprehensive assessment of potential multiple myeloma immunoglobulin heavy chain V-D-J intraclonal variation using massively parallel pyrosequencing", *Oncotarget*, 3(4): 502-613 (2012).
Tumeh et al. "PD-1 blockade induces responses by inhibiting adaptive immune resistance", Nature, 515: 568-571 (2014). doi:10.1038/nature13954.
Turcotte and Rosenberg. "Immunotherapy for metastatic solid cancers", *Adv Surg.*, 45: 341-360 (2011).
Unrau and Deugau. "Non-cloning amplification of specific DNA fragments from whole genomic DNA digests using DNA 'indexers'", *Gene.*, 145(2): 163-169, Abstract Only, 2 pages (1994).
Uppaluri et al. "Focus on TLs: prognostic significance of tumor infiltrating lymphocytes in head and neck cancers", *Cancer Immunity*, 8:16, 10 pages (2008).
Urban, et al. "A systematic and quantitative analysis of PCR template contamination", *J Forensic Sci.*, 45(6): 1307-1311 (2000).
Urquhart, et al. "Rate-controlled delivery systems in drug and hormone research", *Annu Rev Pharmacol Toxicol.*, 24: 199-236, Abstract Only (1984).
Varley and Mitra. "Nested patch PCR enables highly multiplexed mutation discovery in candidate genes", *Genome Research*, 18: 1844-1850 (2008).
Venturi, et al. "A mechanism for TCR sharing between T cell subsets and individuals reveals by pyrosequencing", *J Immunol.*, 186(7): 4285-4294 (2011). doi: 10.4049/jimmunol.1003898. Epub Mar. 7, 2011.
Vester, et al. "LNA (locked nucleic acid): high-affinity targeting of complementary RNA and DNA", *Biochemistry*, 43(42): 13233-13241, Abstract Only (2004).

(56) References Cited

OTHER PUBLICATIONS

Vlassov, et al. "Circulating nucleic acids as a potential source for cancer biomarkers", Curr Mol Med., 10(2): 142-165 (2010).

Vogelstein et al. "Cancer genome landscapes", Science, 339(6127): 1546-1558 (2013). doi: 10.1126/science.1235122.

Wälchli, et al. "A practical approach to T-cell receptor cloning and expression", PLoS One, 6(11): e27930, 11 pages (2011). doi: 10.1371/journal.pone.0027930. Epub Nov. 21, 2011.

Wang, et al. "Balanced-PCR amplification allows unbiased identification of genomic copy changes in minute cell and tissue samples", Nucleic Acids Research, 32(9): e76, 10 pages (2004).

Wang et al. "Immunorepertoire analysis by multiplex PCR amplification and high throughput sequencing", Poster-Program 42.6, The 96th Annual Meeting of the America Association of Immunologists, Seattle, USA, May 8-12, 2009, 1 page.

Welch and Link. "Genomics of AML: clinical applications of next-generation sequencing", American Society of Hematology, 2011: 30-35 (2011). doi: 10.1182/asheducation-2011.1.30.

Wells, et al. "Rapid Evolution of peptide and protein binding properties in vitro", Curr Opin Biotechnol., 3(4): 355-362, Abstract Only (1992).

Weng, Wen-Kai et al., "Graft-Versus-Lymphoma Effect After Non-Myeloablative Allogeneic Transplant Induces Molecular Remission Assessed by High-Throughput Sequencing of T Cell Receptor in Patients with Advanced Stage Mycosis Fungoides and Sezary Syndrome", Blood, vol. 118, No. 21, Nov. 2011. p. 1346. XP055213326. & 53rd Annual Meeting and Exposition of the American-Society-of-Hematology (ASH); San Deigo. CA. USA; Dec. 10-13, 2011.

Weng, et al. "Minimal residual disease monitoring with high-throughput sequencing of T-cell receptors in cutaneous T cell lymphoma", Sci Transl Med., 5(214):214ra171 (2013). doi: 10.1126/scitranslmed.3007420.

Westermann and Pabst. "Distribution of lymphocyte subsets and natural killer cells in the human body", Clin Investig., 70(7): 639-544 (1992).

Weusten, et al, "Principles of quantitation of viral loads using nucleic acid sequence-based amplification in combination with homogeneo detection using molecular beacons", Nucleic Acids Res., 30(6): e26, 7 pages (2002).

White et al. "High-throughput microfluidic single-cell RT-qPCR", PNAS, 108(34): 13999-14004 (2011).

Whiteford, et al. "Swift: primary data analysis for the Illumina Solexa sequencing platform", Bioinformatics, 25(17): 2194-2199 (2009). doi: 10.1093/bioinformatics/btp383. Epub Jun. 23, 2009.

Williams, et al. "Amplification of complex gene libraries by emulsion PCR", Nat Methods, 3(7): 545-550 (2006).

Wolda. "Similarity Indices, Sample Size and Diversity", Oecologia (Berl), 50:296-302 (1981).

Wolfl, et al. "Activation-induced expression of CD137 permits detection, isolation, and expansion of the full repertoire of CD8+ T cells responding to antigen without requiring knowledge of epitope specificities", Blood, 110(1): 201-210 (2007). Epub Mar. 19, 2007.

Wolfl, et al. "Use of CD137 to study the full repertoire of CD8+ T cells without the need to know epitope specificities", Cytometry A., 73(11): 1043-1049 (2008). doi: 10.1002/cyto.a.20594.

Wood, et al. "Using next-generation sequencing for high resolution multiplex analysis of number variation from nanogram quantities of DNA from formalin-fixed paraffin-embedded specimens", Nucleic Acids Research, 38(14): e151, 11 pages (2010). doi: 10.1093/nar/gkq510. Epub Jun. 4, 2010.

Wrammert et al. "Rapid cloning of high-affinity human monoclonal antibodies against influenza virus", Nature, 453: 667-672 (2008).

Wu, et al., "Detection of Minimal Residual Disease in B Lymphoblastic Leukemia by High-Throughput Sequencing of IGH", Clin Cancer Res., 20(17): 4540-8 (2014). Published OnlineFirst Jun. 26, 2014; doi: 10.1158/1078-0432.CCR-13-3231.

Wu, Y-C. et al. "High-throughput immunoglobulin repertoire analysis distinguishes between human IgM memory and switched memory B-cell populations", Blood Journal, 116(7): 1070-1078, 22 pages (2010).

Wu et al. "Focused Evolution of HIV-1 Neutralizing Antibodies Revealed by Structures and Deep Sequencing", Science, 333: 1593-1602 (2011).

Wu, H.D. et al. "The Lymphocytic Infiltration in Calcific Aortic Stenosis Predominantly Consists of Clonally Expanded T Cells", The Journal of Immunology, 178(8): 5329-5339 (2007).

Xiong, et al. "Chemical gene synthesis: strategies, softwares, error corrections, and applications", FEMS Microbiol Rev., 32(3): 522-540 (2008). doi: 10:1111/j.1574-6976.2008.00109.x. Epub Apr. 2, 2008.

Xiong, et al. "Non-polymerase-cycling-assembly-based chemical gene synthesis: strategies, methods, and progress", Biotechnol Adv., 26(2): 121-134, Abstract Only (2008). Epub Nov. 7, 2007.

Yan et al. "Emergence of a STAT3 Mutated NK Clone in LGL Leukemia", Leuk Res Rep., 4(1):4-7 (2014) doi: 10.1016/j.lrr.2014.12.001. eCollection 2015.

Yao, et al. "Analysis of the CDR3 length repertoire and the diversity of TCRα chain in human peripheral blood T Lymphocytes", Cell Mol Immunol., 4(3): 215-220 (2007).

Yeh, et al. "Regulating DNA translocation through functionalized soft nanopores", Nanoscale, 4(8): 2685-4693, Abstact Only (2012). doi: 10.1039/c2nr30102d. Epub Mar. 15, 2012.

Yassai, M.B. et al. "A clontype nomenclature for T cell receptors", Immunogentics, 61:493-502 (2009).

York, et al. "Highly parallel oligonucleotide purification and functionalization using reversible chemistry", Nucleic Acids Res., 40(1): e4, 7 pages (2012). doi: 10.1093/nar/gkr910. Epub Oct. 29, 2011.

Yu and Fu. "Tumor-infiltrating T lymphocytes: friends or foes?", Lab Invest., 86(3): 231-245 (2006).

Zagnoni, et al. "Droplet Microfluidics for High-throughput Analysis of Cells and Particles", Methods in Cell Biology, Chapter 2, 102: 23-48 (2011).

Zehentner et al. "Minimal Disease Detection and Confirmation in Hematologic Malignancies: Combining Cell Sorting with Clonality Profiling", Clinical Chemistry, 52(3): 430-437 (2006).

Zhou et al. "Isolation of purified and live Foxp3+ regulatory T cells using FACS sorting on scatter plot", J Mol Cell Biol., 2(3): 164-169 (2010). doi: 10.1093/jmcb/mjq007. Epub Apr. 29, 2010.

Zhu, et al. "Immune surveillance by CD8αα+ skin-resident T cells in human herpes virus infection", Nature, 497(7450):494-7 and Corrigendum (2013). doi: 10.1038/nature12110. Epub May 8, 2013.

Zimmerman and Mannhalter. "Technical aspects of quantitative competitive PCR", Biotechniques, 21: 268-279 (1996).

\* cited by examiner

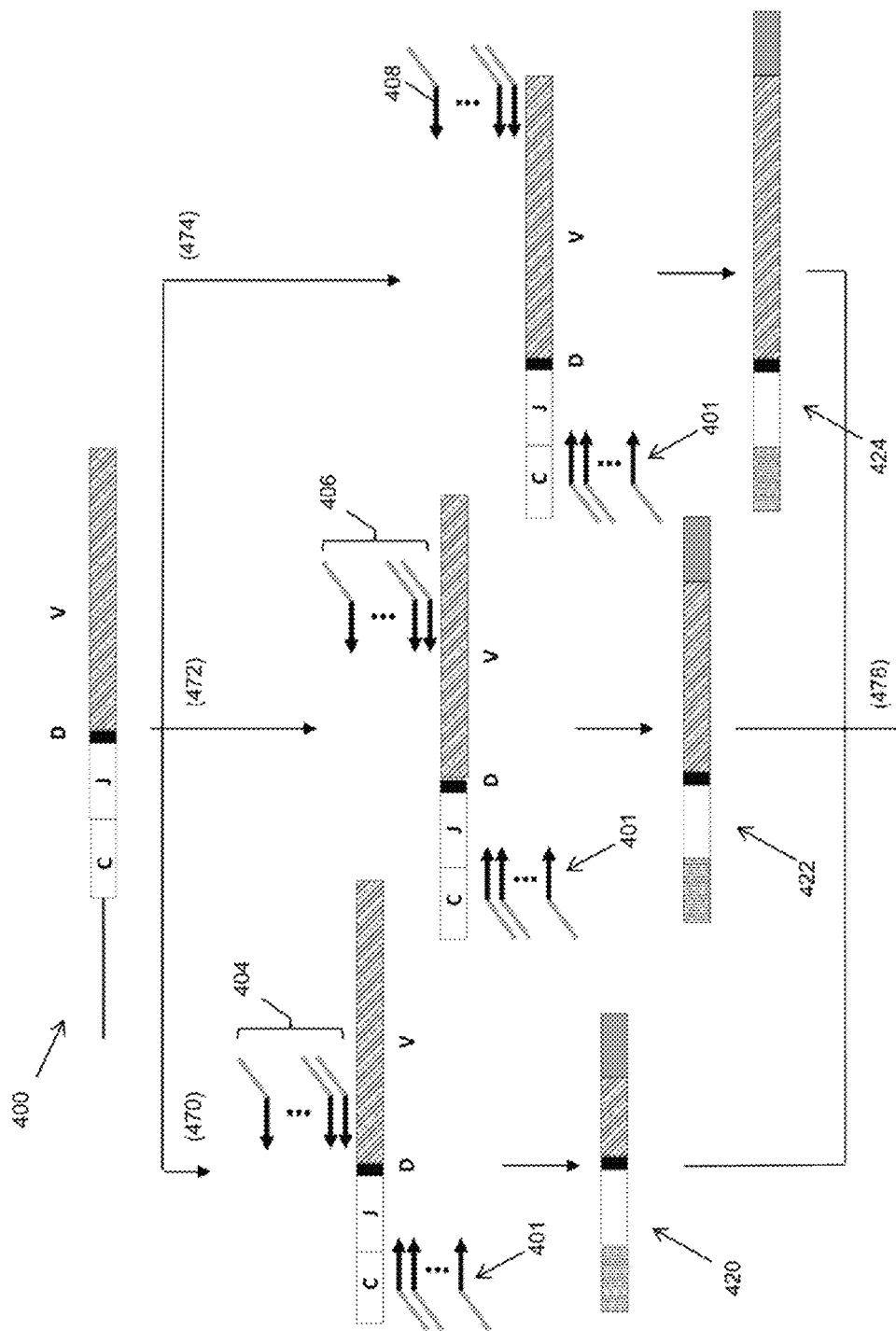

MONITORING IMMUNOGLOBULIN HEAVY CHAIN EVOLUTION IN B-CELL ACUTE LYMPHOBLASTIC LEUKEMIA

This application is a continuation-in-part of co-pending U.S. application Ser. No. 13/100,365 filed 4 May 2011, which claims priority from the following U.S. provisional patent applications: Ser. No. 61/332,175 filed 6 May 2010; Ser. No. 61/445,743 filed 23 Feb. 2011; Ser. No. 61/446,822 filed 25 Feb. 2011. U.S. patent application Ser. No. 13/100,365 is also a continuation-in-part of Ser. No. 12/615,263 filed 9 Nov. 2009 (now U.S. Pat. No. 8,236,503), which claims the benefit of Ser. No. 61/112,693, filed 7 Nov. 2008, each of the foregoing applications being incorporated herein by reference in its entirety.

This application also claims priority from U.S. provisional applications Ser. No. 61/636,518 filed 20 Apr. 2012; and Ser. No. 61/655,390 filed 4 Jun. 2012, each of the foregoing applications being incorporated herein by reference in its entirety.

BACKGROUND OF THE INVENTION

A feature of certain acute lymphoblastic leukemis (ALLs) is the sequence "evolution" of clonotypes associated with the disease. Although treatment outcomes in childhood acute lymphoblastic leukemias (ALL) have improved dramatically over the past fifty years, 10 to 15% of patients will ultimately relapse, usually with disease that is highly refractory to additional therapy, e.g. Pui et al, Lancet Oncol., 2:597-607 (2001); Pui et al, New Engl. J. Med., 350: 1535-1548 (2004); Tallen et al, J. Clin. Oncol., 28; 2339-2347 (2010). It is generally thought that these relapses are due to residual leukemic cells that are resistant to therapy and remain undetected during clinical remission. Several potential biological explanations tor the persistence of leukemic populations have been proposed, including the presence of multiple clones at diagnosis with varying susceptibilities to cytotoxic drugs or the outgrowth of resistant clones during treatment, e.g. Rosenquist et al, Eur. J. Haematol., 63: 171-179(1999).

Clonality of B-cell populations can be assessed by analysis of gene rearrangements that occur at the immunoglobulin heavy chain (IgH) gene locus. Early in B-cell development, somatic recombination at the IgH gene locus gives rise to unique rearrangements of the variable (VH), diversity (D), and joining (JH) gene segments, e.g. Tonegawa, Nature, 302: 575-581 (1983); Alt et al, Immunol. Today, 13: 306-314 (1992). In this two-step process, recombination signal sequences mediate D to JH joining, which is followed by VH to D-JH joining, e.g. Alt et al, EMBO J., 3: 1209-1219 (1984); Hiom et al, Cell, 88: 65-72 (1997); Hess et al, Genes Dev., 3: 1053-1061 (1989). During this recombination, non-templated nucleotides (N-bases) may be added at the junctions between gene segments, and other nucleotides may be deleted from the VH, D, and JH germline sequences, Alt et al, Proc. Natl. Acad. Sci., 79: 4118-4122 (1982). The resulting unique VHDJH rearrangements are used as clonotypic markers in precursor-B-cell ALL.

Precursor-B-cell ALL is generally thought to be a clonal disease resulting from malignant transformation and expansion of a single B-cell, e.g. Steenbergen et al, Leukemia, 1 I: 1258-1265 (1997). PCR-based methods have, however, shown changes in clonal IgH rearrangements between initial diagnosis and relapse in a significant proportion of pre-B ALL cases, Beishuizen et al Blood, 83: 2238-2247 (1994); Li et al, Leukemia Research, 25: 1033-1045 (2001); Szczepanski et al, Blood, 99: 2315-2323 (2002). These changes at the IgH locus could represent the persistence of ancestral clones that later expand, or continued evolution of a. primary ancestral clone its the setting of genotoxic anti-neoplastic therapy.

Current methods of monitoring leukemia clonotypes are not well suited for detecting changes or evolution of the sequences of leukemic clonotypes. It would be highly advantageous for patterns suffering from such diseases if there were available methods for detecting and monitoring sequence changes or evolution of leukemic clonotypes.

SUMMARY OF THE INVENTION

The present invention is drawn to methods for diagnosing and monitoring sequence evolution of IgH clonotypes in childhood ALL, particularly precursor B cell ALL. The invention is exemplified in a number of implementations and applications, some of which are summarized below and throughout the specification.

In one aspect the invention is directed to methods for monitoring and treating a patient suffering from a B cell proliferative disorder, such as, acute lymphoblastic leukemia using one or more patient-specific clonotypes correlated with the B cell disorder, wherein such methods comprise the following steps: (a) obtaining from the patient a sample comprising B-cells; (b) amplifying molecules of nucleic acid from the B-cells of the sample, the molecules of nucleic acid comprising or derived from recombined DNA sequences from immunoglobulin genes; (c) sequencing the amplified molecules of nucleic acid to form a clonotype profile; and (d) determining from the clonotype profile a presence, absence and/or level of the one or more patient-specific clonotypes correlated with the lymphoid proliferative disorder and previously unrecorded clonotype clonally evolved therefrom by $V_H$ substitution. In some embodiments, methods of the invention further include a step of modifying a treatment regimen of a patient based on a presence, absence and/or level of She one or more patient-specific clonotypes and clonotypes related thereto by VH substitutions.

The invention provides sequencing-based methods for monitoring clonotypes correlated with B cell leukemias and their clonally evolved progeny. In any lymphoid proliferative disorders associated with clonal evolution of correlating or index clonotypes, the invention advantageously overcomes deficiencies in prior art methods which lack, capability of detecting and measuring evolved clonotypes and thereby reduces She likelihood of patients inadvertently being harmed by false negative assessments of disease remission.

BRIEF DESCRIPTION OF THE DRAWINGS

The novel features of the invention are set forth with particularity in the appended claims. A better understanding of the features and advantages of the present invention is obtained by reference to the following detailed description that sets forth illustrative embodiments, in which the principles of the invention are utilized, and the accompanying drawings of which:

FIG. 38 illustrates details of another embodiment of determining a nucleotide sequence of the PCR product of FIG. 2C.

FIGS. 4B-4C illustrates a PCR scheme for generating three sequencing templates from an IgH chain in three separate reactions after which the resulting amplicons are combined for a secondary PCR to add P5 and P7 primer binding sites.

DETAILED DESCRIPTION OF THE INVENTION

Figure 1A:
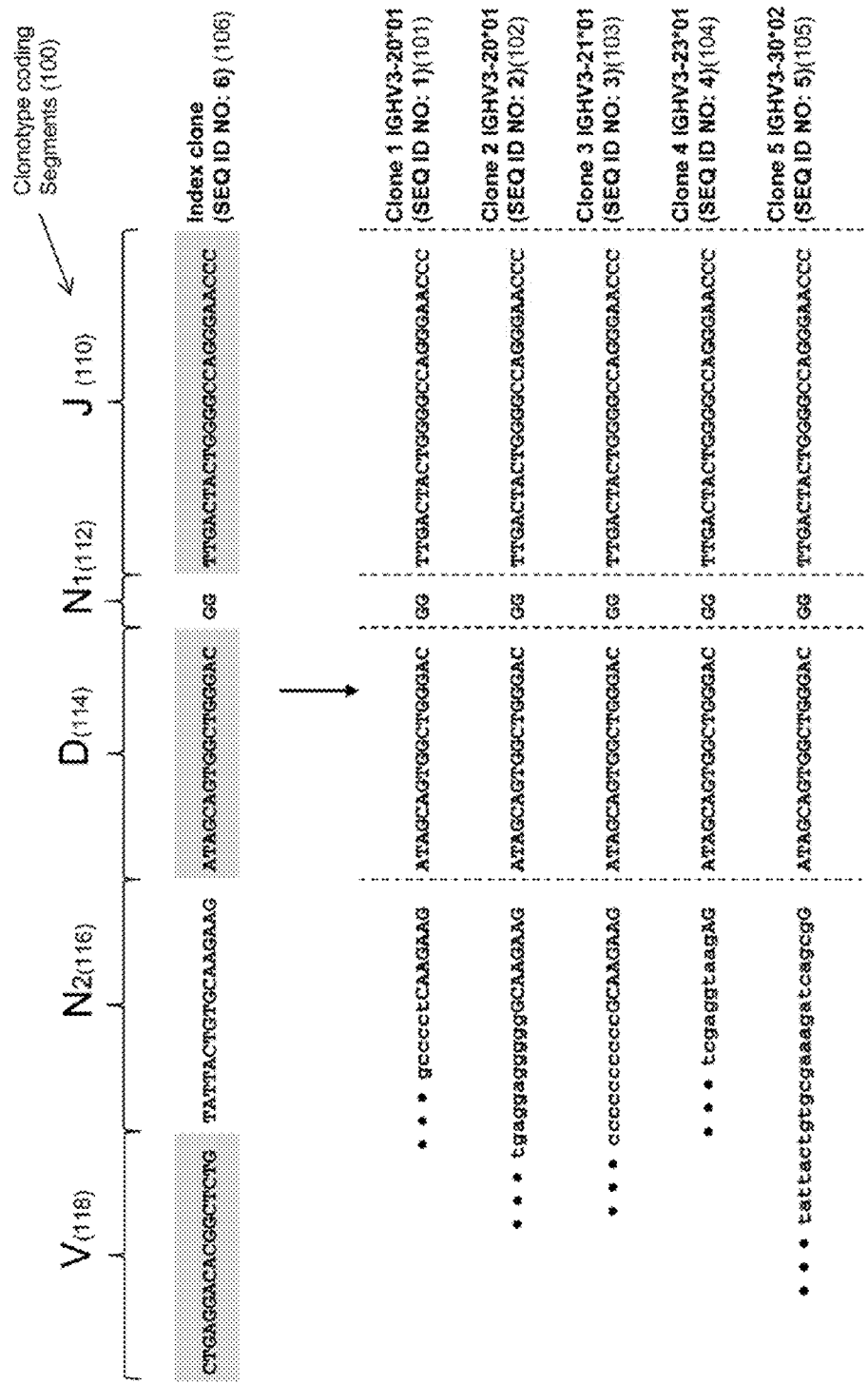
FIG. 1A diagrammatically shows sequences of clonotypes evolved from an index clone of patient 23.

The practice of the present invention may employ, unless otherwise indicated, conventional techniques and descriptions of molecular biology (Including recombinant techniques), bioinformatics, cell biology, and biochemistry, which are within the skill of the art. Such conventional techniques include, but are not limited to, sampling and analysis of blood cells, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV); *PCR Primer: A Laboratory Manual; and Molecular Cloning: A Laboratory Manual* (all from Cold Spring Harbor Laboratory Press); and the like.

The invention is directed to methods of monitoring B-cell lymphoid proliferative disorders by measuring the presence, absence and/or levels of correlating, or index, clonotypes and related clonotypes that have evolved therefrom, e.g. as part of me disease condition. The invention also includes methods of using such monitoring information to make treatment decisions for patients suffering from such disorders. In one aspect, the invention provides methods for monitoring B cell leukemias, and more particularly, B cell acute lymphoblastic leukemias, or B cell ALLs. In some embodiments, methods of the invention are directed to monitoring and/or Heating childhood B cell ALL, particularly childhood B precursor ALL. In another aspect, the invention provides a sequencing-based assay for detecting and measuring clonotypes, particularly previously unrecorded clonotypes, that have evolved from correlating or index clonotypes of a disease, e.g. determined in a diagnostic sample from a patient, to some embodiments, clonotypes being monitored comprise a VDJ region (or a portion thereof) encoding a heavy chain of an immunoglobulin (IgH) (or a portion thereof). In some embodiments, evolution from correlating (or index) IgH clonotypes occurs by "VH substitution;" that is, evolved clonotypes differ from a correlating or index IgH clonotype by substitution of a V-encoding region (possibly along with other nucleotides in the NDN region, as described more fully below). Biological mechanisms responsible for VH substitution may vary, e.g. Gawad et at Blood, 120(22): 4407-4417 (2012). The term "VH substitution" includes clonotypes formed by "VH replacement" (which refers to VH substitution by a particular mechanism) as well as those formed by VH changes by other mechanisms. In part, the invention is based oh a recognition and appreciation of a variety of models or algorithms for determining clonotypes that are related to a correlating, or index, clonotype by VH substitution.

Indentifying Clonotypes Evolved By VH Substitution

In some embodiments of the invention, a step of determining the presence, absence and/or level of evolved clonotypes includes comparing nucleotide sequences of clonotypes of a clonotype profile with the sequences of correlating (or index) clonotypes, and in some embodiments, sequences of previously recorded clonotypes evolved therefrom (collectively, "prior correlating clonotypes"). On the basis of such a sequence comparison, a clonotype in the profile is classified as clonally evolved from a prior correlating clonotypes by VH substitution. The manner in which such clonotype-clonotype comparisons are carried may vary widely with respect to which sequences are compared and how much extraneous data is employed, e.g. data regarding the likelihoods of the occurrences of particular sequences based on databases of clonotype sequences from populations of individuals. In some embodiments, such populations comprise individuals afflicted with a B cell ALL.

In some embodiments, the step of comparing includes determining whether the J segments of each prior correlating clonotype and each clonotype of a clonotype profile of a current sample ("sample clonotype") are the same. If they are not the same, then the next sample clonotype is selected and compared to the prior correlating clonotype. After every sample clonotype has been compared and classified, then the next prior correlating clonotype is selected and compared to each sample clonotype. Such a process leads to she formation of a first subset of sample clonotypes that each have a J segment identical to that of at least one prior correlating clonotype. Similar segment-to-segment comparisons may be carried out for $N_1$ and D segments. Those sample clonotypes that have J, $N_1$ and D segments identical, to those of at least one prior correlating clonotype, but which have a different V segment, may be classified as clonally evolved from a prior correlating clonotype by VH substitution. In other embodiments, the step of comparing may be implemented by comparing nucleotide sequences, or a combination of nucleotide sequences and segment identities.

In still other embodiments, a comparing step may be implemented as follows (referred to herein as the "6-base" algorithm): it is assumed that each base of the NDN sequences is independently distributed with each base having a 25% probability of occurring. The NDN region is ordered from the end of its $J_H$ segment toward its $V_H$ segment, and the number of consecutive matches from the $J_H$-NDN boundry is measured. Six consecutive identical bases in such a comparing step are required to reach a conclusion that a sample clonotype is evolved front a prior correlating clonotype, with significance of p=0.0001. The bases in the D segment come from a limited number of available alleles (so that the assumption of random nucleotides in such segments does not hold). Analysis of 8235 clonotypes from one of the CLL controls (described below) using the IMGT JunctionAnalysis tool showed a 6% probability of any two clonotypes sharing a D segment. This roughly corresponded to the probability of matching two consecutive bases (1/16 or 0.0625), so the D segments are represented as two effective NDN bases. Thus, in these embodiments, a sample clonotype and a prior correlating clonotype are classified as evolutionarily related by VH substitution if they have (i) identical J regions, (ii) at least six nucleotides beginning from the NDN-J boundary and extending to the VH direction that are identical, and (iii) identical D regions (as represented by a two-letter code).

In additional embodiments, a comparing step may make use of a probability model of the occurrences of the various components of the sample clonotypes and prior correlating clonotypes. In one such model, both information obtained directly from the sample clonotypes and prior correlating clonotypes and information about clonotypes obtained from databases is employed to classify sample clonotypes as evolved from prior correlating clonotypes or not. In one embodiment, the following direct information is used: (1) J segment identity and J segment deletions, (2) NDN sequence, and (3) V segment identity and V segment deletions. The following additional information about correlating clonotypes in the disease of interest may include (a) D segment identity, (b) position of the D segment (within the NDN region), and (c) deletions in the D segment from both the V direction ("V-side deletions") and the J direction ("J-side deletions"). In one embodiment, such information includes likelihoods of occurrence of the foregoing components from which sample clonotypes may be classified using a Bayesian model.

Monitoring Lymphoid Diseases And Treatment

Patients treated for many cancers often retain a minimal residual disease (MRD) related to the cancer. That is, even though a patient may have by a clinical measure a complete remission of the disease in response to treatment, a small fraction of the cancer cells may remain that have, for one reason or another, escaped destruction. The type and size of this residual population is an important prognostic factor for the patient's continued treatment, e.g. Campana, Hematol. Oncol. Clin. North Am., 23(5): 1083-1098 (2009); Buccisano et al, Blood, 119(2): 332-341. (2012).

In one aspect, the invention is directed to methods for monitoring minimal residual disease of a B-cell ALL after treatment, where the result of such monitoring is a key factor in determining whether to continue, discontinue or otherwise modify treatment. This aspect of the invention overcomes deficiencies in prior art methods because methods of the invention permit the detection and quantification of clones that have evolved from one or more originally identified disease-related clones (for example, identified at diagnosis by a variety of techniques, including but not limited to, analysis of a sequencing-based clonotype profile, an immunoscope profile confirmed by sequencing clonotypes, or by other methods, e.g. Pilarski et al, U.S. Pat. No. 6,416,948). The invention achieves the above objective in part by using sequencing-based clonotype profiles as the basic, monitoring measurement.

In many malignant lymphoid and myeloid neoplasms, a diagnostic tissue sample, such as a peripheral blood sample or a bone marrow sample, is obtained before treatment from which a clonotype profile is generated (a "diagnostic clonotype profile"). One or more disease-correlated clonotypes (i.e. "correlating clonotypes" or "index clonotypes") are identified in the clonotype profile, usually as the clonotypes having the highest frequencies, e.g. >5 percent. After treatment, the presence, absence or frequency of such correlating clonotypes is assessed periodically to determine whether a remission is holding or whether the neoplasm is returning or relapsing, based on the presence of, or an increase in the frequency of, the correlating clonotypes (or related clonotypes) in a post-treatment clonotype profile. That is, after treatment, minimal residual disease of the cancer is assessed based on the presence, absence or frequency of the correlating clonotypes and/or related clonotypes, such as clonotypes evolved therefrom by VH substitution, or other mechanisms, in one aspect of the invention, a measure of MRD is taken as a frequency of the one or more clonotypes initially identified as being correlated with the cancer together with the clonotypes evolved therefrom after such initial identification.

Treatment of childhood ALL is typically done in the following phases: (1) Induction therapy: This is the first phase of treatment. The goal is to kill the leukemia cells in the blood and bone marrow. This puts the leukemia into remission. This is also called the remission induction phase. (2) Consolidation/intensification therapy; This is the second phase of therapy. It begins once the leukemia is in remission. The goal of consolidation/intensification therapy is to kill any remaining leukemia cells that may not be active but could begin to regrow and cause a relapse. (3) Maintenance therapy: This is the third phase of treatment. The goal is to kill any remaining leukemia cells that may regrow and cause a relapse. Often the cancer treatments are given in lower doses than those used for induction and consolidation/intensification therapy. Usually induction therapy for ALL is carried out with chemotherapy with a combination of agents, such as vincristine, methotrexate, adrianmycin, daunorubicin, cytarabine, or the like, and a glucocorticoid, and possibly additional agents, such as asparaginase, e.g. Graynon et al, Chapter 141a, in Cancer Medicine, vol. 2 (BC Dekker, London, 2003). la the course of the three phases, in some cases, radiation therapy and/or stem cell transplant therapty is also employed. Stem cell transplant is a method of giving high doses of chemotherapy and sometimes radiation therapy, and then replacing the blood-forming cells destroyed by the cancer treatment Stem cells (immature blood cells) are removed from the blood or bone marrow of a donor. After the patient receives treatment, the donor's stem cells are given to the patient through an infusion. These reinfused stem cells grow into (and restore) the patient's blood cells.

MRD measurements are used to assess the efficacy of the above treatment modalities. If increased numbers of leukemia cells are detected (e.g. between successive MRD measurements), then a relapse has taken place and the treatment regimen is modified to regain a remissive state. The modification may include use of a different chemotherapeutic combination, use of a different administration schedule, use of different amounts of drug, or a switch to a differ kind of therapy, e.g. from chemotherapy to bone marrow transplant therapy. A method for treating a patient having a B cell acute lymphoblastic leukemia (ALL) comprises administering to the patient a therapeutically effective amount, of a anti-ALL agent. A therapeutically effective amount may vary depending on the nature of the anti-ALL agent. In one aspect, a therapeutically effective amount may be aliened depending on the level of MRD, e.g. as determined by a sequencing-based clonotype profile.

Exemplary anti-ALL chemotherapeutic agents include, but are not limited to, cisplatin, carboplatin, oxaliplatin, radiation, CPT-11, paclitaxel, 5-flourouracil, leucovorin, epothilone, gemcitabine, UFT, herceptin, cytoxan, dacarbaxine, ifosfamide, mechlorethamine, melphalan, chlorambucil, anastrozole, exemstane, carmustine, lomustine, methotrexate, gemcitabine, cytarabine, fludarabine, bleomycin, dactinomycin, daunorubicin, doxorubicin, idarubicin, docetaxel, vinblastine, vincristin, vinorelbine, topotecan, lupron, megace, leucovorin, Iressa, flavopiridol, immunomotherapeuiic agents, ZD6474, SU6668, and valspodar. Whenever the anti-ALL agent is a chemotherapeutic agent, it preferably is administered in a conventional pharmaceutical carrier. The pharmaceutical carrier may be solid or liquid. A solid carrier can include one or more substances which may also act as flavoring agent, lubricants, solubilizers, suspending agents, fillers, glidants, compression aids, binders or table-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Liquid carriers are used in preparing solutions, suspensions, emulsions, syrups, elixirs and pressurized composition. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agent, colors, viscosity regulators, stabilizers or osmo-regulators. Suitable examples of liquid carriers for oral and parenteral administration include water (partially containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can also be an oily ester such as ethyl oleate and iopropyl myristate. Sterile liquid carriers are useful in sterile liquid form compositions for parenteral administration. The liquid carrier for pressurized compositions can be halogenated hydrocarbon or other pharmaceutically acceptable propellent. Liquid pharmaceutical compositions which are sterile solutions or suspensions can be utilized by, for example, intramuscular, intraperitoneal or subcutaneous injection. Sterile solutions can also be administered intravenously. The therapeutic agent can also be administered orally either in liquid or solid composition form.

Samples

Clonotype profiles for the method of the invention are generated from a sample of nucleic acids extracted from a sample containing B cells, B-cells include, for example, plasma B cells, memory B cells, B1 cells, B2 cells, marginal-zone B cells, and follicular B cells. B-cells can express immunoglobulins (antibodies, B cell receptor), in one aspect a sample of B cells includes at least 1,000 B cells; but more typically, a sample includes at least 10,000 8 cells, and more typically, at least 100,000 B cells. In another aspect, a sample includes a number of B cells in the range of from 1000 to 1,000,000 B cells. Adequate sampling of the cells is an important aspect of interpreting the repertoire data, as described further below in the definitions of "Clonotype" and "repertoire." The member of cells in a sample sets a limit on the sensitivity of a measurement. For example, in a sample containing 1,000 B cells, the lowest frequency of clonotype detectable is $1/1000$ or 0.001, regardless of how many sequencing reads are obtained when the DNA of such cells is analyzed by sequencing.

The sample can include nucleic acid, for example, DNA (e.g., genomic DNA or mitochondrial DNA) or RNA (e.g., messenger RNA of microRNA), The nucleic acid can be cell-free DNA or RNA, e.g. extracted from the circulatory system, Vlassov et al, Curr. Mol. Med., 10: 142-165 (2010); Swarup et al, FEBS Lett., 581: 795-799 (2007). In the methods of the provided invention, the amount of RNA or DNA from a subject that can be analyzed includes, for example, as low as a single cell in some applications (e.g., a calibration test) and as many as 10 million of cells or more translating, to a range of DNA of 6 pg-60 ug, and RNA of approximately 1 pg-10 ug.

As discussed more fully below (Definitions), a sample of lymphocytes is sufficiently large so that substantially every B cell with a distinct clonotype is represented therein, thereby forming a repertoire (as the terra is used herein). In one embodiment, a sample is taken, that contains with a probability of ninety-nine percent every clonotype of a population present at a frequency of 0.001 percent or greater. In another embodiment, a sample is taken that contains with a probability of ninety-nine percent every clonotype of a population present at a frequency of 0.0001 percent or greater. In one embodiment, a sample of B cells includes at least a half million cells, and in another embodiment such sample includes at least one million cells.

Whenever a source of material from which a sample is taken is scarce, such as, clinical study samples, or the like, DNA from the material may be amplified by a non-biasing technique prior to specific amplification of BCR encoding sequences, such as whole genome amplification (WGA), multiple displacement amplification (MDA); or like technique, e.g. Hawkins et al, Curr. Opin. Biotech., 13: 65-67 (2002); Dean et al, Genome Research, 11: 1095-1099 (2001); Wang et al, Nucleic Acids Research 32; e76 (2004); Hosono et al, Genome Research, 13: 954-964 (2003); and the like.

Blood samples are of particular interest and may be obtained using conventional techniques, e.g. Innis et al, editors, PCR Protocols (Academic Press, 1990); or the like. For example, white blood cells may be separated from blood samples using convention techniques, e.g. RosetteSep kit (Stem Cell Technologies, Vancouver, Canada). Blood samples may range in volume from 100 μL to 10 mL; in one aspect, blood sample volumes are in the range of from 100 μL to 2 mL. DNA and/or RNA may then be extracted from such blood sample using conventional techniques for use in methods of the invention, e.g. DNeasy Blood & Tissue Kit (Qiagen, Valencia, Calif.). Optionally, subsets of white blood cells, e.g. lymphocytes, may be further isolated using conventional techniques, e.g. fluorescently activated cell sorting (FACS)(Beeton Dickinson, San Jose, Calif.), magnetically activated cell sorting (MACS)(Miltenyi Biotec, Auburn, Calif.), or the like. For example, memory B cells may be isolated by way of surface markers CD19 and CD27.

Since the identifying recombinations are present in the DNA of each individual's adaptive immunity cell as well as their associated RNA transcripts, either RNA or DNA can be sequenced in the-methods of the provided invention. A recombined sequence from a B-cell encoding an immunoglobulin molecule, or a portion thereof is referred to as a clonotype. The DNA or RNA can correspond to sequences from immunoglobulin (Ig) genes that encode antibodies.

The DNA and RNA analyzed in the methods of the invention correspond to sequences encoding heavy chain immunoglobulins (IgH). Each chain is composed of a constant (C) and a variable region. For the heavy chain, the variable region is composed of a variable (V), diversity (D), and joining (J) segments. Several distinct sequences coding for each type of these segments are present in the genome. A specific VDJ recombination event occurs during the development of a B-cell, marking that cell to generate a specific heavy chain. Somatic mutation often occurs close to the site of the recombination, causing the addition or deletion of several nucleotides, further increasing the diversity of heavy chains generated by B-cells. The possible diversity of the antibodies generated by a B-cell is then the product of the different heavy and light chains. The variable regions of tie heavy and light chains contribute to form the antigen recognition (or binding) region or site. Added to this diversity is a process of somatic hypermutation which can occur after a specific response is mounted against some epitope.

In accordance with the invention, primers may be selected to generate amplicons of recombined nucleic acids extracted from B lymphocytes. Such, sequences may be referred to herein as "somatically rearranged regions," or "somatically recombined regions," or "recombined sequences." Somatically rearranged regions may comprise nucleic acids from developing or from fully developed lymphocytes where developing lymphocytes are cells in which rearrangement of immune genes has not been completed to form molecules having full V(D)J regions. Exemplary incomplete somatically rearranged regions include incomplete IgH molecules (such as, molecules containing only D-J regions).

Amplification of Nucleic Acid Populations

As noted below, amplicons of target populations of nucleic acids may be generated by a variety of amplification techniques. In one aspect of the invention, multiplex PCR is used to amplify members of a mixture of nucleic acids, particularly mixtures comprising recombined immune molecules such as T cell receptors, B cell receptors, or portions thereof. Guidance for carrying out multiplex PCRs of such immune molecules is found in the following references, which are incorporated by reference: Faham et al, U.S. patent publication 2011/0207134: Lim et al, U.S. patent publication 2008/0166718; and the like. As described more fully below, in one aspect, the step of spatially isolating individual nucleic acid molecules is achieved by carrying out a primary multiplex amplification of a preselected somatically rearranged region or portion thereof (i.e. target sequences) using forward and reverse primers that each have tails non-complementary to the target sequences to produce a first amplicon whose member sequences have common sequences at each end that allow further manipulation. For example, such common ends may include primer binding sites for continued amplification using just a single forward primer and a single reverse primer instead of multiples of each, or for bridge amplification of individual molecules on a solid surface, or the like. Such common ends may be added in a single amplification as described above, or they may be added in a two-step procedure to avoid difficulties associated with manufacturing and exercising quality control over mixtures of long primers (e.g. 50-70 bases or more). In such a two-step process (described more fully below), the primary amplification is carried out as described above, except that the primer tails are limited in length to provide only forward and reverse primer binding sites at the ends of the sequences of the first amplicon. A secondary amplification is then carried out using secondary amplification primers specific to these primer binding sites to add further sequences to the ends of a second amplicon. The secondary amplification primers have tails non-complementary to the target sequences, which form the ends of the second amplicon and which may be used in connection with sequencing the clonotypes of the second amplicon. In one embodiment, such added sequences may include primer binding sites for generating sequence reads and primer binding sites for carrying out bridge PCR on a solid surface to generate clonal populations of spatially isolated individual molecules, for example, when Solexa-based sequencing is used. In this latter approach, a sample of sequences from the second amplicon are disposed on a solid surface that has attached complementary oligonucleotides capable of annealing to sequences of the sample, after which cycles of printer extension, denaturation, annealing are implemented until clonal populations of templates are formed. Preferably, the size of the sample is selected so that (i) it includes an effective representation of clonotypes in the original sample, and (ii) the density of clonal populations on the solid surface is in a range that permits unambiguous sequence determination of clonotypes.

The region to be amplified can include the full clonal sequence or a subset of the clonal sequence, including the V-D junction, D-J junction of an immunoglobulin gene, the fall variable region of an immunoglobulin, the antigen, recognition region, or a CDR, e.g., complementarity determining region 3 (CDR3).

After amplification of DNA from the genome (or amplification of nucleic acid in the form of cDNA by reverse transcribing RNA), the individual nucleic acid molecules can be isolated, optionally re-amplified, and then sequenced individually. Exemplary amplification protocols may be round in van Dongen et al, Leukemia, 17: 2257-2317 (2003) or van Dongen et al, U.S. patent publication 2006/0234234, which is incorporated by reference. Briefly, an exemplary protocol is as follows: Reaction buffer: ABI Buffer II or ABI Gold Buffer (Life Technologies, San Diego, Calif.); 50 µL final reaction volume; 100 ng sample DNA; 10 pmol of each primer (subject to adjustments to balance amplification as described below); dNTPs at 200 µM final concentration; $MgCl_2$ at 1.5 mM final concentration (subject to optimization depending on target sequences and polymerase); Taq polymerase (1-2 U/tube); cycling conditions: preservation 7 min at 95 oC; annealing at 60 oC; cycling times; 30 s denaturation; 30 s annealing; 30 s extension. Polymerases that can be used for amplification in the methods of the invention are commercially available and include, for example, Taq polymerase, AccuPrime polymerase, or Pfu. The choice of polymerase to use can be based on whether fidelity or efficiency is preferred.

Methods for isolation of nucleic acids from a pool include subcloning nucleic acid into DNA vectors and transforming bacteria (bacterial cloning), spatial separation of the molecules in two dimensions on a solid substrate (e.g., glass slide), spatial separation of the molecules in three dimensions in a solution within micelles (such as can be achieved using oil emulsions with or without immobilizing the molecules on a solid surface such as beads), or using microreaction chambers in, for example, microfluidic or nano-fluidic chips. Dilution can be used to ensure that on average a single molecule is present in a given volume, spatial region, bead, or reaction chamber. Guidance for such methods of isolating individual nucleic acid molecules is found In the following references; Sambrook, Molecular Cloning: A Laboratory Manual (Cold Spring Harbor Laboratory Press, 2001s); Shendure et al, Science, 309: 1728-1732 (including supplemental material) (200S); U.S. Pat. No. 6,300,070; Bentley et al, Nature, 456: 53-59 (including supplemental material)(2008); U.S. Pat. No. 7,323,305; Matsubara et al, Biosensors & Bioelectronics, 20: 1482-1490 (2005); U.S. Pat. No. 6,753,147; and the like.

Real time PCR, picogreen staining, nanofluidic electrophoresis (e.g. LabChip) or UV absorption measurements can be used in an initial step to judge the functional amount of amplifiable material.

In one aspect, multiplex amplifications are carried out so that relative amounts of sequences in a starting population are substantially the same as those in the amplified population, or amplicon. That is, multiplex amplifications are carried out with minimal amplification bias among member sequences of a sample population. In one embodiment, such relative amounts are substantially the same if each relative amount in an amplicon is within five fold of its value in the starting sample. In another embodiment, such relative amounts are substantially the same if each relative amount in an amplicon is within two ibid of its value in the starting sample. As discussed more fully below, amplification bias in PCR may be detected and corrected using conventional techniques so that a set of PCR primers may be selected for a predetermined repertoire that provide unbiased amplification of any sample.

In one embodiment, amplification bias may be avoided by carrying out a two-stage amplification (as described above) wherein a small number of amplification cycles are implemented in a first, or primary, stage using primers having tails non-complementary with the target sequences. The tails include primer binding sites that are added to the ends of the sequences of the primary amplicon so that such sites are used in a. second stage amplification using only a single forward primer and a single reverse primer, thereby eliminating a primary cause of amplification bias. Preferably, the primary PCR will have a small enough number of cycles (e.g. 5-10) to minimize the differential amplification by the different primers. The secondary amplification is done with one pair of primers and hence the issue of differential amplification is minimal. One percent of the primary PCR is taken directly to the secondary PCR. Thirty-five cycles (equivalent to ~28 cycles without the 100 Ibid dilution step) used between the two amplifications were sufficient to show a robust amplification irrespective of whether the breakdown of cycles were: one cycle primary and 34 secondary or 25 primary and 10 secondary. Even though ideally doing only 1 cycle in the primary PCR may decrease the amplification bias, there are other considerations. One aspect of this is representation. This plays a role when the starting input amount is not in excess to the number of reads ultimately obtained. For example, if 1,000,000 reads are obtained and starting with 1,000,000 input molecules then taking only representation front 100,000 molecules to the secondary amplification would degrade the precision of estimating the relative abundance of the different species in the original sample. The 100 ibid dilution between the 2 steps means that the representation is reduced unless the primary PCR amplification generated significantly more than 100 molecules. This indicates that a minimum 8 cycles (256 fold), but more comfortably 10 cycle (~1,000 fold), may be used. The alternative to that is to take more than 1% of the primary PCR into the secondary but because of the high concentration of primer used in the primary PCR, a big dilution factor is can be used to ensure these printers do not interfere in the amplification and worsen the amplification bias between sequences. Another alternative is to add a purification or enzymatic step to eliminate the primers from the primary PCR to allow a smaller dilution of it. In this example, the primary PCR was 10 cycles and the second 25 cycles.

Figure 2A:
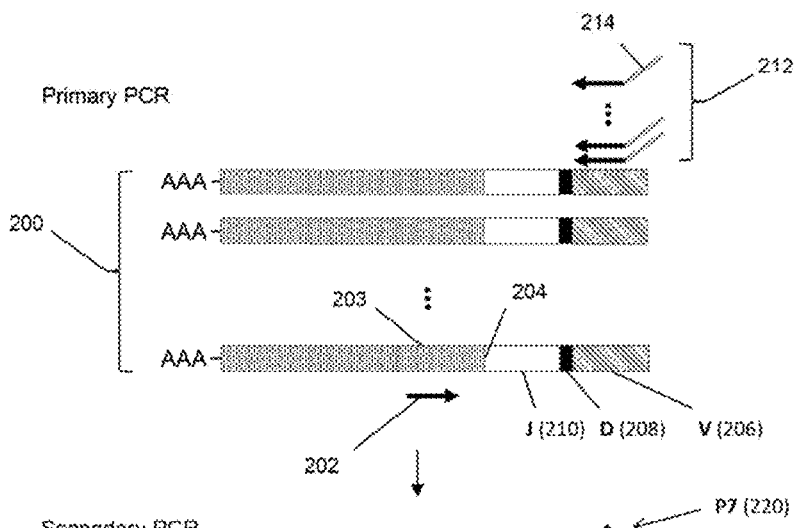
FIGS. 2A-2C show a two-staged PCR scheme for amplifying and sequencing immunoglobulin genes.
Figure 2B:
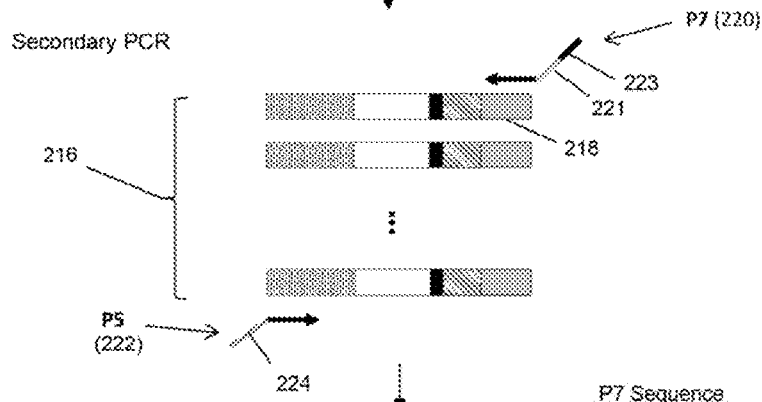
Figure 2C:
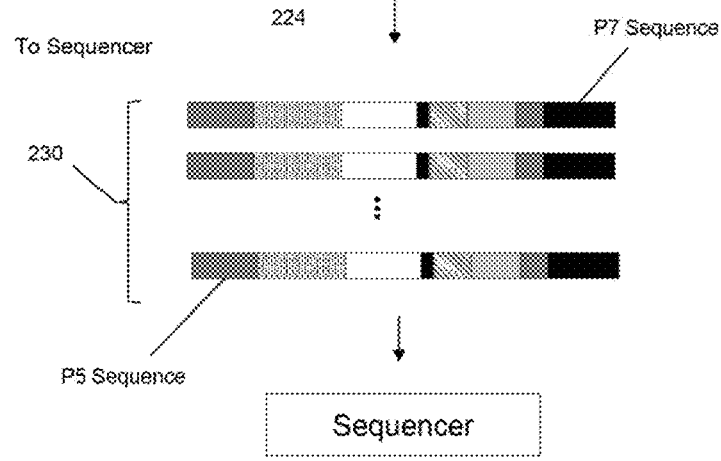

Briefly, the scheme of Faham and Willis (cited above) for amplifying IgH-encoding nucleic acids (RNA) is illustrated in FIGS. 2A-2C. Nucleic acids (200) are extracted from lymphocytes in a sample and combined in a PCR with a primer (202) specific For C region (203) and primers (212) specific for the various V regions (206) of the immunoglobulin genes. Primers (212) each have an identical tail (214) that provides a primer binding site for a second stage of amplification. As mentioned above, primer (202) is positioned adjacent to junction (204) between the C region (203) and J region (210). In the PCR, amplicon (216) is generated that contains a portion of C-encoding region (203), J-encoding region (210), D-encoding region (208), and a portion of V-encoding region (206). Amplicon (216) is farther amplified in a second stage using primer P5 (222) and primer P7 (220), which each have tails (225 and 221/223, respectively) designed for use in an Illumina DNA sequencer. Tail (221/223) of primer P7 (220) optionally incorporates tag (221) for labeling separate samples in the sequencing process. Second stage amplification produces amplicon (230) which may be used in an Illumina DNA sequencer.

Generating Sequence Reads for Clonotypes

Any high-throughput technique for sequencing nucleic acids can be used in the method of the invention. Preferably, such technique has a capability of generating in a cost-effective manner a volume of sequence data from which at least 1000 clonotypes can be determined, and preferably, from which at least 10,000 to 1,000,000 clonotypes can be determined. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of the separated molecules has more recently been demonstrated by sequential or single extension reactions using polymerases or ligases as well as by single or sequential differential hybridizations with libraries of probes. These reactions have been performed on many clonal sequences in parallel including demonstrations in current commercial applications of over 100 million sequences in parallel. In one aspect of the invention, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)). In another aspect, such methods comprise amplifying the isolated molecules either before or after they are spatially isolated on a solid surface. Prior amplification may comprise emulsion-based amplification, such as emulsion PCR, or rolling circle amplification. Of particular interest is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina. Inc., San Diego, Calif., 2010): and further in the following references: U.S. Pat. Nos. 6,090,592; 6,300,070; 7,115,400; and EP0972081B1; which, are incorporated by reference. In one embodiment, individual molecules disposed and amplified, on a solid surface form clusters in a density of at least $10^5$ clusters per $cm^2$; or in a density of at least $5\times10^5$ per $cm^2$; or in a density of at least $10^6$ clusters per $cm^2$. In one embodiment, sequencing chemistries are employed having relatively high error rates. In such embodiments, the average quality scores produced by such chemistries are monotonically declining functions of sequence read lengths. In one embodiment, such decline corresponds to 0.5 percent of sequence reads have at least one error in positions 1-75; 1 percent of sequence reads have at least one error in positions 76-100; and 2 percent of sequence reads have at least one error in positions 101-125.

In one aspect, a sequence-based clonotype profile of an individual is obtained using the following steps; (a) obtaining a nucleic acid sample from B-cells of the individual; (b) spatially isolating individual molecules derived from such nucleic acid sample, the individual molecules comprising at least one template generated from a nucleic acid in the sample, which template comprises a somatically rearranged region or a portion thereof, each individual molecule being capable of producing at least one sequence read; (c) sequencing said spatially isolated individual molecules; and (d) determining abundances of different sequences of the nucleic acid molecules from the nucleic acid sample to generate the clonotype profile. In one embodiment, each of the somatically rearranged regions comprise a V region and a J region. In another embodiment, the step of sequencing comprises bidirectionally sequencing each of the spatially isolated individual molecules to produce at least one forward sequence read and at least one reverse sequence read. Further to the latter embodiment, at least one of the forward sequence reads and at least one of the reverse sequence reads have an overlap region, such that bases of such overlap region are determined by a reverse complementary relationship between such sequence reads. In still another embodiment, each of the somatically rearranged regions comprise a V region and a J region and the step of sequencing further includes determining a sequence of each of the individual nucleic acid molecules from one or more of its forward sequence reads and at least one reverse sequence read starting from a position in a J region and extending in the direction of its associated V region. In another embodiment, individual molecules comprise nucleic acids selected from the group consisting of complete IgH molecules, incomplete IgH molecules. In another embodiment, the step of sequencing comprises generating the sequence reads having monotonically decreasing quality scores. Further to the latter embodiment, monotonically decreasing quality scores are such that the sequence reads have error rates no better than the following: 0.2 percent of sequence reads contain at least one error in base positions 1 to 50, 0.2 to 1.0 percent of sequence reads contain at least one error in positions 51-75, 0.5 to 1.5 percent of sequence reads contain at least one error in positions 76-100. In another embodiment, the above method comprises the following steps: (a) obtaining a nucleic acid sample from T-cells and/or B-cells of the individual; (b) spatially isolating individual molecules derived from such nucleic acid sample, the individual molecules comprising nested sets of templates each generated from a nucleic acid in the sample and each containing a somatically rearranged region or a portion thereof each nested set being capable of producing a plurality of sequence reads each extending in the same direction and each starting from a different position on the nucleic acid from which the nested set was generated: (c) sequencing said, spatially isolated individual molecules; and (d) determining abundances of different sequences of the nucleic acid molecules from the nucleic acid sample to generate the clonotype profile. In one embodiment, the step of sequencing includes producing a plurality of sequence reads for each of the nested sets. To another embodiment, each of the somatically rearranged regions comprise a V region and a J region, and each of the plurality of sequence reads starts from a different position in the V region and extends in the direction of its associated J region.

In one aspect, for each sample from an individual, the sequencing technique used in the methods of the invention generates sequences of least 1000 clonotypes per run; in another aspect, such technique generates sequences of at least 10,000 clonotypes per run; in another aspect, such technique generates sequences of at least 100,000 clonotypes per run; in another aspect, such technique generates sequences of at least 500,000 clonotypes per run; and in another aspect, such technique generates sequences of at least 1,000,000 clonotypes per run. In still another aspect, such technique generates sequences of between 100,000 to 1,000,000 clonotypes per run per individual sample.

The sequencing technique used in the methods of the provided invention can generate about 30 bp, about 40 bp, about 50 bp, about 60 bp, about 70 bp, about 80 bp, about 90 bp, about 100 bp, about 110, about 120 bp per read, about 150 bp, about 200 bp, about 250 bp, about 300 bp, about 350 bp, about 400 bp, about 450 bp, about 500 bp, about 550 bp, or about 600 bp per read.

Clonotype Determination from Sequence Data

Constructing clonotypes from sequence read data is disclosed in Faham and Willis (cited above), which is incorporated herein by reference. Briefly, constructing clonotypes from sequence read data depends in part on the sequencing method used to generate such data, as the different methods have different expected read lengths and data quality. In one approach, a Solexa sequencer is employed to generate sequence read data for analysis. In one embodiment, a sample is obtained that provides at least: $0.5$-$1.0\times10^6$ lymphocytes to produce at least 1 million template molecules, which after optional amplification may produce a corresponding one million or more clonal, populations of template molecules (or clusters). For most high throughput sequencing approaches, including the Solexa approach, such over sampling at the cluster level is desirable so that each template sequence is determined with a large degree of redundancy to increase the accuracy of sequence determination. For Solexa-based implementations, preferably the sequence of each independent template is determined 10 times or more. For other sequencing approaches with different expected read lengths and data qualify, different levels of redundancy may be used for comparable accuracy of sequence determination. Those of ordinary skill in. the art recognize that the above parameters, e.g. sample size, redundancy, and the like, are design choices related to particular applications.

Figure 3A:
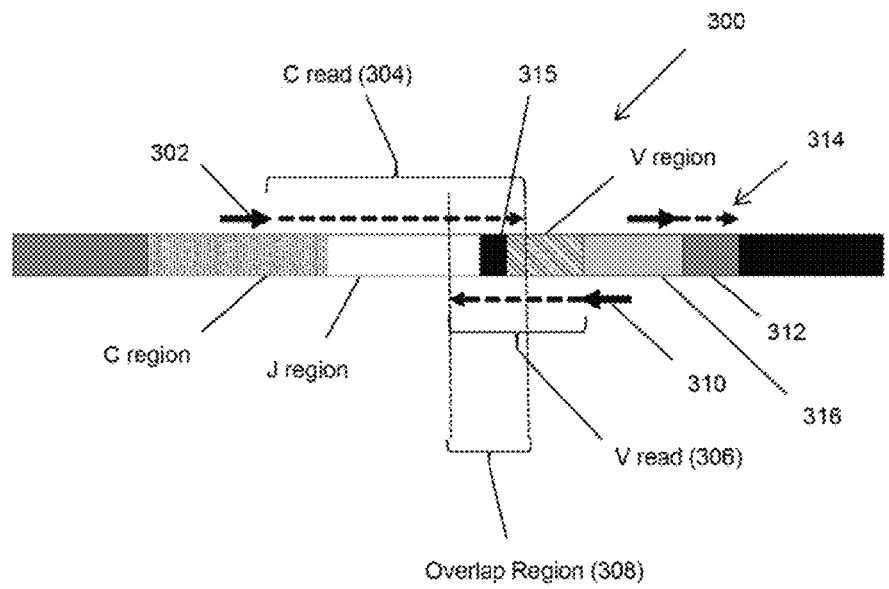
FIG. 3A illustrates details of one embodiment of determining a nucleotide sequence of the PCR product of FIG. 2C.
Figure 3B:
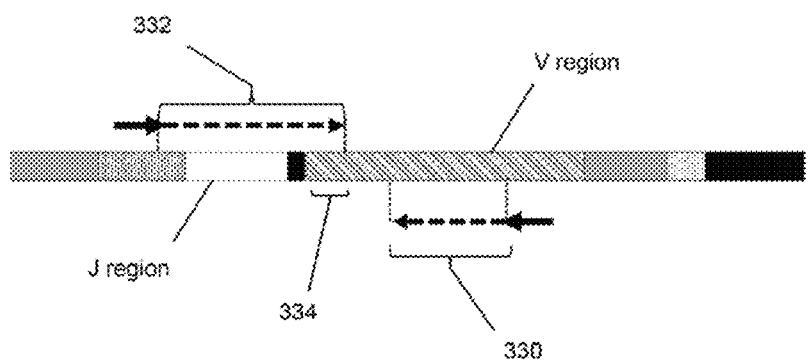

In one aspect, clonotypes of IgH chains (illustrated in FIG. 3A) are determined by at least one sequence read starting in its C region and extending in the direction of its associated V region (referred to herein as a "C read" (304)) and at least one sequence read starting in its V region and extending in the direction of its associated J region (referred to herein as a "V read" (306)). Such reads may or may not have an overlap region (308) and such overlap may or may not encompass the NDN region (315) as shown in FIG. 3A. Overlap region (308) may be entirely in the J region, entirely in the NDN region, entirely in the V region, or it may encompass a J region-NDN region boundary or a V region-NDN region boundary, or both such boundaries (as illustrated in FIG. 3A). Typically, such sequence reads are generated by extending sequencing primers, e.g. (302) and (310) in FIG. 3A, with a polymerase in a sequencing-by-synthesis reaction, e.g. Metzger, Nature Reviews Genetics, 11: 31-46 (2010); Fuller et al, Nature Biotechnology, 27: 1013-1023 (2009). The binding sites for primers (302) and (310) are predetermined, so that they can provide a starting point or anchoring point for initial alignment and analysis of the sequence reads. In one embodiment, a C read is positioned so that it encompasses the D and/or NDN region of the IgH chain and includes a portion of the adjacent V region, e.g. as illustrated in FIGS. 3A and 3B. In one aspect, the overlap of the V read and the C read in the V region is used to align the reads wish one another. In other embodiments, such alignment of sequence reads is not necessary, so that a V read may only be long enough to identify the particular V region of a clonotype. This latter aspect is illustrated in FIG. 3B. Sequence read (330) is used to identify a V region, with or without overlapping another sequence read, and another sequence read (332) traverses the NDN region and is used to determine the sequence thereof. Portion (334) of sequence read (332) that extends into the V region is used to associate the sequence information of sequence read (332) with that of sequence read (330) to determine a clonotype. For some sequencing methods, such as base-by-base approaches like the Solexa sequencing method, sequencing run time and reagent costs are reduced by minimizing the number of sequencing cycles in an analysis. Optionally, as illustrated in FIG. 3A, amplicon (300) is produced with sample tag (312) to distinguish between clonotypes originating from different biological samples, e.g. different patients. Sample tag (312) may be identified by annealing a primer to primer binding region (316) and extending it (314) to produce a sequence read across tag (312), from which sample tag (312) is decoded.

Figure 4A:
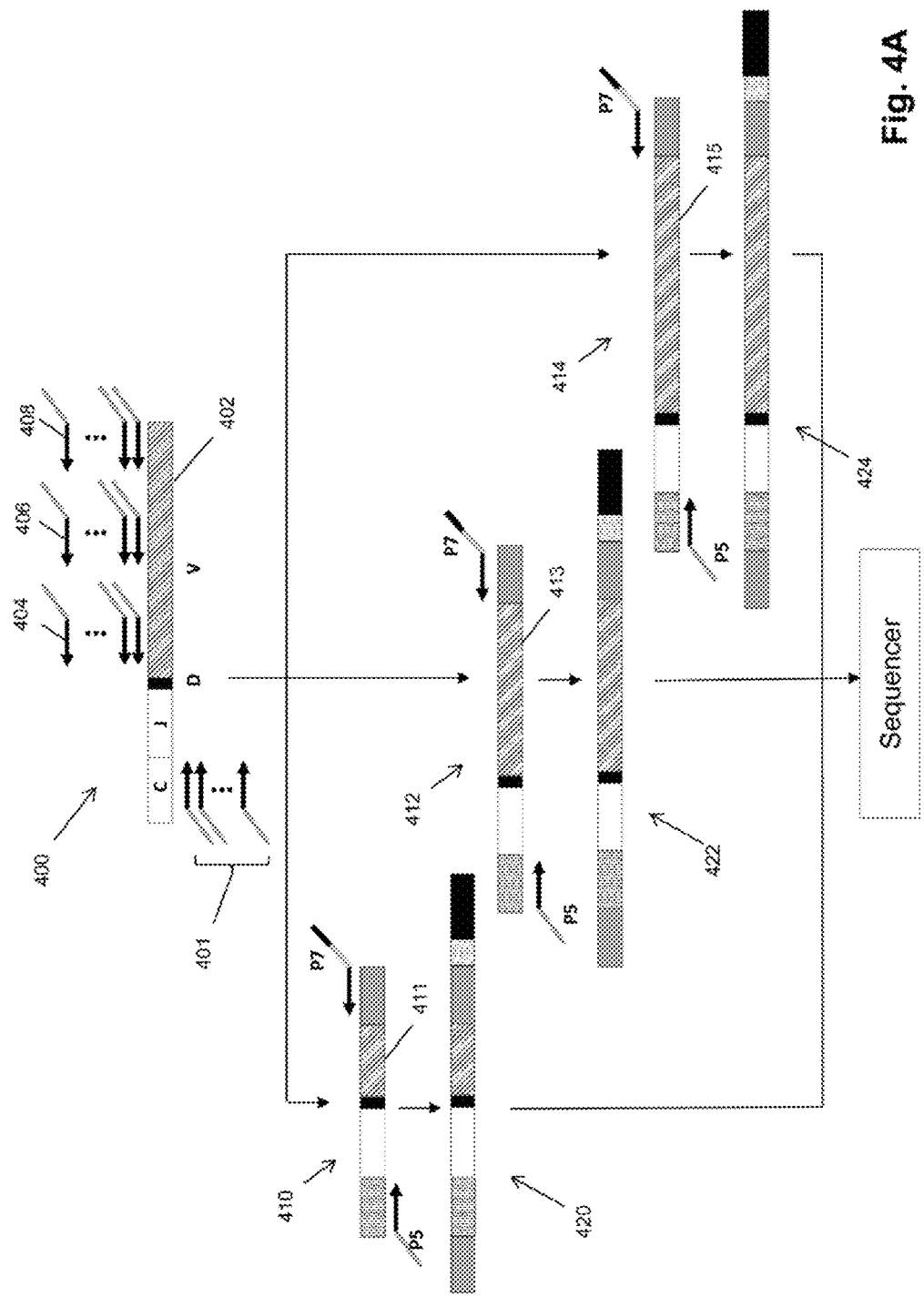
FIG. 4A illustrates a PCR scheme for generating three sequencing templates from an IgH chain in a single reaction.
Figure 4C:
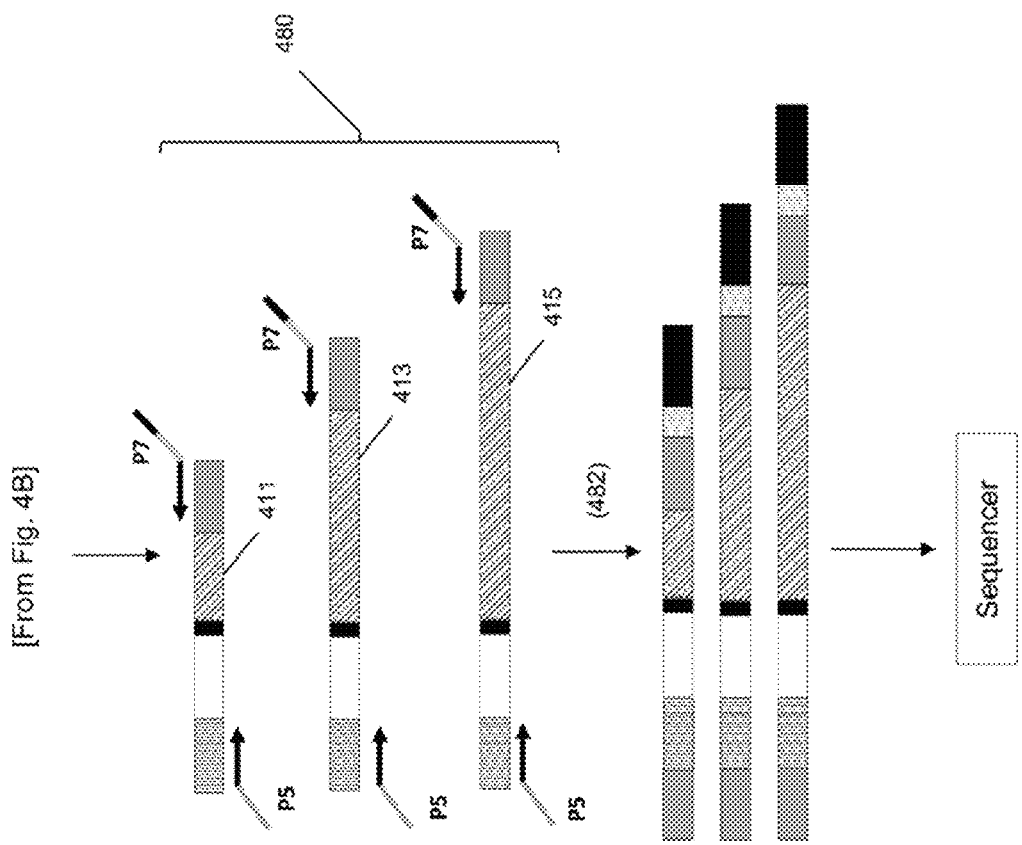

In one aspect of the invention, sequences of clonotypes may be determined by combining information from one or more sequence reads, for example, along the V(D)J regions of the selected chains. In another aspect, sequences of clonotypes are determined by combining information from a plurality of sequence reads. Such pluralities of sequence reads may include one or more sequence reads along a sense strand (i.e. "forward" sequence reads) and one or more sequence reads along its complementary strand (i.e. "reverse" sequence reads). When multiple sequence reads are generated along the same strand, separate templates are first generated by amplifying sample molecules with primers selected for the different positions of the sequence reads. This concept is illustrated in FIG. 4A where primers (404, 406 and 408) are employed to generate amplicons (410, 412, and 414, respectively) in a single reaction. Such amplifications may be carried out in the same reaction or in separate reactions. In one aspect, whenever PCR is employed, separate amplification reactions are used for generating the separate templates which, in turn, are combined and used to generate multiple sequence reads along the same strand. This tatter approach is preferable for avoiding the need to balance primer concentrations (and/or other reaction parameters) to ensure equal amplification of the multiple templates (sometimes referred to herein as "balanced amplification" or "unbias amplification"). The generation of templates in separate reactions is illustrated in FIGS. 4B-4C. There a sample containing IgH (400) is divided into three portions (472,474, and 476) which are added to separate PCRs using J region primers (401) and V region primers (404, 406, and 408, respectively) to produce amplicons (420, 422 and 424, respectively). The latter amplicons are then combined (478) in secondary PCR (480) using P5 and P7 primers to prepare the templates (482) for bridge PCR and sequencing on an Illumina GA sequencer, or like instrument.

Sequence reads of the invention may have a wide variety of lengths, depending in part on the sequencing technique being employed. For example, for some techniques, several, trade-offs may arise in its implementation, for example, (i) the number and lengths of sequence reads per template and (ii) the cost and duration, of a sequencing operation. In one embodiment, sequence reads are in the range of from 20 to 400 nucleotides; in another embodiment, sequence reads are in a range of from 30 to 200 nucleotides; in still another embodiment, sequence reads are in the range of from 30 to 120 nucleotides. In one embodiment, 1 to 4 sequence reads are generated for determining the sequence of each clonotype; in another embodiment, 2 to 4 sequence reads are generated for determining the sequence of each clonotype; and in another embodiment, 2 to 3 sequence reads are generated for determining the sequence of each clonotype. In the foregoing embodiments, the numbers given are exclusive of sequence reads used to identify samples from different individuals. The lengths of the various sequence reads used in the embodiments described below may also vary based on the information that is sought to be captured by the read; for example, the starting location and length of a sequence read may be designed to provide the length of an NDN region as well as its nucleotide sequence; thus, sequence reads spanning the entire NDN region are selected. In other aspects, one or more sequence reads that in combination (but not separately) encompass a D and/or NDN region are sufficient.

In another aspect of the invention, sequences of clonotypes are determined in part by aligning sequence reads to one or more V region reference sequences and one or more J region reference sequences, and in part by base determination without, alignment to reference sequences, such as in the highly variable NDN region. A variety of alignment algorithms may be applied to the sequence reads and reference sequences. For example, guidance for selecting alignment methods is available in Batzoglou, Briefings in Bioinformatics, 6: 6-22 (2005), which is incorporated by reference. In one aspect, whenever V reads or C reads (as mentioned above) are aligned to V and J region reference sequences, a tree search algorithm is employed, e.g. as described generally in Gusfield (cited above) and Cormen et al, Introduction to Algorithms, Third Edition (The MIT Press, 2009).

Figure 4D:
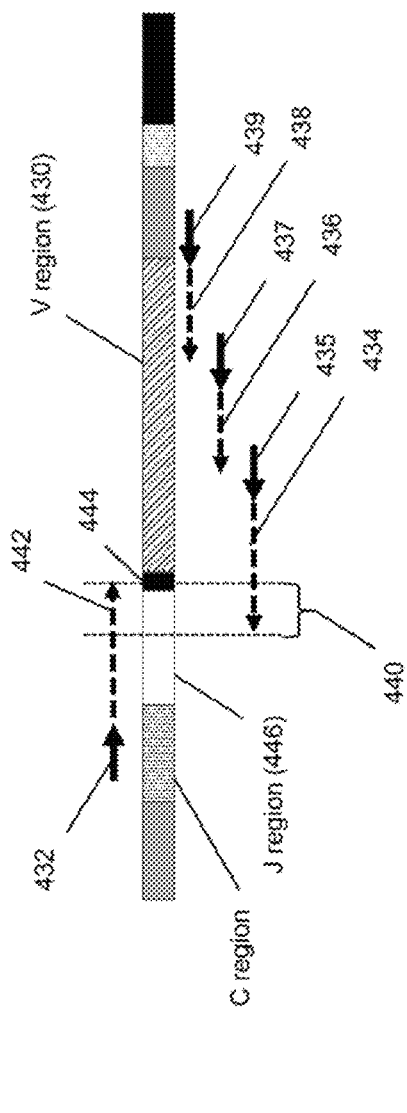
FIG. 4D illustrates the locations of sequence reads generated for an IgH chain.

The construction of IgH clonotypes from sequence reads is characterized by at least two factors: i) the presence of somatic mutations which makes alignment more difficult, and ii) the NDN region is larger so that it is often not possible to map a portion of the V segment to the C read. In one aspect of the invention, this problem is overcome by using a plurality of primer sets for generating V reads, which are located at different locations along the V region, preferably so that the primer binding sites are nonoverlapping and spaced apart, and with at least one primer binding site adjacent to the NDN region, e.g. in one embodiment from 5 to 50 bases from the V-NDN junction, or in another embodiment from 10 to 50 bases from the V-NDN junction. The redundancy of a plurality of primer sets minimizes the risk of tailing to detect a clonotype due to a failure of one or two primers having binding sites affected by somatic mutations. In addition, the presence of at least one primer binding site adjacent to the NDN region makes it more likely that a V read will overlap with the C read and hence effectively extend the length of the C read. This allows for the generation of a continuous sequence that spans all sizes of NDN regions and that can also map substantially the entire V and J regions on both sides of the NDN region. Embodiments for carrying out such a scheme are illustrated in FIGS. 4A and 4D, In FIG. 4A, a sample comprising IgH chains (400) are sequenced by generating a plurality amplicons for each chain by amplifying the chains with a single set of J region primers (401) and a plurality (three shown) of sets of V region (402) primers (404, 406, 408) to produce a plurality of nested amplicons (e.g., 410, 412, 416) all comprising the same NDN region and having different lengths encompassing successively larger portions (411, 413, 415) of V region (402). Members of a nested set may be grouped together after sequencing by noting the identify (or substantial identity) of their respective NDN, J and/or C regions, thereby allowing reconstruction of a longer V(D)J segment than would be the case otherwise for a sequencing platform with limited read length and/or sequence quality. In one embodiment, the plurality of primer sets may be a number in the range of from 2 to 5. In another embodiment the plurality is 2-3; and still another embodiment the plurality is 3. The concentrations and positions of the primers in a plurality may vary widely. Concentrations of the V region primers may or may not be the same. In one embodiment, the primer closest to the NDN region has a higher concentration than the other primers of the plurality, e.g. to insure that amplicons containing the NDN region are represented in the resulting amplicon. In a particular embodiment where a plurality of three primers is employed, a concentration ratio of 60:20:20 is used. One or more printers (e.g. 435 and 437 in FIG. 4D) adjacent to the NDN region (444) may be used to generate one or more sequence reads (e.g. 434 and 436) that overlap the sequence read (442) generated by J region primer (432), thereby improving the qualify of base calls in overlap region (440). Sequence reads from the plurality of primers may or may not overlap the adjacent downstream primer binding site and/or adjacent downstream sequence read. In one embodiment, sequence reads proximal to the NDN region (e.g. 436 and 438) may be used to identify the particular V region associated with the clonotype. Such a plurality of primers reduces the likelihood of incomplete or failed amplification in case one of the punier binding sites is hypermutated during immunoglobulin development. It also increases the likelihood that diversity introduced by hypermutation of the V region will be capture in a clonotype sequence. A secondary PCR may be performed to prepare the nested amplicons for sequencing, e.g. by amplifying with the P5 (401) and P7 (404, 406, 408) primers as illustrated to produce amplicons (420, 422, and 424), which may be distributed as single molecules on a solid surface, where they are further amplified by bridge PCR, or like technique.

Figure 4E:
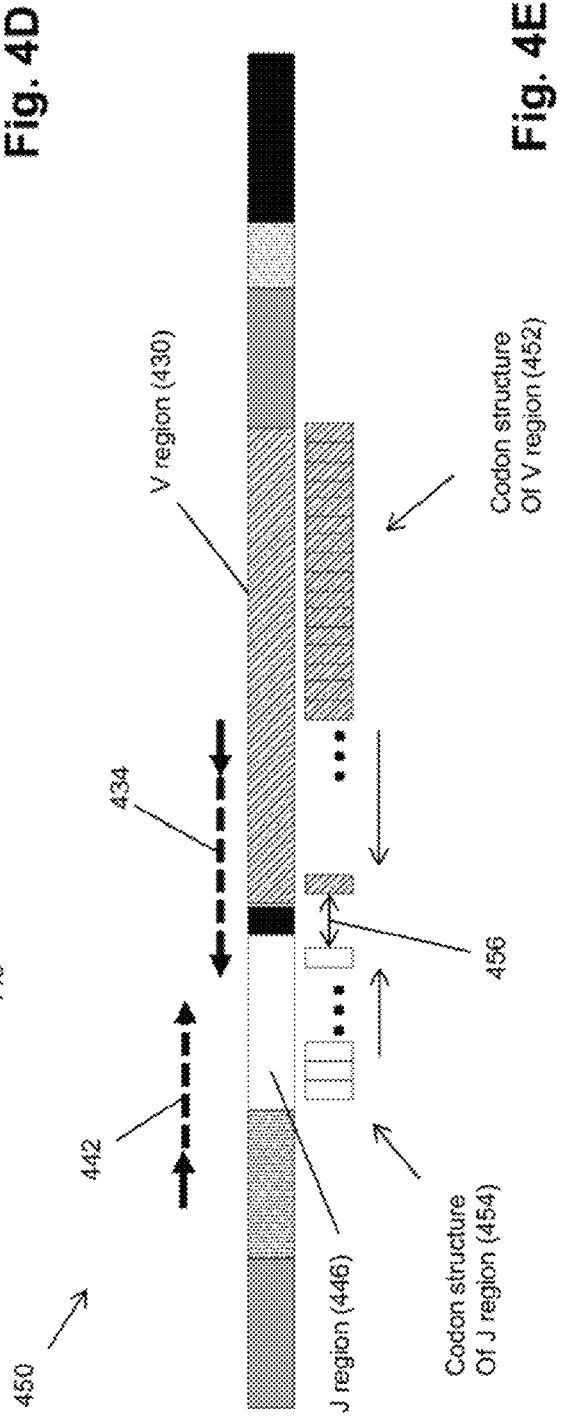
FIG. 4E illustrates the use of the codon structure of V and J regions to improve base calls in the NDN region.

Base calling in NDN regions (particularly of IgH chains) can be improved by using the codon structure of the flanking J and V regions, as illustrated in FIG. 4E. (As used herein, "codon structure" means the codons of the natural reading frame of segments of TCR or BCR transcripts or genes outside of the NDN regions, e.g. the V region, J region, or the like.) There amplicon (450), which is an enlarged view of the amplicon of FIG. 4B, is shown along with the relative positions of C read (442) and adjacent V read (434) above and the codon structures (452 and 454) of V region (430) and J region (446), respectively, below, in accordance with this aspect of the invention, after the codon structures (452 and 454) are identified by conventional alignment to the V and J reference sequences, bases in NDN region (456) are called (or identified) one base at a time moving from J region (446) toward V region (430) and in the opposite direction from V region (430) toward J region (446) using sequence reads (434) and (442). Under normal biological conditions, only the recombined TCR or IgH sequences that have in frame codons from the V region through, the NDN region and to fire J region are expressed as proteins. That is, of the variants generated somatically only ones expressed are those whose J region and V region codon frames are in-frame with one another and remain in-frame through the NDN region. (Here the correct frames of the V and J regions are determined from reference sequences). If an out-of-frame sequence is Identified based one or more low quality base calls, the corresponding clonotype is flagged for re-evaluation or as a potential disease-related anomaly. If the sequence identified is in-frame and based on high quality base calls, then there is greater confidence that the corresponding clonotype has been correctly called. Accordingly, in one aspect, the invention includes a method of determining V(D)J-based clonotypes from bidirectional, sequence reads comprising the steps of: (a) generating at least one J region sequence read that begins in a J region and extends into an NDN region and at least one V region sequence read that begins in the V regions and extends toward the NDN region such that the J region sequence read and the V region sequence read are overlapping in an overlap region, and the J region and the V region each have a codon structure; (b) determining whether the codon structure of the J region extended into the NDN region is in frame with the codon structure of the V region extended toward the NDN region. In a further embodiment, the step of generating includes generating at least one V region sequence read that begins in the V region and extends through the NDN region to the J region, such that the J region sequence read and the V region sequence read are overlapping in an overlap region.

Somatic Hypermutations. In one embodiment, IgH-based clonotypes that have undergone somatic hypermutation are determined as follows. A somatic mutation is defined as a sequenced base that is different from the corresponding base of a reference sequence (of the relevant segment, usually V, J or C) and that is present in a statistically significant number of reads. In one embodiment, C reads may be used to find somatic mutations with respect to the mapped J segment and likewise V reads for the V segment. Only pieces of the C and V reads are used that are either directly mapped to J or V segments or that are inside the clonotype extension up to the NDN boundary. In this way, the NDN region is avoided and the same 'sequence information' is not used for mutation finding that was previously used for clonotype determination (to avoid erroneously classifying as mutations nucleotides that are really just different recombined NDN regions). For each segment type, the mapped segment (major allele) is used as a scaffold and all reads are considered which have mapped to this allele during the read mapping phase. Each position of the reference sequences where at least one read has mapped is analyzed for somatic mutations. In one embodiment, the criteria for accepting a non-reference base as a valid mutation include the following: 1) at least N reads with the given mutation base, 2) at least a given fraction N/M reads (where M is the total number of mapped reads at this base position) and 3) a statistical cut based on the binomial distribution, the average Q score of the N reads at the mutation base as well as the number (M−N) of reads with a non-mutation base. Preferably, the above parameters are selected so that the false discovery rate of mutations per clonotype is less than 1 in 1000, and more preferably, less than 1 in 10000.

Phylogenic Clonotypes (Clans). In cancers, such as lymphoid neoplasms, a single lymphocyte progenitor may give rise to many related lymphocyte progeny, each possessing and/or expressing a slightly different TCR or BCR, and therefore a different clonotype, due to cancer-related somatic mutation(s), such as base substitutions, aberrant rearrangements, or the like. Cells producing such clonotypes are referred to herein as phylogenic clones, and a set of such related clones are referred to herein as a "clan." Likewise, clonotypes of phylogenic clones are referred to as phylogenic clonotypes and a set of phylogenic clonotypes may be referred to as a clan of clonotypes. In one aspect, methods of the invention comprise monitoring the frequency of a clan of clonotypes (i.e., the sum of frequencies of the constituent phylogenic clonotypes of the clan), rather than a frequency of an individual clonotype. Phylogenic clonotypes may be identified by one or more measures of relatedness to a parent clonotype. In one embodiment, phylogenic clonotypes may be grouped into the same clan by percent homology, as described more fully below. In another embodiment, phylogenic clonotypes are identified by common usage of V regions, J regions, and/or NDN regions. For example, a clan may be defined by clonotypes having common J and ND regions but different V regions; or it may be defined by clonotypes having the same V and J regions (including identical base substitutions mutations) but with different NDN regions: or it may be defined by a clonotype that has undergone one or more insertions and/or deletions of from 1-10 bases, or from 1-5 bases, or from 1-3 bases, to generate clan members. In another embodiment, members of a clan are determined as follows. Clonotypes are assigned to the same clan if they satisfy the following criteria: i) they are snapped to the same V and J reference segments, with the mappings occurring at the same relative positions in the clonotype sequence, and ii) their NDN regions are substantially identical. "Substantial" in reference to clan membership means that some small differences in the NDN region are allowed because somatic mutations may have occurred in this region. Preferably, in one embodiment, to avoid falsely calling a mutation in the NDN region, whether a base substitution is accepted as a cancer-related mutation depends directly on the size of the NDN region of the clan, for example, a method may accept a clonotype as a clan member if it has a one-base difference from clan NDN sequence(s) as a cancer-related mutation if the length of the clan NDN sequence(s) is in nucleotides or greater, e.g. 9 nucleotides or greater, otherwise it is not accepted, or if it has a two-base difference from clan NDN sequence) as cancer-related mutations if the length of the clan NDN sequencers) is n nucleotides or greater, e.g. 20 nucleotides or greater, otherwise it is not accepted. In another embodiment, members of a clan are determined using the following criteria: (a) V read maps to the same V region, (b) C read maps to the same J region, (c) NDN region substantially identical (as described above), and (d) position of NDN region between V-NDN boundary and J-NDN boundary is the same (or equivalently, the number of downstream base additions to D and the number of upstream base additions to D are the same). Clonotypes of a single sample may be grouped into clans and clans from successive samples acquired at different times may be compared wish one another. In particular, in one aspect of the invention, clans containing clonotypes correlated wish a disease, such as a lymphoid neoplasm, are identified from clonotypes of each sample and compared with that of the immediately previous sample to determine disease status, such as, continued remission, incipient relapse, evidence of further clonal evolution, or the like.

It is expected that PCR error is concentrated in some bases that were mutated in the early cycles of PCR. Sequencing error is expected to be distributed in many bases even though it is totally random as She error is likely to have some systematic biases. It is assumed that some bases will have sequencing error at a higher rate, say 5% (5 fold the average). Given these assumptions, sequencing error becomes the dominant type of error. Distinguishing PCR errors from the occurrence of highly related clonotypes will play a role in analysis. Given the biological significance to determining that there are two or more highly related clonotypes, a conservative approach to making such calls is taken. The detection of enough of the minor clonotypes so as to be sure with high confidence (say 99.9%) that there are more than one clonotype is considered. For example of clonotypes that are present at 100 copies/1,000,000, the minor variant is detected 14 or more times for it to be designated as an independent clonotype. Similarly, for clonotypes present at 1,000 copies/ 1,000,000 the minor variant can be detected 74 or more times to be designated as an independent clonotype. This algorithm can be enhanced by using the base quality score that is obtained, with each sequenced base. If the relationship between quality score and error rate is validated above, then instead of employing the conservative 5% error rate for all bases, the quality score can be used to decide she number of reads that need to be present to call an independent clonotype. The median, quality score of the specific base in all the reads can be used, or more rigorously, the likelihood of being an error can be computed given the quality score of the specific base in each read, and then the probabilities can be combined (assuming independence) to estimate the likely number of sequencing error for that base. As a result, there are different thresholds of rejecting the sequencing error hypothesis for different bases with different quality scores. For example for a clonotype present at 1,000 copies/1,000,000 the minor variant is designated independent when it is detected 22 and 74 times if the probability of error were 0.01 and 0.05, respectively.

In the presence of sequencing errors, each genuine clonotype is surrounded by a 'cloud' of reads with varying numbers of errors with respect to the its sequence. The "cloud" of sequencing errors drops off in density as the distance increases from the clonotype in sequence space. A variety of algorithms are available for converting sequence reads into clonotypes. In one aspect, coalescing of sequence reads (that is, merging candidate clonotypes determined to have one or more sequencing errors) depends on at least three factors: the number of sequences obtained for each of the clonotypes being compared; the number of bases at which they differ; and the sequencing quality score at the positions at which they are discordant. A likelihood ratio may be constructed and assessed that is based on the expected error rates and binomial distribution of errors. For example, two clonotypes, one with 150 reads and the other with 2 reads with one difference between them in an area of poor sequencing quality will likely be coalesced as they are likely to be generated by sequencing error. On the other hand two clonotypes, one with 100 reads and the other with 50 reads with two differences between them are not coalesced as they are considered to be unlikely to be generated by sequencing error. In one embodiment of the invention, the algorithm described below may be used for determining clonotypes from sequence reads. In one aspect of the invention, sequence reads are first converted into candidate clonotypes. Such a conversion depends on the sequencing platform employed. For platforms that generate high Q score long sequence reads, the sequence read or a portion thereof may be taken directly as a candidate clonotype. For platforms that generate lower Q score shorter sequence reads, some alignment and assembly steps may be required for converting a set of related sequence reads into a candidate clonotype. For example, for Solexa-based platforms, in some embodiments, candidate clonotypes are generated, front collections of paired reads from, multiple clusters, e.g. 10 or more, as mentioned above.

The cloud of sequence reads surrounding each candidate clonotype can be modeled using the binomial distribution and a simple model for the probability of a single base error. This latter error model can be inferred from mapping V and J segments or from the clonotype finding algorithm itself, via self-consistency and convergence. A model is constructed for the probability of a given 'cloud' sequence Y with read count C2 and E errors (with respect to sequence X) being part of a true clonotype sequence X with perfect read count C1 under the null model that X is the only true clonotype in this region of sequence space. A decision is made whether or not to coalesce sequence Y into the clonotype X according the parameters C1, C2, and E. For any given C1 and E a max value C2 is pre-calculated for deciding to coalesce the sequence Y. The max values for C2 are chosen so that the probability of failing to coalesce Y under the null hypothesis that Y is part of clonotype X is less than some value P after integrating over all possible sequences Y with error E in the neighborhood of sequence X. The value P is controls the behavior of the algorithm and makes the coalescing more or less permissive.

If a sequence Y is not coalesced into clonotype X because its read count is above me threshold C2 for coalescing into clonotype X then it becomes a candidate for seeding separate clonotypes. An algorithm implementing such principles makes sure that any other sequences Y2, Y3, etc. which are 'nearer' to this sequence Y (that had been deemed independent of X) are not aggregated into X. This concept of 'nearness' includes both error counts with respect to Y and X and the absolute read count of X and Y, i.e. it is modeled in the same fashion as the above model for the cloud of error sequences around clonotype X. In this way 'cloud' sequences can be properly attributed to their correct clonotype if they happen to be 'near' more than one clonotype.

In one embodiment, an algorithm proceeds in a top down fashion by starting with the sequence X with the highest read count. This sequence seeds the first clonotype. Neighboring sequences are either coalesced into this clonotype if their counts are below the precalculated thresholds (see above), or left alone if they are above the threshold or 'closer' to another sequence that was not coalesced. After searching all neighboring sequences within a maximum error count, the process of coalescing reads into clonotype X is finished. Its reads and ail reads that have been coalesced into it are accounted for and removed from the list of reads available for making other clonotypes. The next sequence is then moved on to with the highest read count. Neighboring reads are coalesced into this clonotype as above and this process is continued until there are no more sequences with read counts above a given threshold, e.g. until all sequences with more than 1 count have been used as seeds for clonotypes.

As mentioned above, in another embodiment of the above algorithm, a further test may be added for determining whether to coalesce a candidate sequence Y into an existing clonotype X, which takes into account quality score of the relevant sequence reads. The average quality score(s) are determined for sequences) Y (averaged across ail reads with sequence Y) were sequences Y and X differ. If the average score is above a predetermined value then it is more likely that the difference indicates a truly different clonotype that should not be coalesced and if the average score is below such predetermined value then it is more likely that sequence Y is caused by sequencing errors and therefore should be coalesced into X.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

EXAMPLE 1

Naïve Bayesian Classifier of Evolution in ALL

In this example, construction of a naïve Bayesian classifier model of $V_B$ substitution is outlined. "IMGT" refers to immunology databases maintained by the international ImMunoGeneTics information system (http://www/imgt.org), described in Robinson et al, Nucleic Acids Research (1 Jan. 2013) 41(D1): D1222-D1227. The model below may be implemented in various computer programming languages., including but not limited to, C++, Ruby, Java, Python, or the like.

Elements of IgH V(D)J generation used in model:
Different pieces of data about each test clones:
    J allele & J deletion
    NDN sequence
    V allele & V deletion
Additional information from IMGT about disease clones:
    D allele
    position of D region
    D deletions (J & V side)
Bayes' Theorem combines the following quantities:

$$P(\text{evolution}|\text{data}) = \frac{P(\text{data}|\text{evolution})P(\text{evolution})}{P(\text{data})}$$

If data can be described as $d_1, d_2, \ldots, d_n$ and we assume independence between components, than we have:

$$P(\text{data}) = P(d_1, d_2, \ldots, d_m) = P(d_1)P(d_2) \ldots P(d_n) = \pi_{i=1}^n P(d_i)$$

Probabilities needed for the naive Bayes classifier:
P(evolution|data): posterior probability, our goal.
P(evolution): prior probability, set to 0.0001, but could be improved
P(data|evolution): conditional probability
P(data): evidence, equal to
P(data|evolution)+P(data|noEvolution)
    So for every element, we need P(data|evolution) and P(data|noEvolution)
Data elements used:
NDN decomposed as $N_1DN_2$
    Matching J allele & J deletion.
    Matching $N_1$ bases, if any.
    Matching D bases, D allele & J-side D-deletion, if any.
    Matching $N_2$ bases, if any.
Matching J allele and J deletions:
P(Jallele, Jdeletion|evolution)=1
    V-replacement model of evolution requires that the J allele & deletion matches.
P(Jallele, Jdeletion|noEvolution)=P(Jallele|normal)P(Jdeletion|normal)
    Based on 116 k normal BM clones from 4 samples annotated through IMGT.
    J allele & J deletion not dependent on each other.

Matching N bases ($N_1$ and $N_2$):
Count how many sequential bases are matched (out of $m_n$ bases total)

$$P(N_1 | \text{evolution}) = \frac{1}{(m_{n1} + 1)}$$

We can match $0, 1, \ldots, m_{n1}$ bases $1/(m_{n1}+1)$ represents a non-informative prior: all possibilities are equally likely.

This is incorrect for $N_1$ (generally match everything) but this is reasonable for $N_2$.

$P(N_1 | \text{noEvolution}) = 0.25^{n1} * 0.75$

Geometric distribution: each base has 25% of occurring.

Matching D regions:

Dmatch: D allele & J-side D deletion match

P(Dmatch|evolution)=high high is set arbitrarily to 0.95

P(Dmatch|noEvoltion)=P(Dallele|normal)P(DdeletionJ|normal)

D regions are not matched directly; the number of matching bases is known (out of $m_d$).

P(D|evolution)=P(D|Dmatch)P(Dmatch|evolution)+P(D|DnotMatch)P(DnotMatch|evolution)

P(D|Dmatch)=$1/(m_d+1)$

P(D|DnotMatcb)=$0.25^d * 0.75$

V-side deletions are ignored in the model.

Results from data of Example 2: 492 evolved clonotypes identified:

|  | badQuality | evol | fewMol | noEvol | uncertainV |
|---|---|---|---|---|---|
| badQuality | 132 | 0 | 0 | 0 | 0 |
| fewMol | 0 | 0 | 5232 | 0 | 0 |
| uncertainV | 0 | 0 | 0 | 0 | 25253 |
| unrelated | 0 | 0 | 0 | 46856 | 0 |
| unrelatedButD | 0 | 492 | 0 | 38 | 0 |

EXAMPLE 2

Evolution of the Heavy Chain Locus in Children with B Precursor ALL

In this example, clonal evolution in ALL was determined by performing IgH repertoire sequencing on diagnostic samples from 51 children with pre-B ALL. Using this approach, high frequency leukemic "index" clonotypes, or correlating clonotypes, were identified and distinct but related "evolved" clonotypes were found in most of the pre-B ALL patients.

Clinical samples. 51 diagnostic bone marrow samples from children with acute lymphoblastic leukemia diagnosed at Lucile Packard Children's Hospital were collected, on a protocol approved by the Stanford Institution Review Board as described in Salzman et al, PLoS One 7, e30733 (2012). Informed consent was obtained prior to specimen collection and samples were de-identified prior to use in studies. Peripheral blood mononuclear cells were obtained front 35 patients with chronic lymphocytic leukemia diagnosed at Stanford University Medical Center. All CLL patient samples were obtained with explicit authorization and monitoring by the Stanford University School of Medicine Institutional Review Board. Patient and sample characteristics are summarized in Table 1. The patients were a random sampling of children diagnosed with ALL at Lucile Packard Children's Hospital over the previous 7 years. Data were collected on prognostic variables currently used for disease stratification, such as age, initial white blood cell count, cytogenetics, central nervous system (CNS) stage, and end of induction minimal residual disease. Samples that had less than 500 starting cells as measured by flow cytometry (6 normal B-cell sorts) were not analyzed further. One patient had only 1 malignant cell sort (patient 13).

Sequencing the IgH locus in pre-B ALL diagnostic bone marrow samples. Clonal evolution in pre-B ALL bone marrow samples at diagnosis was characterized by amplification and sequencing of IgH loci. DNA from bone marrow mononuclear cells (BMMC) (which were isolated from each of the 51 patients at diagnosis and cryopreserved) was isolated, and IgH encoding DNA was amplified, sequenced and analyzed to identify index clones and clones evolved therefrom using the "6-base" clonal evolution algorithm described above.

IgH amplification and sequencing. The procedure disclosed by Faham and Willis (cited above) was followed. Genomic DNA was amplified using locus specific primer sets for IgH. The goal of this amplification reaction was to reproducibly amplify all possible rearranged IgH sequences in a sample while appending the necessary sequences for cluster formation and sample indexing. Briefly, steps of the Faham and Willis procedure were applied as follows: DNA was isolated using AllPrep DNA mini and/or micro kits, according to manufacturer's instructions (Qiagen). First stage primers were designed so as to allow for the amplification of all known alleles of the germline IgH sequences. To minimize the risk of not amplifying a specific clonotype sequence because of a somatic hypermutation at the primer hybridization site, three sets of printers were designed in the $V_H$ segments. Therefore each $V_H$ segment is amplified by 3 primers ameliorating the problem of somatic hypermutations interfering with amplification. Primers were optimized such that each possible $V_H$ and $J_H$ segment was amplified at a similar rate so as to minimally skew the repertoire frequency distribution during the amplification process. Specificity of the printers was, in contrast, not optimized as the primer sequences could be mapped and removed from the eventual sequence read. Thus a given sequence may have been amplified by multiple primers. This methodology led to slightly different primer designs than have been published previously for similar IgH amplification approaches, e.g. van Dongen et al, Leukemia (cited above). The numbers of primers and the positions of these primers are shown in Faham and Willis, U.S. patent publication 2011/0207134. At the 5' ends of $V_H$ segment primers a universal sequence was appended. These sequences are complementary to a set of second stage PCR primers. Similarly fee primers on the $J_H$ side had a 5' tail with a universal sequence that is complementary to second stage PCR primers. The second stage PCR primers contained the sequence primer and the P5 sequence used for cluster formation in the Illumina Genome Analyzer sequencer. The primers on the $V_H$ side of the amplification constituted one of a set of primers, each of which had a 3' region that annealed to the overhang sequence appended in the first reaction but which further contained one of multiple 6 base pair indices that allowed for sample multiplexing on the sequencer. Each of these primers further contained a 5' tail with the P7 sequence used for cluster formation so. the Illumina Genome Analyzer sequencer. First stage PCR was carried out using a high fidelity polymerase (AccuPrime, Life Technologies) for 16 cycles. 1/100 of this amplification reaction was then used as the template for a second PCR reaction using the second stage primers including the primer containing a sample index that was unique to a particular sample. A second stage PCR was carried out for 22 cycles. Different samples were pooled to be sequenced in the same sequencing Illumina Genome Analyzer sequencing lane. The pool was then purified using the QIAquick PCR purification kit (Qiagen). Cluster formation and sequencing was carried out per the manufacturer protocol (Illumina, Inc., La Jolla, Calif.). Specifically, three sequencing reactions were performed. First 115 bp were sequenced from the $J_H$ side sufficient to sequence through the junctional sequence from $J_H$ to $V_B$. At this point, the synthesized strand was denatured and washed off. A second sequencing primer was annealed that allowed the sample index to be sequenced for 6 cycles to identify the sample. At this point the reverse complement strand was generated per the Illumina protocol. A final sequencing read of 95 bp was obtained from the $V_H$-to-$J_H$ direction providing ample sequence to map the $V_H$ segment accurately.

Clonotype determination. After exclusion of low quality reads, sequence data were then analyzed to determine the clonotype sequences including mapping to germline $V_H$ and $J_H$ consensus sequences. First, the sample index sequences were used to identify which of the sequences originate from which of the pooled samples. Sequences whose index were not a perfect match to one of the indices used in a specific run were excluded. Next the forward read was used to map the $J_H$ segment. Since all the sequences started from the same position of the $J_H$ segments, all the $J_H$ segments started at a predefined sequencing position. The first 25 bp of the $J_H$ segments were used to map the $J_H$ segment. Any read with more than 5 high quality mismatches to the known $J_H$ segments was excluded from further analysis. After $J_H$ segment identification, $V_H$ segments were mapped. The reverse read was used for this purpose. First, the $V_H$ primer was mapped and excluded. Thereafter, the next 70 bases of the reverse read were mapped to the known $V_H$ segments. Reads that did not map to $J_H$ and $V_H$ segments were excluded. The next step in mapping involved identifying the frame that related the forward and reverse reads and this allowed a continuous sequence from $J_H$ to $V_H$ to be constructed. This was done rising the last 15 bases of the forward read which were reliably within the $V_H$ segment regardless of NDN length. While these bases could be of relatively lower sequence quality as they were at the terminal end of a long read, they could be used to map within a single identified $V_H$ segment in order to identify the position at which the two reads could be joined. Finally, the known $V_H$ and $J_H$ sequences to which the reads map were used to identify the point in the forward read at which the sequences at the junctions diverged from these mapped segments. To generate a clonotype, as least two identical sequences needed to be identified. Given sequencing and PCR errors, many different but highly related clonotypes might originate from one clonotype. Therefore coalescence of highly related clonotypes was allowed. For example two sequences with one base difference but present at vastly different frequencies were consistent with sequencing or PCR error. On the other hand two sequences with two base differences and present at similar magnitudes were not likely to arise from sequencing error. The number of molecules associated with each clonotype was estimated based the frequency of spikes added in known quantities. Clonotypes with less than one molecule were discarded. The frequency of all the clonotypes in each sample was determined by calculating the number of sequencing reads for each clonotype and dividing by the total number of passed sequencing reads in the sample. Individual clonotypes with at least at 5% frequency were designated index clonotypes.

Leukemic index clonotypes identified in ALL diagnostic samples. A frequency threshold of 5% was set to designate a clonotype as an "index" leukemic clone; that is, a clonotype correlated with, the leukemia. Using this threshold, 86 leukemic index clonotypes were identified in the diagnostic bone marrow samples (Table 2). 16 patients had one index clonotype, 16 patients had 2 index clonotypes and 11 had greater than two index clonotypes (Table 2). For patients with one or more index clonotypes, a significant majority of the IgH reads were generated by the index clonotypes (mean 87%) (Table 2).

Figure 1B:
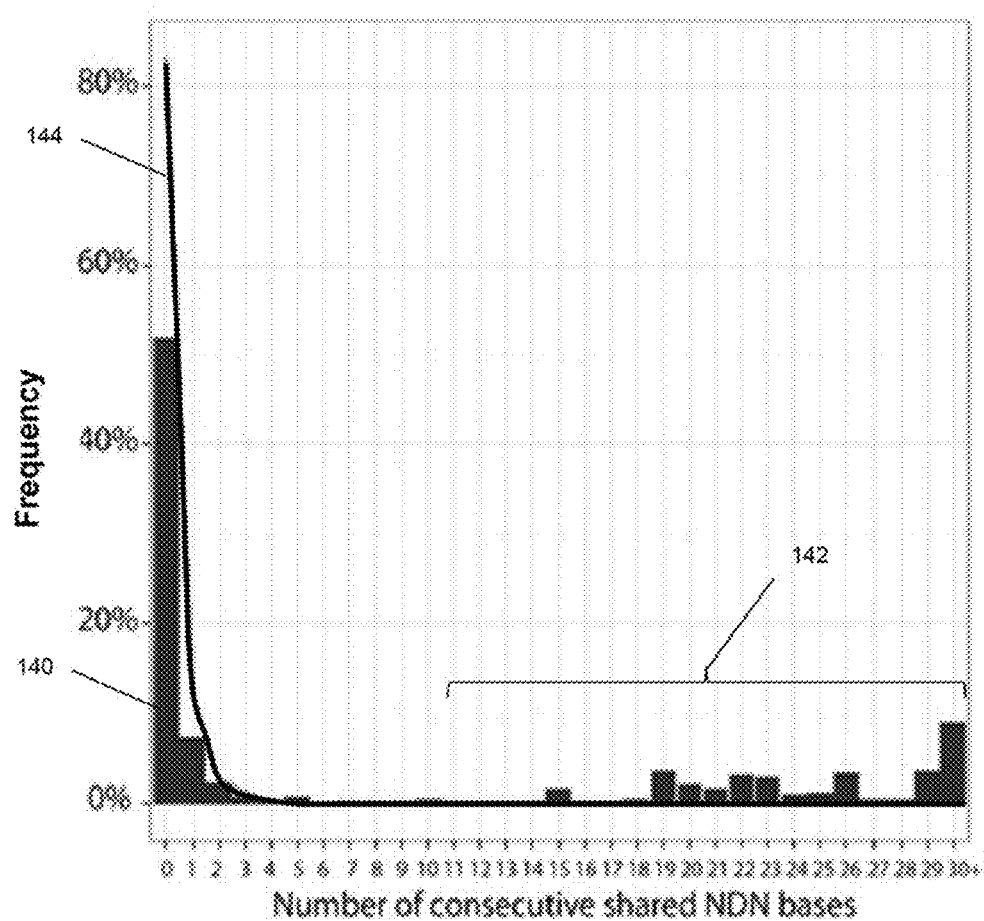
FIG. 1B shows percentages of clonotypes that share $J_H$ and NDN bases wish index clones. The x-axis represents the number of shared bases. Data from ALL samples are shown as the black histogram (140), showing a sharp decline in shared based from 0 to 5, that can be explained by the matching random bases (as would be expected from unrelated sequences). There is an increase in frequency after 10 bases (142), which reflects a high rate of clonal evolution. For comparison, the line (144) indicates base sharing in CLL samples and lacks the increase in sharing after 10 bases.
Figure 1C:
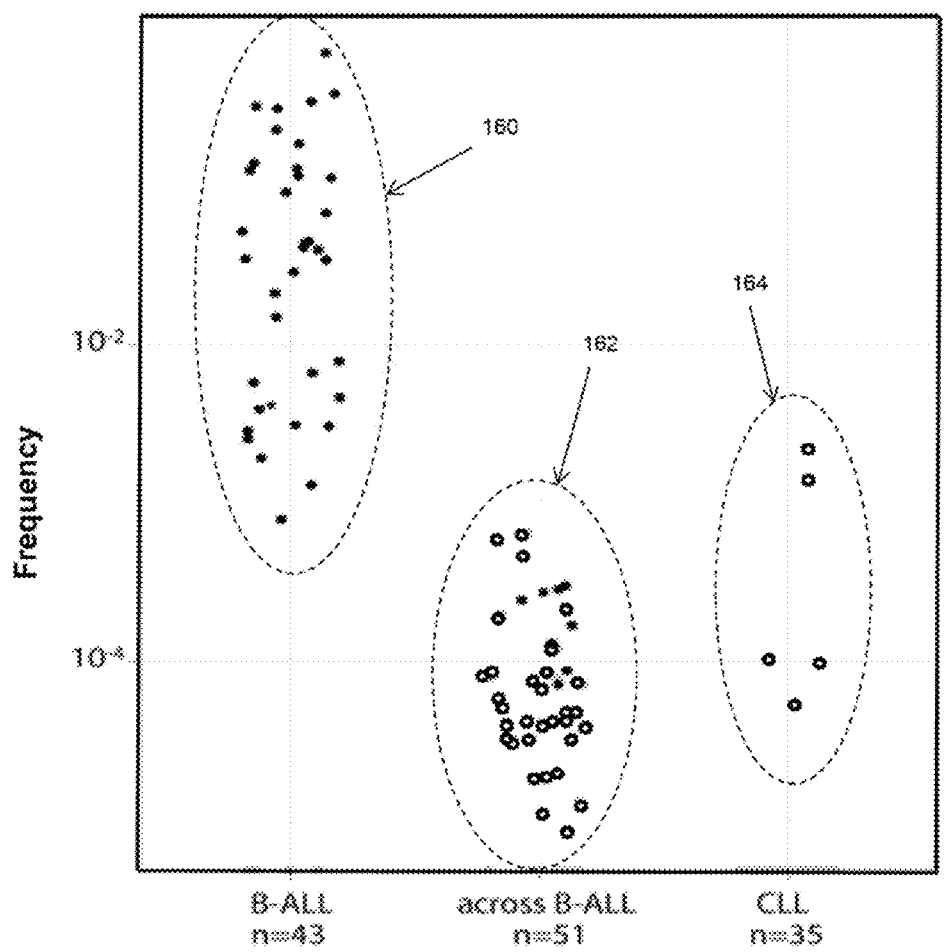
FIG. 1C shows per patient frequency of evolved clones in ALL (160), CLL (162) and in patient-permuted ALL (164) samples (across ALL). Each solid dot or open circle represents a patient, with a solid dot representing a frequency with statistically significant value and an open circle representing a frequency without a statistically significant value.

Extent of NDN sharing required for identification of evolved clonotypes. Visual comparison of index and non-index clonotype sequences within individual patients revealed that many clonotypes shared the same JH segments and a portion of the NDN region adjacent to the JH segment, but differed in their VH segment and the NDN region immediately adjacent to the VH segment. FIG. 1A schematically illustrates how clonotype coding segments (100) of an index clone (106) relate to several evolved clonotypes in patient 23. Index clonotype (106) and evolved clonotypes (clone 1 (101), clone 2 (102), clone 3 (103), clone 4 (104) and clone 5 (105)) share nucleotides (shown in capital letters) of JH (110) and a large portion of the $N_1DN_2$ regions (112, 114 and 116, respectively) but differ in their VH segments (118) (only partially shown as lower case letters). Within each ALL sample, index clones sharing the same JH segment were compared to other clones in its clonotype profile and analyzed with respect to the number of consecutive NDN bases shared in the JH-to-VH direction (as exemplified by the clonotypes shown in FIG. 1A). In addition to the expected exponential decline in sharing of sequential NDN nucleotides, there were a large number of clones that shared over 15 bases (FIG. 1B). Based on these observations, the "6-base" algorithm described above was developed to identify evolved clones based on shared NDN bases. Because D segment lengths vary, yet bases in each D segment are not independent of each other (i.e. they are not random sequence regions), identical D segments are represented as two effective NDN bases. This modification maintained separation, between the level of sharing observed in the ALL and CLL samples. Very few CLL clones (0.03%) with the same J segment as the index clone shared more than 6 effective NDN bases with the index clone, while 37% of ALL clones with the same J segment shared 6 or more effective NDN bases with an index clone, which suggests that a threshold of 6 shared effective NDN bases can be used to define evolved clonotypes (equivalent to $p<10^{-4}$ with a geometric distribution).

Evolution criteria. Potentially related clonotypes for further analysis were identified using three criteria: (1) Identical JH segment sequence to index clonotype, (2) greater than 1 molecule and (3) different VH allele from the index clonotype. The potentially related clonotypes were men analyzed for the extent of NDN sharing as described above. The NDN sequence was determined by identifying the location where the consensus sequence does not match the VH and JH segment sequences. In the case of index clones, the JunctionAnalysis tool from IMGT (38) was used to increase accuracy and identify which bases belong to the D segment. The location of the VH allele was obtained from the Ensembl database.

Evolved clonotypes identified in ALL diagnostic samples. With the 6-base algorithm., almost 14,000 evolved clonotypes were identified in the diagnostic ALL bone marrow samples (Table 2). The number of evolved clonotypes per ALL patient varied widely from 0 to 4,024 clonotypes, with 37 of 43 patients having evolved clonotypes (Table 2). Fortytwo percent of clonotypes with a frequency above 0.1% were comprised of clonotypes evolved from the ancestral ALL clone.

Validation of evolved clonotype selection criteria. When the clonal evolution selection criteria (using the 6-base algorithm) were applied, to the ALL patient samples, the vast majority of samples 37 of 43 patients. 86%) showed the presence of evolved clonotypes.

Variation in clonal evolution patterns at the patient level. The clonal evolution pattern in each patient was characterized. The percent of evolved clonotypes ranged dramatically from 0% to 86% across the ALL patients, with the majority of patients having evolved clonotypes (Table 2). The 43 ALL patients who had index clonotypes could be categorized into three distinct, bins based on the percent of clonal evolution present in their diagnostic sample. Specifically, 6 patients had no evolution (0%), 23 patients had some evolution (0-10%) and 14 patients had a high degree of evolution (>10%) (Table 2). This wide variation underscores the differences in clonal, evolution between patients, and may serve as the basis for further exploration of the prognostic significance of such clonal evolution in ALL.

Striking differences in number of evolved clonotypes between independent index clonotypes in the same patients. The distribution of evolved clonotypes within samples that contained multiple index clonotypes was assessed. Twenty-seven ALL patients had multiple index clonotypes in their diagnostic bone marrow samples (Table 2). The definition of index clones is based on a frequency threshold and therefore there were several cases where index clones were related to each other by evolution. Similarly, as part of normal B cell development and in pre-B ALL, IgH can rearrange in one or both chromosomes potentially leading to more than one independent index clonotype (i.e., not related to each other by evolution). Altogether, there were 15 samples with more than one independent index clone.

Low-frequency evolved clonotypes that were identified in this example would be undetectable by routine methods due to the limited sensitivity of flow cytometry-based MRD quantification. Moreover, evolved clonotypes at relapse would be undetectable by standard allele-specific PCR techniques because primers are designed for the specific detection of high-frequency index clonotypes. This example demonstrates that a sequencing-based approach, which enables quantitative analysis of clonal evolution in diagnostic and follow-up ALL samples, provides improved MRD monitoring.

TABLE 1

Summary of patient characteristics

| | | Number | Percent |
|---|---|---|---|
| Age (years) | 0-1 | 1 | 2 |
| | 1-10 | 38 | 75 |
| | ≥10 | 12 | 24 |
| Initial WBC Count | <50K | 38 | 75 |
| | >30K | 13 | 25 |
| NCI Risk Group | Standard Risk | 33 | 65 |
| | High Risk | 15 | 29 |
| | Very High Risk | 2 | 4 |
| | Infant Leukemia | 1 | 2 |
| Cytogenetics | TEL-AML | 15* | 29 |
| | Hyperdiploid w/o trisomy 4, 10, 17 | 10 | 20 |
| | Hyperdiploid w/trisomy 4, 10, 17 | 7* | 14 |
| | MLL-rearranged | 1 | 2 |
| | Philadelphia Chromomsome | 2 | 4 |
| | Other | 10 | 20 |
| | Normal | 6 | 12 |
| | Not Done | 1 | 2 |
| CNS Stage | 1 | 38 | 75 |
| | 2 | 12 | 24 |
| | 3 | 1 | 2 |
| End of Induction MRD | <0.1% | 36 | 71 |
| | >0.1% <1% | 4 | 8 |
| | >1% | 4 | 8 |
| | Not Done | 7 | 14 |
| Current Disease Status | Relapse | 4 | 8 |
| | Continuous Remission | 47 | 92 |

*sample 8 had both TEL-AML and Hyperdiploid w/trisomy 4, 10, 17

TABLE 2

Per patient summary of malignant clones in ALL samples and sample sorts

| Patient ID | Number of index clones | Total frequency of index clones (%) | Total # (and %) evolved clones | Total frequency of index clones in sort for normal B cells (%) | Total frequency of index clone in first sort for malignant B cells (%) | Total frequency of index clones in second sort for malignant B cells (%) |
|---|---|---|---|---|---|---|
| 1 | 0 | 0 | 0 (0.0%) | NA* | NA | NA |
| 2 | 0 | 0 | 0 (0.0%) | NA | NA | NA |
| 3 | 1 | 90.3 | 14 (0.3%) | 0.5 | 98.3 | 83.3 |
| 4 | 0 | 0 | 0 (0.0%) | NA | NA | NA |
| 5 | 3 | 95.7 | 668 (33.3%) | 3.3 | 99.2 | 94.8 |
| 6 | 5 | 80.8 | 883 (61.7%) | 0.7 | 98.5 | 84.4 |
| 7 | 1 | 88.7 | 25 (3.4%) | NA | NA | NA |
| 8 | 2 | 96 | 301 (62.2%) | NA | NA | NA |
| 9 | 2 | 98.1 | 42 (8.8%) | 7.3 | 98.8 | 98.8 |
| 10 | 3 | 99.3 | 18 (6.8%) | 0.4 | 99.8 | 99.3 |
| 11 | 0 | 0 | 0 (0.0%) | NA | NA | NA |
| 12 | 2 | 99.5 | 12 (60.0%) | NA | 99.6 | 99.3 |
| 13 | 0 | 0 | 0 (0.0%) | NA | NA | NA |
| 14 | 1 | 92.8 | 22 (0.3%) | 0.2 | 98.1 | 97.8 |
| 15 | 5 | 78.4 | 4024 (85.5%) | 14 | 79.8 | 78.8 |
| 16 | 2 | 98.4 | 4 (0.8%) | 6.7 | 99.3 | 99.3 |
| 17 | 3 | 98.8 | 13 (2.4%) | 0 | 99.1 | 98.7 |
| 18 | 3 | 72 | 368 (43.0%) | NA | NA | NA |
| 19 | 1 | 75.2 | 0 (0.0%) | NA | NA | NA |
| 20 | 3 | 89 | 460 (29.9%) | NA | NA | NA |

TABLE 2-continued

Per patient summary of malignant clones in ALL samples and sample sorts

| Patient ID | Number of index clones | Total frequency of index clones (%) | Total # (and %) evolved clones | Total frequency of index clones in sort for normal B cells (%) | Total frequency of index clone in first sort for malignant B cells (%) | Total frequency of index clones in second sort for malignant B cells (%) |
|---|---|---|---|---|---|---|
| 21 | 1 | 97.3 | 0 (0.0%) | 0.2 | 98.1 | 94.4 |
| 22 | 1 | 96.4 | 35 (18.1%) | 41.5 | 94.3 | 99 |
| 23 | 3 | 64.9 | 2645 (34.6%) | 0.03 | 68.3 | 42.5 |
| 24 | 0 | 0 | 0 (0.0%) | NA | NA | NA |
| 25 | 1 | 99.9 | 7 (12.7%) | 8.4 | 99.9 | 99.9 |
| 26 | 2 | 97.3 | 196 (8.1%) | 1.5 | 99.6 | 99.6 |
| 27 | 2 | 97.1 | 22 (1.3%) | 0 | 95.9 | 99.8 |
| 28 | 3 | 98.6 | 9 (4.9%) | NA | 98.5 | 98.4 |
| 29 | 3 | 71.6 | 17 (0.2%) | 0.5 | 81.2 | 76.6 |
| 30 | 1 | 93.1 | 18 (2.9%) | 5 | 96.3 | 90 |
| 31 | 2 | 76.9 | 4 (0.4%) | 0 | NA | 1 |
| 32 | 2 | 99 | 11 (1.4%) | 0.3 | 99.9 | 99.9 |
| 33 | 1 | 66.6 | 3 (0.3%) | 0.4 | 99.7 | 98.9 |
| 34 | 2 | 99.5 | 0 (0.0%) | 7.5 | 99.9 | 99.8 |
| 35 | 2 | 63.4 | 1149 (27.5%) | 1 | 67 | 63.6 |
| 36 | 1 | 22.4 | 0 (0.0%) | 0 | 95.6 | 98 |
| 37 | 0 | 0 | 0 (0.0%) | NA | NA | NA |
| 38 | 2 | 97 | 154 (13.4%) | 4.7 | 97.5 | 98.2 |
| 39 | 1 | 99 | 0 (0.0%) | NA | 99.8 | 99.3 |
| 40 | 1 | 84.9 | 24 (0.3%) | 1.8 | 89.4 | 89.7 |
| 41 | 0 | 0 | 0 (0.0%) | NA | NA | NA |
| 42 | 2 | 99.1 | 5 (4.2%) | 2.1 | 99.3 | 99.3 |
| 43 | 2 | 98.9 | 2 (8.7%) | NA | 98.6 | 98.2 |
| 44 | 2 | 99.1 | 3 (0.8%) | 1.4 | 99.9 | 99.9 |
| 45 | 2 | 79.9 | 5 (0.3%) | 0.6 | 79.1 | 2.7 |
| 46 | 1 | 94.6 | 0 (0.0%) | 2.1 | 97.8 | 97.5 |
| 47 | 1 | 98.5 | 60 (5.1%) | 1.5 | 99.7 | 99.8 |
| 48 | 4 | 99.8 | 30 (36.1%) | 3.2 | 99.8 | 99.9 |
| 49 | 1 | 99 | 4 (0.6%) | 0.7 | 99.7 | 99.2 |
| 50 | 2 | 81.5 | 2724 (41.7%) | 0.9 | 85.9 | 88.7 |
| 51 | 1 | 5.8 | 4 (0.5%) | 0 | 39.5 | 39.8 |

*NA indicates that a particular sort was not available for a patient.

DEFINITIONS

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, $6^{th}$ edition (Saunders, 2007).

"Aligning" means a method of comparing a test sequence, such as a sequence read, to one or more reference sequences to determine which reference sequence or which portion of a reference sequence is closest based on some sequence distance measure. An exemplary method of aligning nucleotide sequences is the Smith Waterman algorithm. Distance measures may include Hamming distance, Levenshtein distance, or the like. Distance measures may include a component related to the quality values of nucleotides of the sequences being compared.

"Amplicon" means the product of a polynucleotide amplification reaction: that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"): Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Clonality" as used herein, means a measure of the degree to which the distribution of clonotype abundances among clonotypes of a repertoire is skewed to a single or a few clonotypes. Roughly, clonality is an inverse measure of clonotype diversity. Many measures or statistics are available from ecology describing species-abundance relationships that may be used for clonality measures in accordance with the invention, e.g. Chapters 17 & 18, in Pielou, An introduction to Mathematical Ecology. (Wiley-Interscience, 1969). In one aspect, a clonality measure used with the invention is a function of a clonotype profile (that is, the number of distinct clonotypes detected and their abundances), so that after a clonotype profile is measured, clonality may be computed from it to give a single number. One clonality measure is Simpson's measure, which is simply the probability that two randomly drawn clonotypes will be the same. Other clonality measures include information-based measures and Mcintosh's diversity index, disclosed in Pielou (cited above).

"Clonotype" means a recombined nucleotide sequence of a lymphocyte which encodes an immune receptor or a portion thereof. More particularly, clonotype means a recombined nucleotide sequence of a T cell or B cell which encodes a T cell receptor (TCR) or B cell receptor (BCR), or a portion thereof. In various embodiments, clonotypes may encode all or a portion of a VDJ rearrangement of IgH, a DJ rearrangement of IgH, a VJ rearrangement of IgK, a VJ rearrangement of IgL, a VDJ rearrangement of TCR β, a DJ rearrangement of TCR β, a VJ rearrangement of TCR α, a VJ rearrangement of TCR γ, a VDJ rearrangement of TCR δ, a VD rearrangement of TCR δ, a Kde-V rearrangement, or the like. As used herein, "VDJ" or equivalently "V(D)J" represent recombined sequences that have undergone P and/or N nucleotide additions or subtractions, e.g. Janeway et al, Immunobiology, Sixth Edition (Garland Science, New York, 2005). Thus, in a VDJ segment, the D portion is sometimes represented as "NDN" to reflect such additional processing. In some case, the nomenclature wilt further distinguish the N regions as $N_1$ (between D and J) and $N_2$ (between D and V), so that a VDJ region may be equivalently represented as "$VN_2DN_1J$". Clonotypes may also encode translocation breakpoint regions involving immune receptor genes, such, as Bc11-IgH or Bc11-IgH. In one aspect, clonotypes have sequences that are sufficiently long to represent or reflect the diversity of the immune molecules dial they are derived from; consequently, clonotypes may vary widely in length. In some embodiments, clonotypes have lengths in the range of from 25 to 400 nucleotides; in other embodiments, clonotypes have lengths in the range of from 25 to 200 nucleotides. Clonotypes associated with a disease are referred, to herein interchangeably as "correlating clonotypes" or "index clonotypes".

"Clonotype profile" means a listing of distinct clonotypes and their relative abundances that are derived from a population of lymphocytes. Typically, the population of lymphocytes are obtained from a tissue sample. The term "clonotype profile" is related to, but more general than, the immunology concept of immune "repertoire" as described in references, such as the following: Arstila et al, Science, 286: 958-961 (1999); Yassai et al, Immunogenetics, 61: 493-502 (2009); Kedzierska et al, Mol. Immunol., 45(3): 607-618 (2008): and the like. The term "clonotype profile" includes a wide variety of lists and abundances of rearranged immune receptor-encoding nucleic acids, which may be derived from selected subsets of lymphocytes (e.g. tissue-infiltrating lymphocytes, immunophenotypic subsets, or the like), or which may encode portions of immune receptors that have reduced diversify as compared to full immune receptors. In some embodiments, clonotype profiles may comprise at least $10^3$ distinct clonotypes; in other embodiments, clonotype profiles may comprise at least $10^4$ distinct clonotypes; in other embodiments, clonotype profiles may comprise at least $10^5$ distinct clonotypes; in other embodiments, clonotype profiles may comprise at least $10^6$ distinct clonotypes. In such embodiments, such clonotype profiles may further comprise abundances or relative frequencies of each of the distinct clonotypes. In one aspect, a clonotype profile is a set of distinct recombined nucleotide sequences (with their abundances) that encode T cell receptors (TCRs) or B cell receptors (BCRs), or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. In one aspect, nucleic acid segments defining clonotypes are selected so that their diversity (i.e. the number of distinct nucleic acid sequences in the set) is large enough so that substantially every T cell or B cell or clone thereof in an individual carries a unique nucleic acid sequence of such repertoire. That is, preferably each different clone of a sample has different clonotype. In other aspects of the invention, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined by cell surface markers, or the like. Such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In one embodiment, a clonotype profile comprising human TCR β chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$. In another embodiment, a clonotype profile comprising human IgH chains or fragments thereof comprises a number of distinct nucleotide sequences in the range of from $0.1 \times 10^6$ to $1.5 \times 10^6$, or in the range of from $0.5 \times 10^6$ to $1.5 \times 10^6$, or in the range of from $0.8 \times 10^6$ to $1.2 \times 10^6$. In a particular embodiment, a clonotype profile of the invention comprises a set of nucleotide sequences encoding substantially all segments of the V(D)J region of an IgH chain. In one aspect, "substantially all" as used herein means every segment having a relative abundance of 0.001 percent or higher; or in another aspect, "substantially all" as used herein means every segment having a relative abundance of 0.0001 percent or higher, in another particular embodiment, a clonotype profile of the invention comprises a set of nucleotide sequences that encodes substantially all segments of the V(D)J region of a TCR β chain. In another embodiment, a clonotype profile of the invention comprises a set of nucleotide sequences having lengths in the range of from 25-200 nucleotides and including segments of the V, D, and J regions of a TCR β chain. In another embodiment, a clonotype profile of the invention comprises a set of nucleotide sequences having lengths in the range of from 25-200 nucleotides and including segments of the V, D, and J regions of an IgH chain. In another embodiment, a clonotype profile of the invention comprises a number of distinct nucleotide sequences that is substantially equivalent to the number of lymphocytes expressing a distinct IgH chain. In another embodiment, a clonotype profile of the invention comprises a number of distinct nucleotide sequences that is substantially equivalent to the number of lymphocytes expressing a distinct TCR β chain. In still another embodiment, "substantially equivalent" means that with ninety-nine percent probability a clonotype profile will include a nucleotide sequence encoding an IgH or TCR β or portion thereof carried or expressed by every lymphocyte of a population of an individual at a frequency of 0.001 percent or greater. In still another embodiment, "substantially equivalent" means that with ninety-nine percent probability a repertoire of nucleotide sequences will include a nucleotide sequence encoding art IgH or TCR β or portion thereof carried or expressed by every lymphocyte present at a frequency of 0.0001 percent or greater. In some embodiments, clonotype profiles are derived from samples comprising from $10^5$ to $10^7$ lymphocytes. Such numbers of lymphocytes may be obtained from peripheral blood samples of from 1-10 mL.

"Coalescing" means treating two candidate clonotypes with sequence differences as the same by determining that such differences are due to experimental or measurement error and not doe to genuine biological differences. In one aspect, a sequence of a higher frequency candidate clonotype is compared to that of a lower frequency candidate clonotype and if predetermined criteria are satisfied then the number of lower frequency candidate clonotypes is added to that of the higher frequency candidate clonotype and the lower frequency candidate clonotype is thereafter disregarded. That is, the read counts associated with the lower frequency candidate clonotype are added to those of the higher frequency candidate clonotype.

"Complementarity determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes sonic of V, all of diverse (D) (heavy chains only) and joint (J), and some of the constant (C) domains.

"Lymphoid neoplasm" means an abnormal proliferation of lymphocytes that may be malignant or non-malignant. A lymphoid cancer is a malignant lymphoid neoplasm. Lymphoid neoplasms are the result of, or are associated with, lymphoproliferative disorders, including but not limited to, follicular lymphoma, chronic lymphocytic leukemia (CLL), acute lymphocytic leukemia (ALL), hairy cell leukemia, lymphomas, multiple myeloma, post-transplant lymphoproliferative disorder, mantle cell lymphoma (MCL), diffuse large B cell lymphoma (DLBCL), T cell lymphoma, or the like, e.g. Jaffe et al, Blood, 112:4384-4399 (2008); Swerdlow et al, WHO Classification of Tumours of Haematopoietic and Lymphoid Tissues (e. $4^{th}$) (IARC Press, 2008).

"Minimal residual disease" means remaining cancer cells after treatment. The term is most frequently used in connection with treatment of lymphomas and leukemias.

"Pecent homologous," "percent identical," or like terms used in reference to the comparison, of a reference sequence and another sequence ("comparison sequence") mean that in an optimal alignment between the two sequences, the comparison sequence is identical to the reference sequence in a number of subunit positions equivalent to the indicated percentage, the sub-units being nucleotides for polynucleotide comparisons or amino acids for polypeptide comparisons. As used herein, an "optimal alignment" of sequences being compared is one that maximizes matches between subunits and minimizes the number of gaps employed in constructing an alignment. Percent, identities may be determined with commercially available implementations of algorithms, such as that described by Needleman and Wunsch, J. Mol. Biol., 48: 443-453 (1970)("GAP" program of Wisconsin Sequence Analysis Package, Genetics Computer Group, Madison, Wis.), or the like. Other software packages in the art for constructing alignments and calculating percentage identity or other measures of similarity include the "BestFit" program, based on the algorithm of Smith and Waterman, Advances in Applied Mathematics, 2: 482-489 (1981) (Wisconsin Sequence Analysis Package. Genetics Computer Group, Madison, Wis.). In other words, for example, to obtain a polynucleotide having a nucleotide sequence at least 95 percent identical to a reference nucleotide sequence, up to five percent of the nucleotides in the reference sequence may be deleted or substituted with another nucleotide, or a number of nucleotides up to five percent of the total number of nucleotides in the reference sequence may be inserted into the reference sequence.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references; McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi el al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al Anal. Biochem., 273: 221-228 (1999)(two-color real-time PCR). Usually, distinct sets of primers are employed for each sequence being amplified. Typically, the number of target sequences in a multiplex PCR. is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" refers to a linear polymer of nucleotide monomers and may be DNA or RNA. Monomers making up polynucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof e.g., naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Polynucleotides may comprise the four natural nucleosides (e.g. deoxyadenosine, deoxycytidine, deoxyguanosine, deoxythymidine for DNA or their ribose counterparts for RNA) linked by phosphodiester linkages. However, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity (e.g. single stranded DNA, RNA/DNA duplex, or the like), then selection of an appropriate composition for the oligonucleotide or polynucleotide substrates is well within the knowledge of one of ordinary skill, especially with guidance from treatises such as Sambrook et al, MOLECULAR CLONING. 2nd ed. (Cold Spring Harbor Laboratory, New York, 1989), and like references. As used herein, the term "oligonucleotide" refers to smaller polynucleotides, for example, having 3-60 monomeric units, or in some embodiments having from 12 to 60 monomeric units. In various embodiments, a polynucleotide or oligonucleotides may be represented by a sequence of letters (upper or lower ease), such as "ATGCCTG," and it will be understood that the nucleotides are in 5'→3' order from left to right and that "A" denotes deoxyadenosine, "C" denotes deoxycytidine, "G" denotes deoxyguanosine, and "T" denotes thymidine, "T" denotes deoxyinosine, "U" denotes uridine, unless otherwise indicated or obvious from context.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more printers. Guidance for selecting the lengths and sequences of primers for particular applications is well known to those of ordinary skill in the art, as evidenced by the following references that are incorporated by reference: Dieffenbach, editor, PCR Primer: A Laboratory Manual, $2^{nd}$ Edition (Cold Spring Harbor Press, New York, 2003).

"Quality score" means a measure of the probability that a base assignment at a particular sequence location is correct. A variety methods are well known to those of ordinary skill for calculating quality scores for particular circumstances, such as, for bases called as a result of different sequencing chemistries, detection systems, base-calling algorithms, and so on. Generally, quality score values are monotonically related to probabilities of correct base calling. For example, a quality score, or Q, of 10 may mean that there is a 90 percent chance that a base Is called correctly, a Q of 20 may mean that there is a 99 percent chance that a base is called correctly, and so on. For some sequencing platforms, particularly those using sequencing-by-synthesis chemistries, average quality scores decrease as a function of sequence read length, so that quality scores at the beginning of a sequence read are higher than those at the end of a sequence read, such declines being due to phenomena such as incomplete extensions, carry forward extensions, loss of template, loss of polymerase, capping failures, deprotection failures, and the like.

"Sequence read" means a sequence of nucleotides determined from a sequence or stream of data generated by a sequencing technique, which determination is made, for example, by means of base-calling software associated with the technique, e.g. base-calling software from a commercial provider of a DNA sequencing platform. A sequence read usually Includes quality scores for each nucleotide in the sequence. Typically, sequence reads are made by extending a primer along a template nucleic acid, e.g. with a DNA polymerase or a DNA ligase. Data is generated by recording signals, such as optical chemical (e.g. pH change), or electrical signals, associated with such extension. Such initial data is converted into a sequence read.

What is claimed is:

1. A method of determining that a clonotype is evolved by $V_H$ substitution from one or more patient-specific clonotypes correlated with a B-cell acute lymphoblastic leukemia (ALL), the method comprising:
  (a) amplifying nucleic acid molecules from B-cells in a sample from a B-cell ALL patient, the nucleic acid molecules comprising or derived from recombined DNA sequences from immunoglobulin genes, thereby generating amplified nucleic acid molecules;
  (b) sequencing the amplified nucleic acid molecules to form a clonotype profile; and
  (c) determining from the clonotype profile that a clonotype evolved by $V_H$ substitution from one or more patient-specific clonotypes correlated with the B-cell ALL, wherein the clonotype is considered evolved from a patient-specific clonotype correlated with the B-cell ALL if at least six consecutive nucleotides extending in a $V_H$ direction from a J-NDN boundary are identical in the evolved clonotype and the clonotype correlated with the B-cell ALL.

2. The method of claim 1, further comprising repeating steps (a) through (c) on nucleic acid molecules from a successive sample from the patient to determine from the clonotype profile formed from the amplified nucleic acid molecules from the successive sample that a clonotype evolved by $V_H$ substitution from one or more patient-specific clonotypes correlated with the B-cell ALL.

3. The method of claim 1, wherein the nucleic acid molecules comprise at least a portion of a VDJ region.

4. The method of claim 1, wherein the clonotype profile includes every clonotype present among the amplified nucleic acid molecules at a frequency of 0.001 percent or greater with a probability of ninety-nine percent.

5. The method of claim 1, wherein the clonotype profile includes at least $10^4$ clonotypes.

6. The method of claim 1, wherein the sample is a sample of bone marrow or a sample of peripheral blood.

7. The method of claim 1, wherein the $V_H$ substitution is a $V_H$ replacement.

8. The method of claim 1, further comprising determining from the clonotype profile the presence, absence and/or level of the one or more patient-specific clonotypes and the evolved clonotype.

9. The method of claim 8, further comprising a step of modifying a treatment of the B-cell ALL of the patient based on the presence, absence and/or level of the one or more patient-specific clonotypes and the evolved clonotype.

10. The method of claim 2, further comprising determining from the clonotype profile the presence, absence and/or level of the one or more patient-specific clonotypes and the evolved clonotype in the sample and the successive sample and comparing the levels of the one or more patient-specific clonotypes and the evolved clonotype in the sample and the successive sample.

11. The method of claim 10, wherein (a) the B-cell ALL is a childhood ALL, (b) the level of the one or more patient-specific clonotypes and the evolved clonotype increases in the successive sample, and (c) the step of modifying a treatment comprises administering an anti-ALL agent different from an anti-ALL agent administered in an induction therapy.

12. The method of claim 10, wherein (a) the B-cell ALL is a childhood ALL, (b) the level of the one or more patient-specific clonotypes and the evolved clonotype increases in the successive sample, and (c) the step of modifying a treatment comprises performing a bone marrow transplant on the patient.

13. The method of claim 1, wherein the step of determining comprises comparing the at least six consecutive nucleotides extending $V_H$ direction from a J-NDN boundary in a clonotype from the clonotype profile with the one or more patient-specific clonotypes and/or previously recorded clonotypes clonally evolved by $V_H$ substitution from the one or more patient-specific clonotypes.

14. The method of claim 13, wherein a clonotype from the clonotype profile is considered evolved from one or more patient-specific clonotypes correlated with the B-cell ALL based on identity of at least six consecutive nucleotides extending in a $V_H$ direction from a J-NDN boundary and likelihoods of occurrence of J segments, J deletions, NDN segments, V segments, or V deletions based on databases of clonotype sequences from populations of individuals.

15. The method of claim 14, wherein a clonotype from the clonotype profile is considered evolved from one or more patient-specific clonotypes correlated with the B-cell ALL based on likelihoods of occurrence in the B-cell ALL of D segments, positions of D segments in NDN segments, J-side deletions of D segments, or V-side deletions of D segments.

16. The method of claim 1, wherein the determination of a clonotype from the clonotype profile as evolved from one or more patient-specific clonotypes correlated with the B-cell ALL is made by using a naive Bayesian classifier model.

17. The method of claim 1, wherein the evolved clonotype is a previously unrecorded clonotype.

* * * * *

SEQUENCE LISTING

<160> NUMBER OF SEQ ID NOS: 6

<210> SEQ ID NO 1
<211> LENGTH: 56
<212> TYPE: DNA
<213> ORGANISM: Homo sapiens

<400> SEQUENCE: 1
gccccTcaag aagatagcag tggctgggac ggttgactac tggggccagg gaaccc          56

<210> SEQ ID NO 2
<211> LENGTH: 62
<212> TYPE: DNA
<213> ORGANISM: Homo sapiens

<400> SEQUENCE: 2
tgaggagggg ggcaagaaga tagcagtggc tgggacggtt gactactggg gccagggaac      60
cc                                                                    62

<210> SEQ ID NO 3
<211> LENGTH: 61
<212> TYPE: DNA
<213> ORGANISM: Homo sapiens

<400> SEQUENCE: 3 ccccccccc gcaagaagat agcagtggct gggacggttg actactgggg ccagggaacc       60
c                                                                     61

<210> SEQ ID NO 4
<211> LENGTH: 55
<212> TYPE: DNA
<213> ORGANISM: Homo sapiens

<400> SEQUENCE: 4
tcgaggtaag agatagcagt ggctgggacg gttgactact ggggccaggg aaccc           55

<210> SEQ ID NO 5
<211> LENGTH: 67
<212> TYPE: DNA
<213> ORGANISM: Homo sapiens

<400> SEQUENCE: 5
tattactgtg cgaaagatca gcggatagca gtggctggga cggttgacta ctggggccag      60
ggaaccc                                                               67

<210> SEQ ID NO 6
<211> LENGTH: 77
<212> TYPE: DNA
<213> ORGANISM: Homo sapiens

<400> SEQUENCE: 6
ctgaggacac ggctctgtat tactgtgcaa gaagatagca gtggctggga cggttgacta      60
ctggggccag ggaaccc                                                    77